US007883460B2

(12) United States Patent
Uchimura et al.

(10) Patent No.: US 7,883,460 B2
(45) Date of Patent: Feb. 8, 2011

(54) ENDOSCOPE

(75) Inventors: Sumihiro Uchimura, Sagamihara (JP); Akira Taniguchi, Hachioji (JP); Fumiyuki Onoda, Tama (JP); Toshiaki Noguchi, Tachikawa (JP); Katsuya Suzuki, Sagamihara (JP)

(73) Assignee: Olympus Corporation, Tokyo (JP)

( * ) Notice: Subject to any disclaimer, the term of this patent is extended or adjusted under 35 U.S.C. 154(b) by 1164 days.

(21) Appl. No.: 11/541,872

(22) Filed: Oct. 2, 2006

(65) Prior Publication Data

US 2007/0027361 A1    Feb. 1, 2007

Related U.S. Application Data

(63) Continuation of application No. PCT/JP2005/006493, filed on Apr. 1, 2005.

(30) Foreign Application Priority Data

Apr. 2, 2004   (JP) .............................. 2004-110483
Apr. 26, 2004  (JP) .............................. 2004-130129

(51) Int. Cl.
*A61B 1/00* (2006.01)

(52) U.S. Cl. ...................................... 600/146; 600/152

(58) Field of Classification Search ................ 600/146, 600/152
See application file for complete search history.

(56) References Cited

U.S. PATENT DOCUMENTS

| 4,566,437 | A | * | 1/1986 | Yamaguchi | 600/131 |
| 4,979,497 | A | * | 12/1990 | Matsuura et al. | 600/131 |
| 5,159,446 | A | * | 10/1992 | Hibino et al. | 348/65 |
| 5,188,111 | A | * | 2/1993 | Yates et al. | 600/434 |
| 5,609,563 | A |   | 3/1997 | Suzuki et al. | |
| 5,658,238 | A | * | 8/1997 | Suzuki et al. | 600/150 |
| 6,490,490 | B1 | * | 12/2002 | Uchikubo et al. | 700/65 |
| 6,752,758 | B2 | * | 6/2004 | Motoki et al. | 600/146 |
| 7,520,854 | B2 | * | 4/2009 | Sato | 600/118 |
| 2003/0069475 | A1 | | 4/2003 | Banik et al. | |

FOREIGN PATENT DOCUMENTS

| JP | 61-94633 | 5/1986 |
| JP | 38732/1990 | 4/1990 |
| JP | HEI 3-129101 | 12/1991 |
| JP | 5-265624 | 10/1993 |
| JP | 05-307143 | 11/1993 |
| JP | 06-54794 | 3/1994 |
| JP | 6-83530 | 3/1994 |
| JP | 7-124104 | 5/1995 |

(Continued)

OTHER PUBLICATIONS

Japanese Office Action dated Mar. 2, 2010.

*Primary Examiner*—Matthew J Kasztejna
(74) *Attorney, Agent, or Firm*—Scully, Scott, Murphy & Presser, P.C.

(57) ABSTRACT

An endoscope has an insertion portion provided with a freely curvable curving portion; a grip portion provided at a base end side of the insertion portion and grasped by an operator. There provided at the grip portion and in its periphery is an instructing operation element with a function of implementing a curve instructing operation of the curving portion and a function of implementing the other instructing operation different from the above described curve instructing operation.

27 Claims, 38 Drawing Sheets

FOREIGN PATENT DOCUMENTS

| | | |
|---|---|---|
| JP | 08-010336 | 1/1996 |
| JP | 09-276214 | 10/1997 |
| JP | 10-188737 | 7/1998 |
| JP | 2007-271065 A | 10/2000 |
| JP | 2004-121414 | 4/2004 |
| WO | 03/030727 A2 | 4/2003 |

* cited by examiner

WIRELESS SYSTEM

WIRED SYSTEM

OPTICAL COMMUNICATION SYSTEM

ENLARGED DIAGRAM

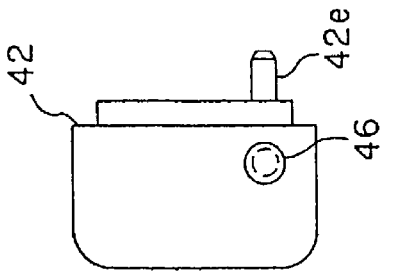
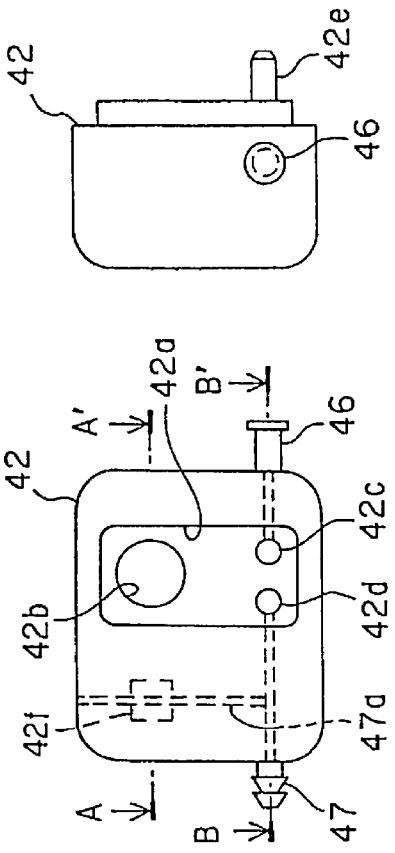
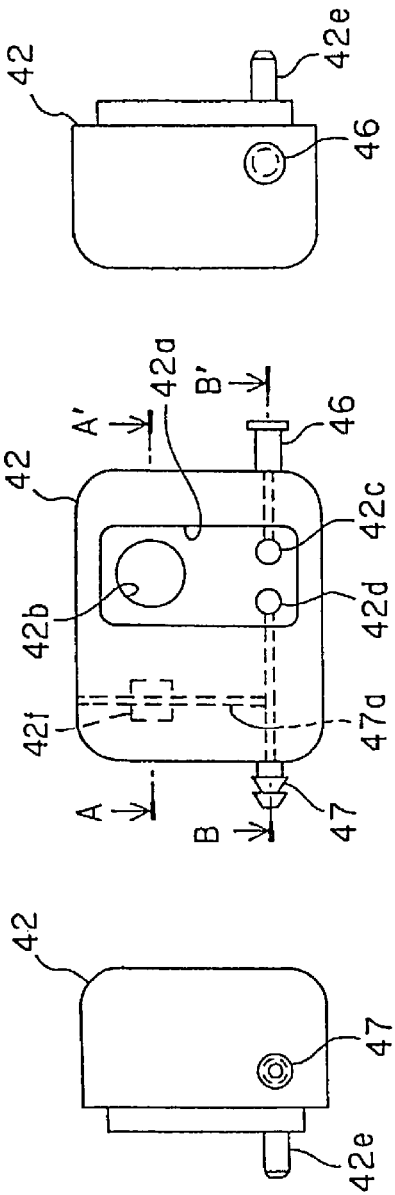
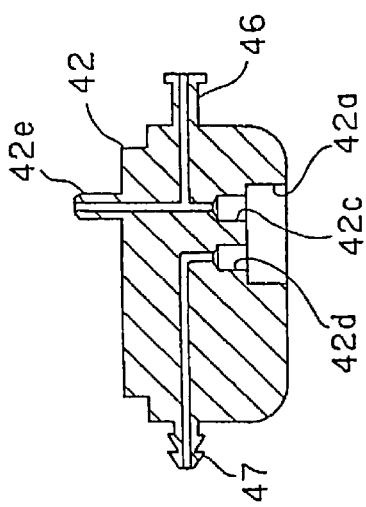
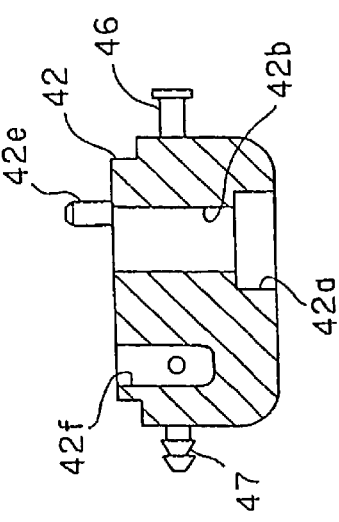

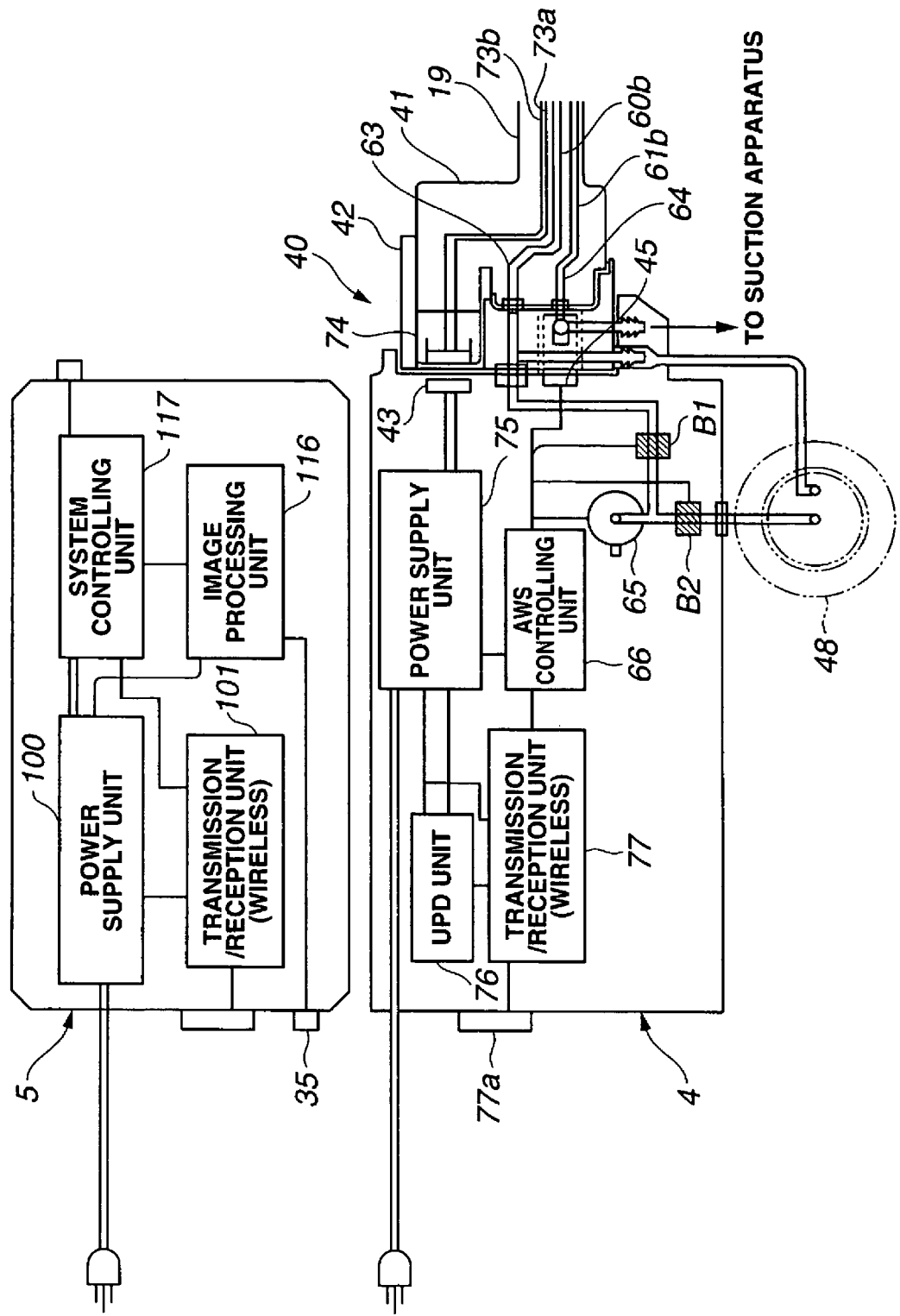

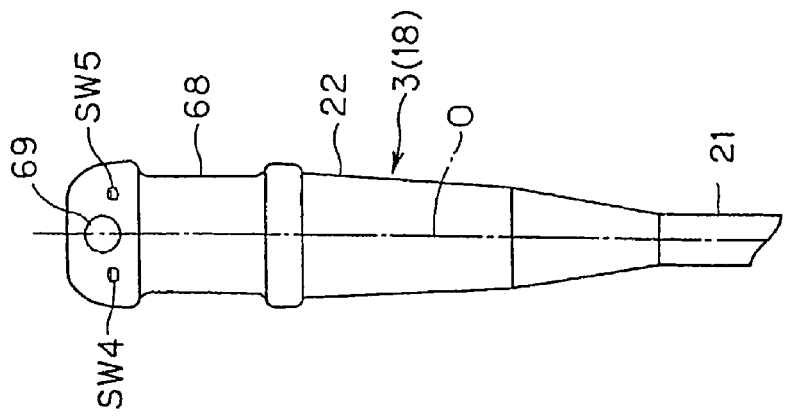
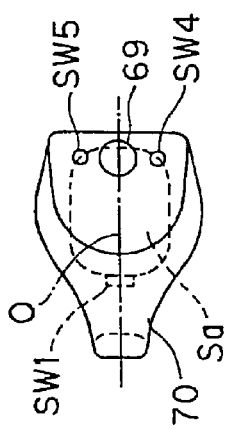
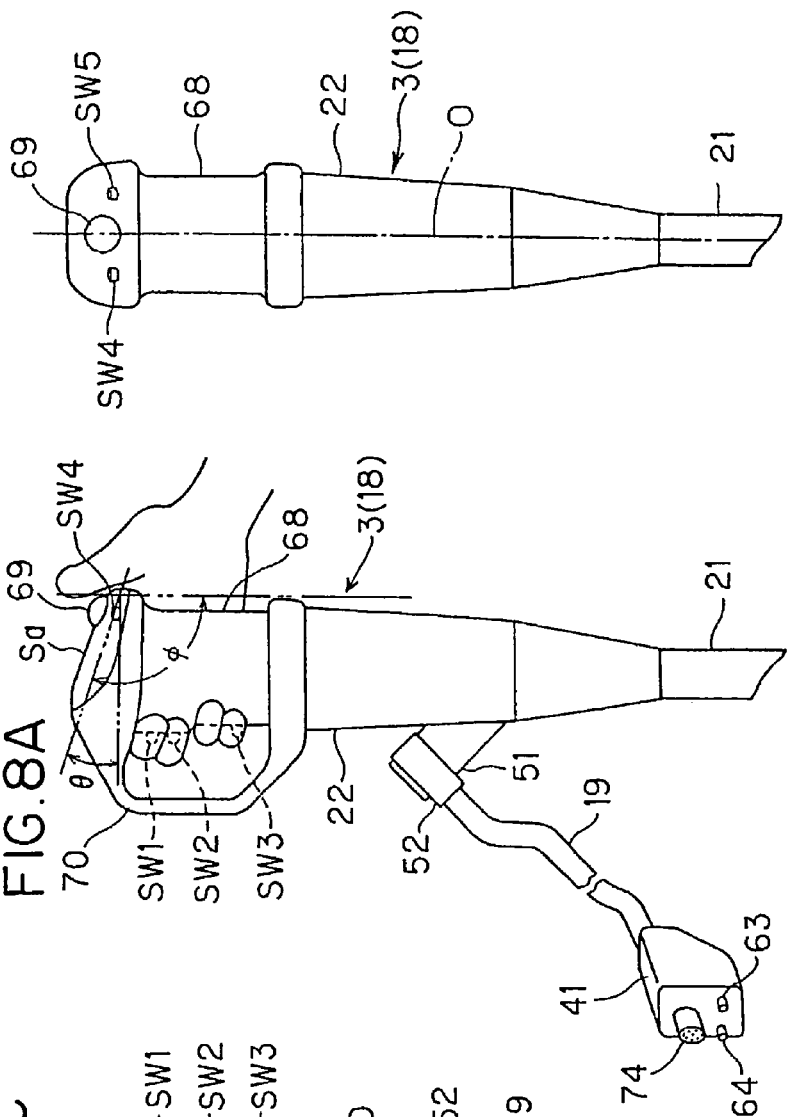
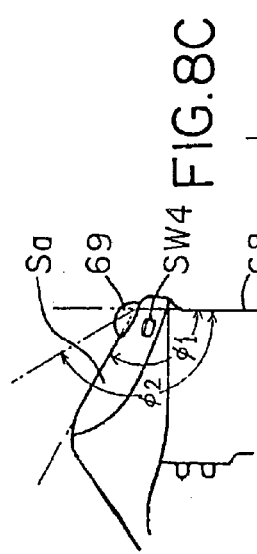
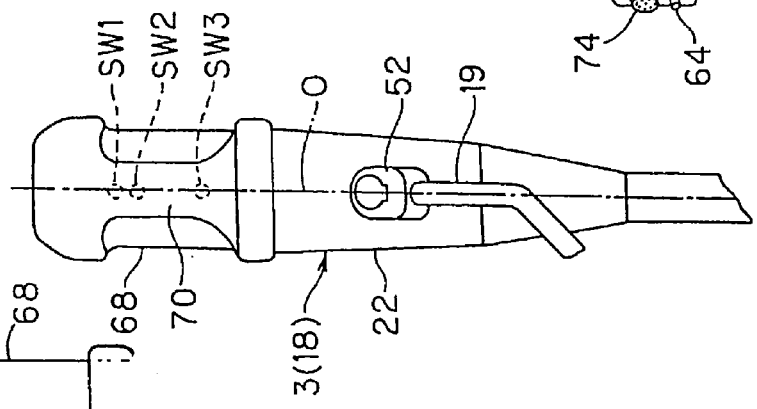

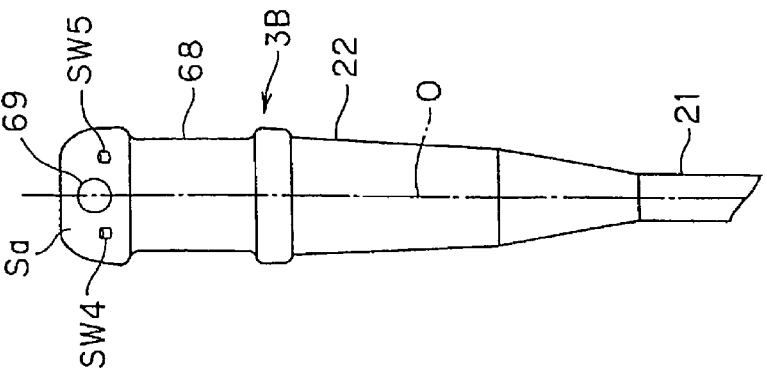
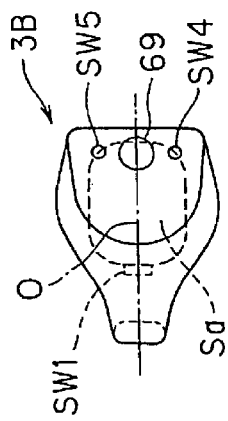
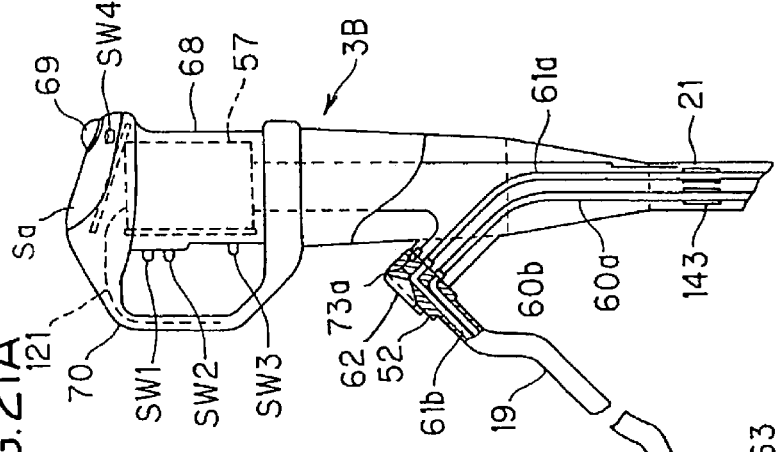
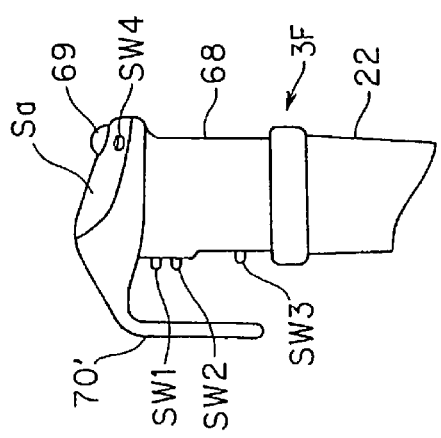

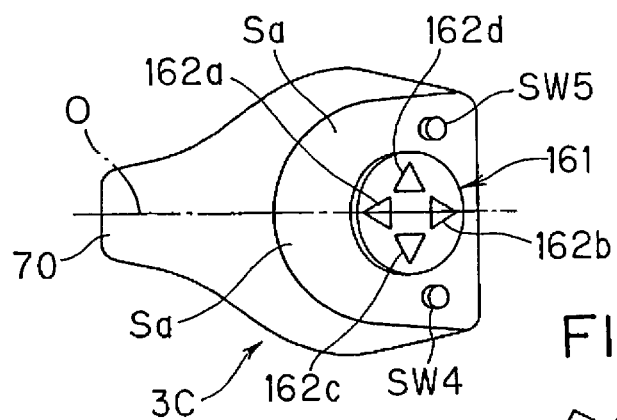
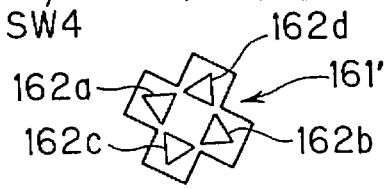
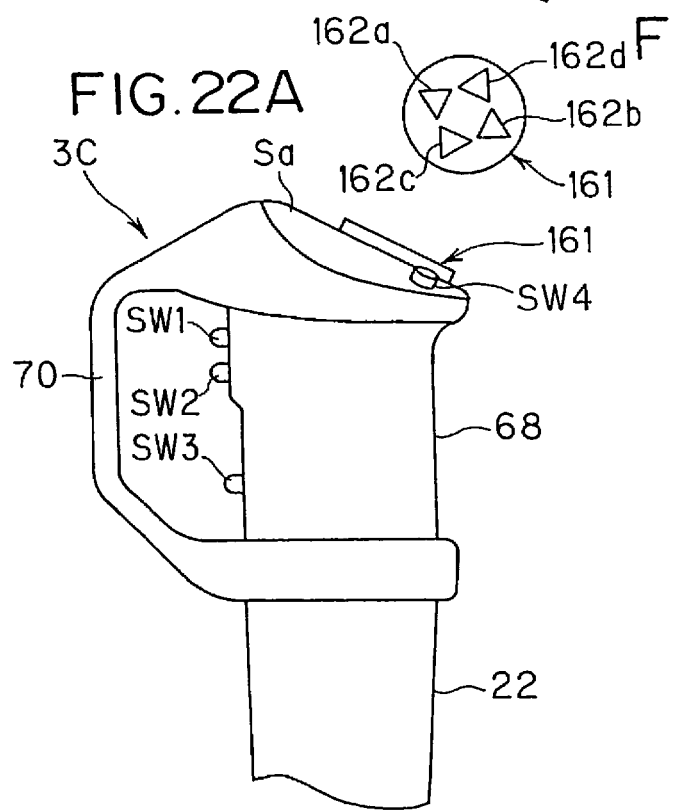
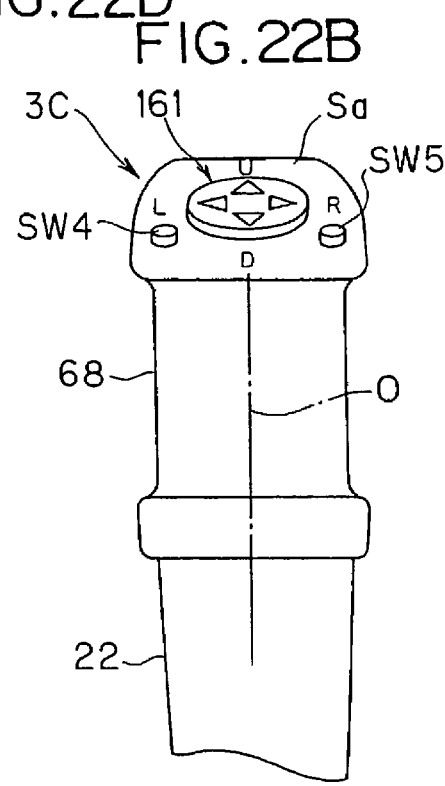

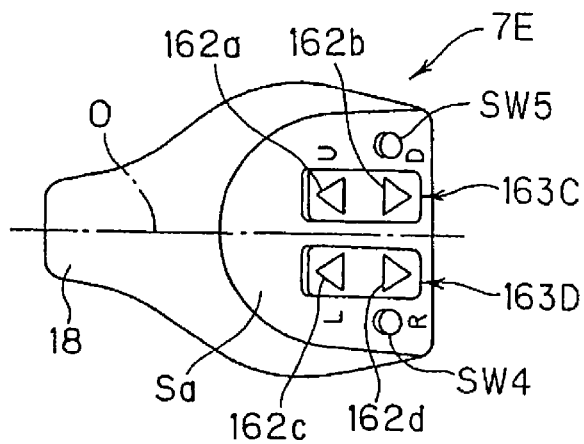
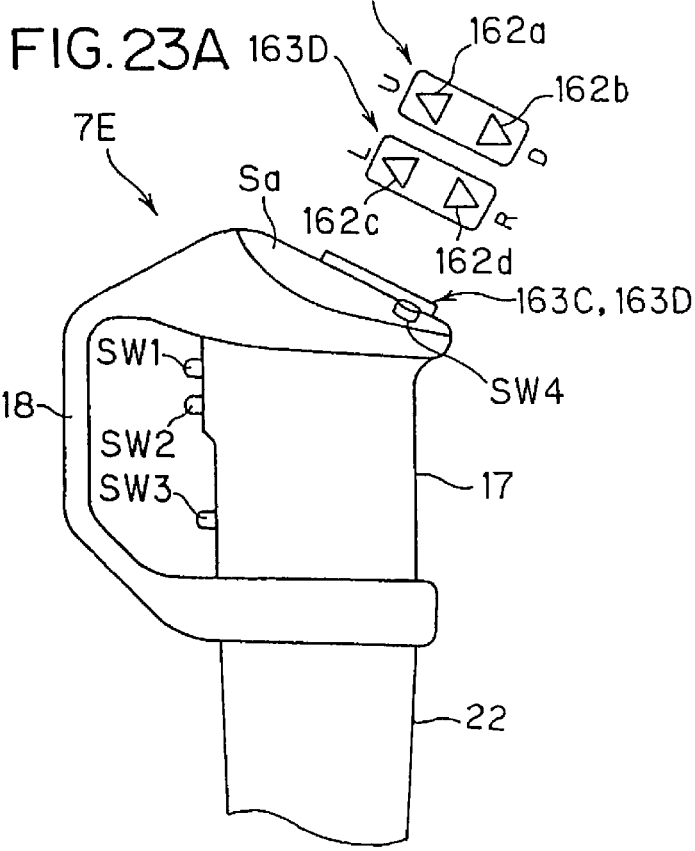
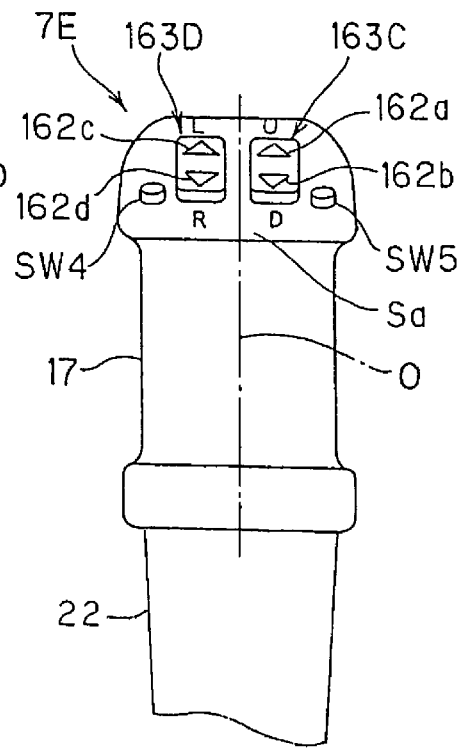

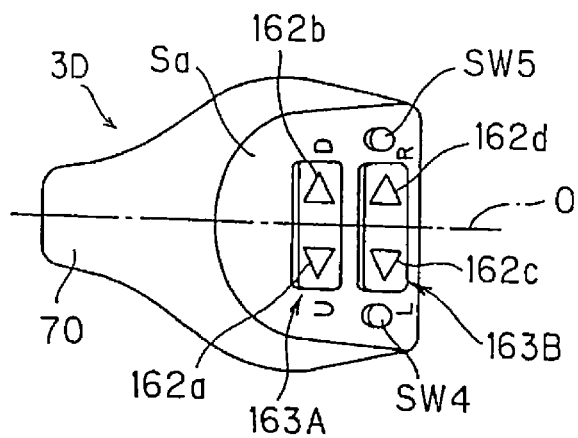
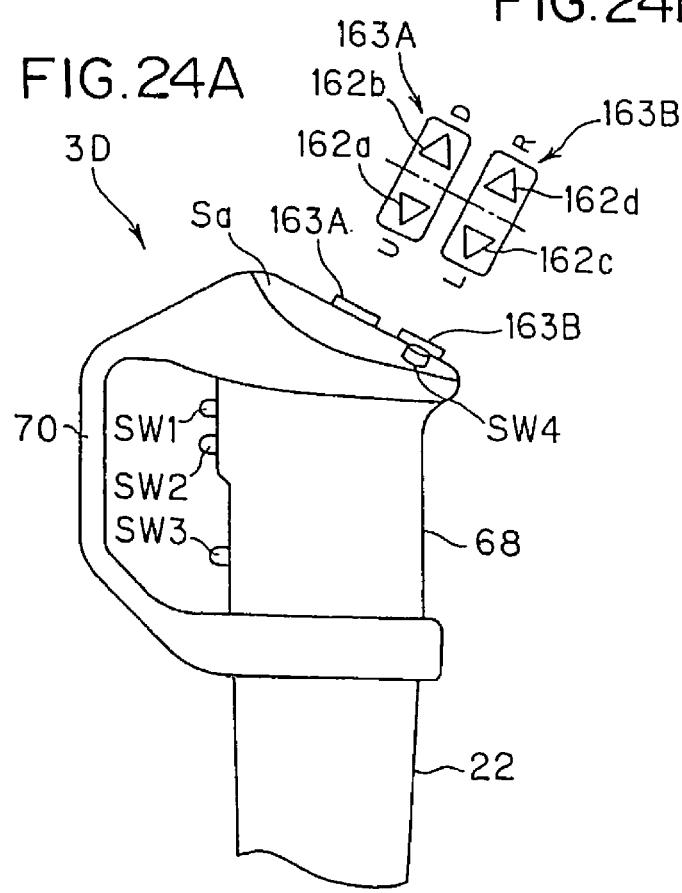
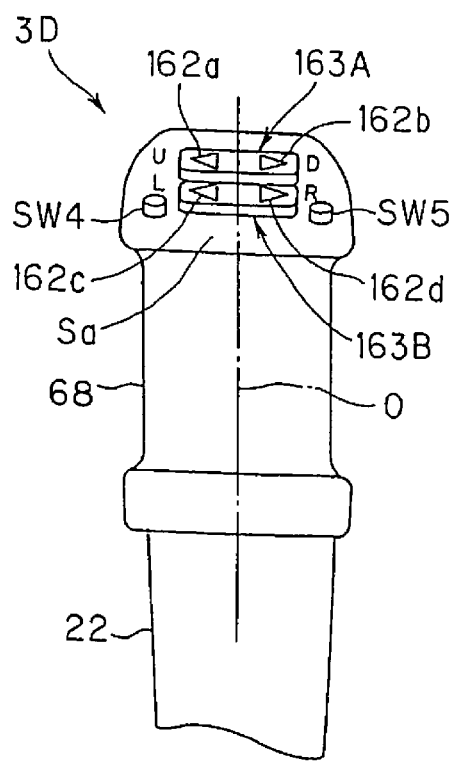

ENDOSCOPE

CROSS REFERENCE TO RELATED APPLICATION

This application is a continuation application of PCT/JP2005/006493 filed on Apr. 1, 2005 and claims benefit of Japanese Applications No. 2004-110483 filed in Japan on Apr. 2, 2004, and No. 2004-130129 filed in Japan on Apr. 26, 2004, the entire contents of each of which are incorporated herein by their reference.

BACKGROUND OF THE INVENTION

1. Field of the Invention

The present invention relates to an endoscope which is inserted into a body cavity to implement endoscope inspection and the like.

2. Description of the Prior Art

In recent years, an endoscope comprising lighting means as well as observation means at the tip of its long and narrow insertion portion has now been widely adopted in medical fields and industrial fields.

In particular, in the case of an endoscope having a flexing insertion portion, a curving portion is provided in the vicinity of the insertion portion so as to be inserted into a bent human body and enable observation in the desired directions and the curving portion is made capable of undergoing curving operation (angle operation) in an operation portion near hands.

In addition, in the case of an electronic endoscope with an image capturing element which is built in at the tip portion, the operation portion is provided with a plurality of scope switches, such as a freeze switch for instructing display of still pictures, to a signal processing apparatus of implementing signal processing on the image capturing element. And an operator is made capable of carrying out various kinds of operations with one hand grasping a grip portion in the operation portion.

In addition, there is Japanese Patent Application Laid-Open No. H9-276214, for example, as a prior art endoscopic apparatus subject to further improvement in operability so as to get capable of changing setting of a function of implementing allocation of the above described a plurality of scope switches changeable.

SUMMARY OF THE INVENTION

An endoscope of the present invention is characterized by comprising an insertion portion provided with a freely curvable curving portion; a grip portion provided at a base end side of the insertion portion and grasped by an operator; and instruction operation means, which is present at the grip portion and in its periphery, with a function of implementing a curve instructing operation of the curving portion and a function of implementing the other instructing operation different from the curve instructing operation.

BRIEF DESCRIPTION OF THE DRAWINGS

FIG. 5A is a front view showing structure of an AWS adaptor;

FIG. 5B is a left side view showing structure of an AWS adaptor;

FIG. 5C is a right side view showing structure of an AWS adaptor;

FIG. 5D is an A-A' section of FIG. 5A;

FIG. 5E is a B-B' section of FIG. 5A;

FIG. 6 is a block diagram showing an internal configuration of an endoscope system controlling apparatus and of an AWS unit;

FIG. 8A to FIG. 8E are drawings showing specific shapes of an endoscope in appearance and the like;

FIG. 21A to FIG. 21D are drawings showing specific shapes of an endoscope of Embodiment 2 of the present invention in appearance and the like;

FIG. 22A to FIG. 22E are drawings showing an endoscope of a second variation in the periphery of the operation portion;

FIG. 23A to FIG. 23D are drawings showing an endoscope of a third variation in the periphery of the operation portion;

FIG. 24A to FIG. 24D are drawings showing an endoscope of a fourth variation in the periphery of the operation portion;

DETAILED DESCRIPTION OF THE PREFERRED EMBODIMENTS

Embodiments of the present invention will be described with reference to drawings below.

Embodiment 1

With reference to FIG. 1 to FIG. 20, Embodiment 1 of the present invention will be described.

Figure 1:
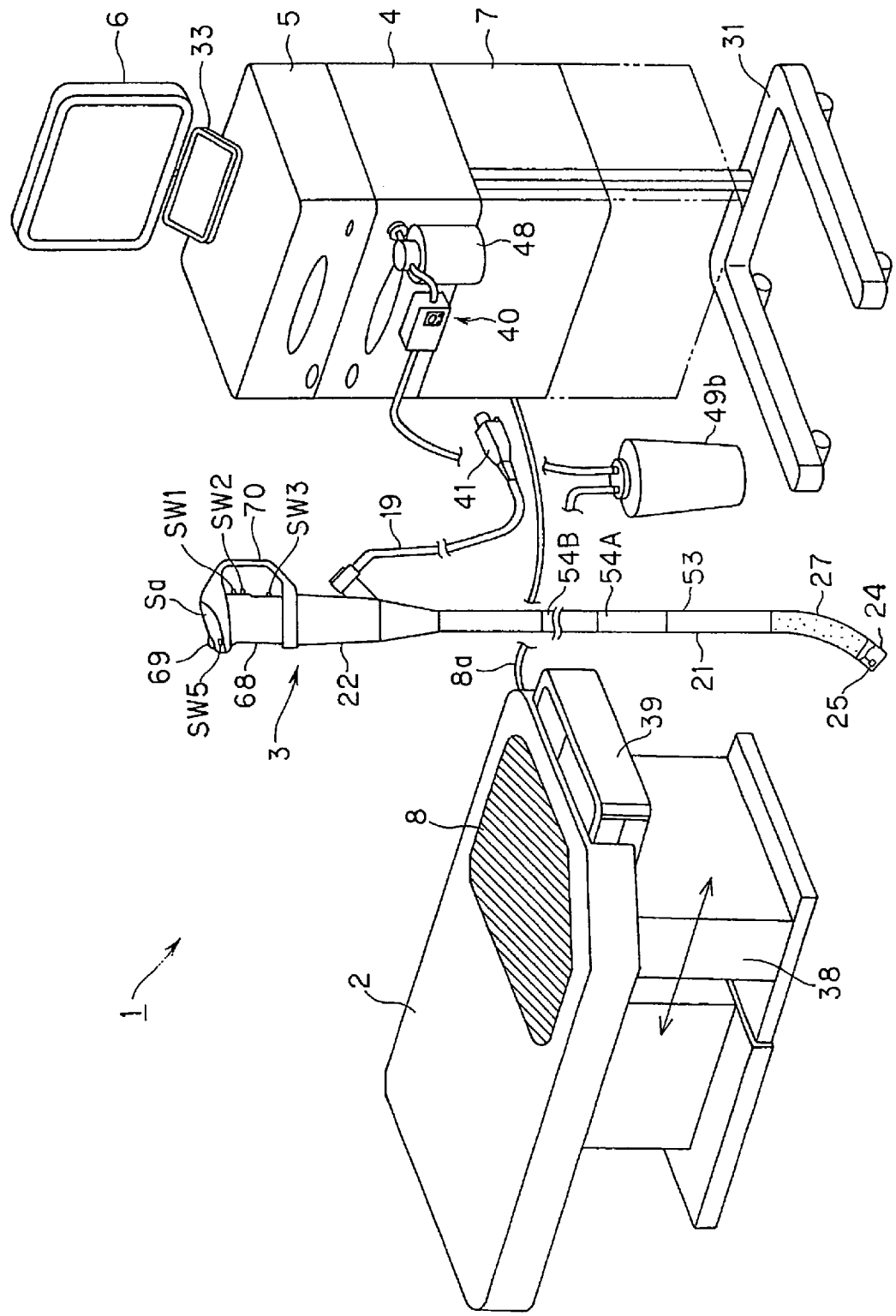
FIG. 1 is an entire configuration diagram of an endoscope system comprising the present invention.

As shown in FIG. 1, an endoscope system 1 comprising Embodiment 1 of the present invention has: a flexible endoscope (also called as a scope) 3 which is inserted inside a body cavity of a patient not shown in the drawing, who is lying down on an examination bed 2, carrying out endoscope inspection; a air-feed/water-feed/suction unit (hereinafter to be abbreviated as AWS unit) 4 to which the endoscope 3 thereof is connected and which comprises air-feed, water-feed and suction functions; endoscope system controlling apparatus 5 of carrying out signal processing for image capturing elements built-in in the endoscope 3, and controlling processing and video processing and the like on respective kinds of operation means provided in the endoscope 3; and an observation monitor 6 in use of a liquid crystal monitor and the like of displaying video signals generated by the endoscope system controlling apparatus 5 thereof. Here, that observation monitor 6 is provided with a touch panel 33.

In addition, the endoscope system 1 thereof is connected to an image recording unit 7 of carrying out filing digital image signals, for example, generated by the endoscope system controlling apparatus 5 and the AWS unit 4 and has a UPD coil unit 8 for receiving electromagnetic fields with the UPD coil thereof and the like to detect respective UPD coil positions and display shapes of the insertion portion of the endoscope 3 when a shape detection coil (hereinafter abbreviated as UPD coil) is incorporated in the insertion portion of the endoscope 3. In the case of FIG. 1, the UPD coil unit 8 is provided so as to be embedded on an upper surface of the examination bed 2. And, the UPD coil unit 8 thereof is connected to the AWS unit 4 with a cable 8a.

In addition, in the present embodiment, a housing concave portion is formed at one end in the longitudinal direction and in the lower location thereof in the examination bed 2 so as to be capable of housing a tray conveying trolley 38. A scope tray 39 where the endoscope 3 is housed is disposed on the top of that tray conveying trolley 38.

And, the scope tray 39 where the endoscope 3 subject to sterilization or disinfection can be conveyed with the tray conveying trolley 38 and can be housed in the housing concave portion of the examination bed 2. An operator can pull out the endoscope 3 from the scope tray 39 to use in endoscope inspection and the last thing to do is to house that scope tray 39 again after endoscope inspection is over. Thereafter, by conveying the scope tray 39 housing the post-use endoscope 3 with the tray conveying trolley 38, sterilization or disinfection can be carried out smoothly.

In addition, the AWS unit 4 and the endoscope system controlling apparatus 5 shown in FIG. 1 are arranged to carry out transmission/reception of information (data) wirelessly in the present embodiment. Here, in FIG. 1, the endoscope 3 is connected to the AWS unit with a tube unit 19, but it is also advisable that transmission/reception (bilateral transmission) of information (data) is carried out wirelessly. In addition, it is also advisable that the endoscope system controlling apparatus 5 is arranged to carry out transmission/reception of information wirelessly to and from the endoscope 3.

Figure 2A:
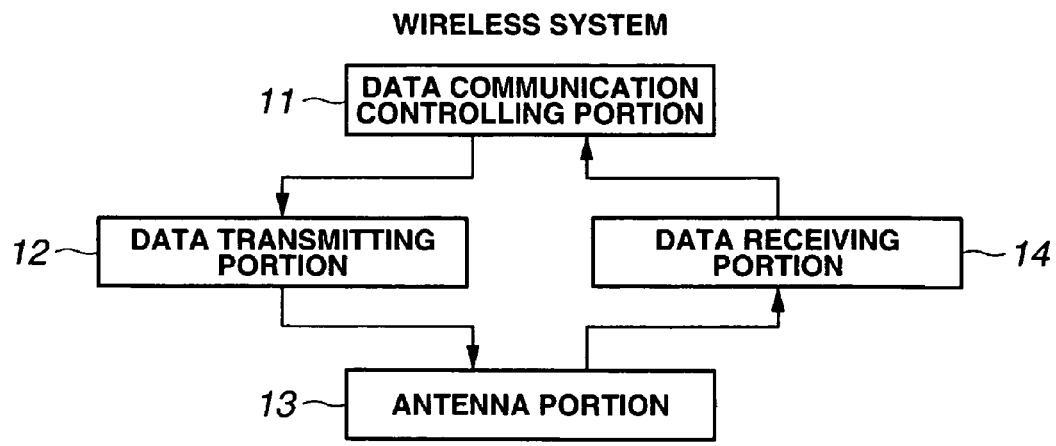
FIG. 2A is a diagram showing a data transmission mode in a wireless system used in the present invention.
Figure 2B:
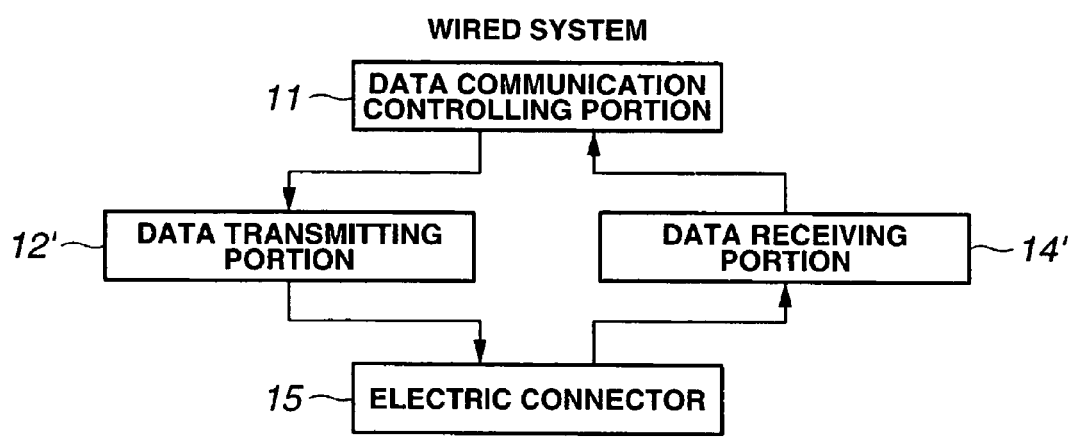
FIG. 2B is a diagram showing a data transmission mode in a wired system used in the present invention.
Figure 2C:
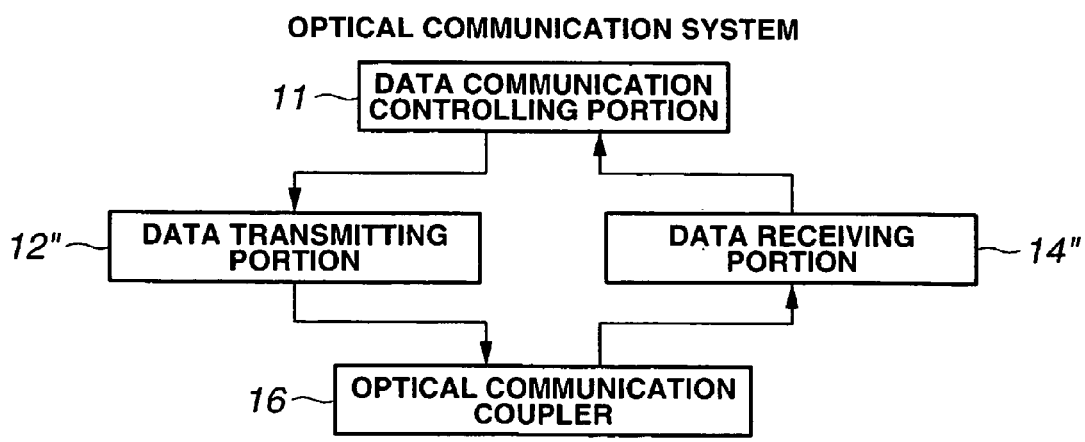
FIG. 2C is a diagram showing a data transmission mode in an optical communication system used in the present invention.

FIG. 2A to FIG. 2C show three systems in a transmission/reception unit (communication portion) of carrying out data transmission/reception between units as well as apparatuses in the endoscope system 1 or between the endoscope 3 and units or apparatus.

FIG. 2A shows a data transmission/reception unit in a wireless system. Here, a case of carrying out data transmission/reception between the AWS unit 4 and the endoscope system controlling apparatus 5 will be described.

Data for transmission are transmitted in a wireless system by the data communication controlling portion 11 built-in in the AWS unit 4 in a wireless system subject to modulation in the data transmitting portion 12 from an antenna portion 13 to the endoscope system controlling apparatus 5.

In addition, the AWS unit 4 receives, with the antenna portion 13, the data transmitted in wireless from the side of the endoscope system controlling apparatus 5 to carry out demodulation with the data receiving portion 14 and send those data to the data communication controlling portion 11. In the case of transmitting the data in a wireless system, the present embodiment forms a wireless LAN with the maximum data communication speed of 54 Mbps according to, for example, the standard of IEEE802.11 g.

FIG. 2B shows a data transmission/reception unit in a wired system. As a specific example, a case of carrying out data transmission/reception with the endoscope 3 and the AWS unit 4 will be described. Data transmitted from the endoscope 3 are transmitted by the data communicating controlling portion 11 built-in in the endoscope 3 from an electric connector 15 to the AWS unit 4 in a wired system via the data transmitting portion 12'. In addition, as for the data transmitted from the AWS unit 4, those data are sent to the data communicating controlling portion 11 via the electric connector 15 and the data receiving portion 14'.

FIG. 2C shows a data transmitting/receiving unit in an optical communication system. As a specific example, a case of carrying out data transmission/reception with the AWS unit 4 and the endoscope system controlling apparatus 5 will be described. The data communication controlling portion 11 built-in in the AWS unit 4 is connected to an optical communication coupler 16 provided in the AWS unit 4 thereof through a data transmitting portion 12" and a data receiving portion 14" of carrying out transmission and reception with light to transmit/receive the data through an optical communication coupler at the side of the endoscope system controlling apparatus 5. In addition, as shown in FIG. 1, the endoscope 3 of Embodiment 1 comprises an endoscope main body 18 and a tube unit 19, which is detachably connected to that endoscope main body 18 and, for example, is a throwaway type (disposable type).

The endoscope main body 18 has a longitudinal and flexible insertion portion 21 to be inserted into a body cavity and an operation portion 22 provided in the rear end of the insertion portion 21 thereof and a base end of the tube unit 19 is detachably connected to the operation portion 22 thereof.

In addition, an image capturing unit in use of a charge coupled device (herein abbreviated as CCD) 25 which makes gain variable inside the image capturing unit is disposed as an image capturing element in the tip portion 24 of the insertion portion 21.

In addition, a curving portion 27 capable of forming a curve with a low force amount is provided in the rear end of the tip portion 24 so as to curve the curving portion 27 by operating a track ball 69 as operation means (instruction inputting portion) provided in the operation portion 22. That track ball 69 is also used in the case of carrying out an angle operation (curving operation) and setting changes in the other scope switch functions, for example, settings of angle sensitivity and air-feed amount, and the like.

In addition, in the insertion portion 21, rigidity-variable portion provided with rigidity-variable actuators 54A and 54B to make rigidity variable is formed in a plurality of places so as to implement an inserting operation and the like more smoothly.

In the present embodiment, the AWS unit 4 and the endoscope system controlling apparatus 5 transmit/receive data with the wireless transmitting/receiving units 77 and 101 as shown, for example, in FIG. 6. In addition, the observation monitor 6 is connected to a monitor connector 35 of the endoscope system controlling apparatus 5 by a monitor cable.

As will be described below, image data having undergone image capturing with a CCD 25 as well as image data on shapes of the insertion portion of the endoscope 3 detected with a UPD coil unit 8 (UPD image) are transmitted to the endoscope system controlling apparatus 5, from the side of the AWS unit 4, and accordingly the endoscope system controlling apparatus 5 is designed to be capable of transmitting video signals corresponding with the image data thereof to the observation monitor 6 to display endoscope images as well as UPD images on the display screen thereof.

The observation monitor 6 is configured by a high definition TV (HDTV) monitor so as to be capable of displaying thus a plurality of kinds of images on that display screen concurrently.

In addition, as shown in FIG. 1, the AWS unit 4, for example, is provided with a scope connector 40. In addition, a scope connector 41 of the endoscope 3 is detachably connected to the scope connector 40 thereof.

Figure 3:
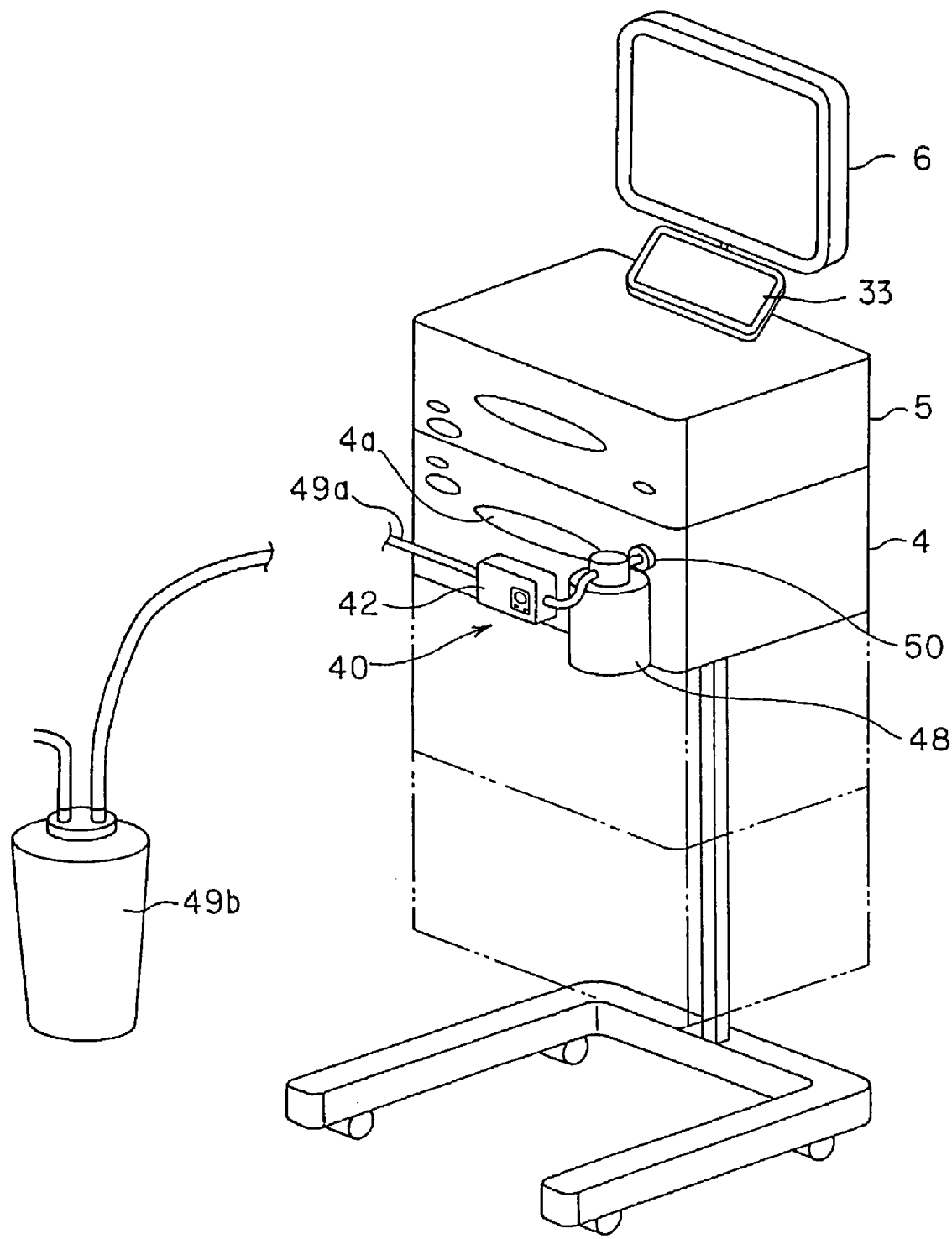
FIG. 3 is a perspective view showing a specific shape of an AWS unit in appearance in the periphery thereof.
Figure 4A:
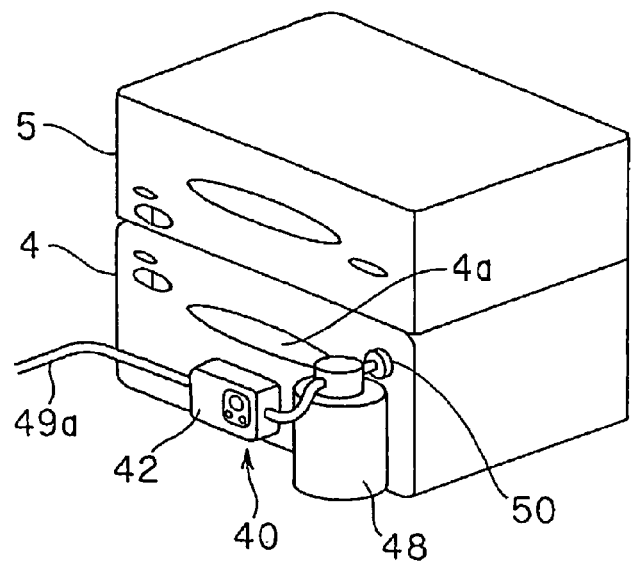
FIG. 4A is a perspective view showing an AWS unit in a state where an AWS adaptor is mounted thereon.

In that case, the shape of the scope connector 40 on the side of the AWS unit 4 is shown in appearance in FIG. 3 and FIG. 4. In addition, FIG. 5 shows structure of an AWS adaptor 42 detachably attached to the scope connector 40 of the AWS unit 4 and FIG. 6 shows, in a connected state, internal structure of the scope connector 40 on the side of the AWS unit 4 and the scope connector 41 on the side of the endoscope 3.

Figure 4B:
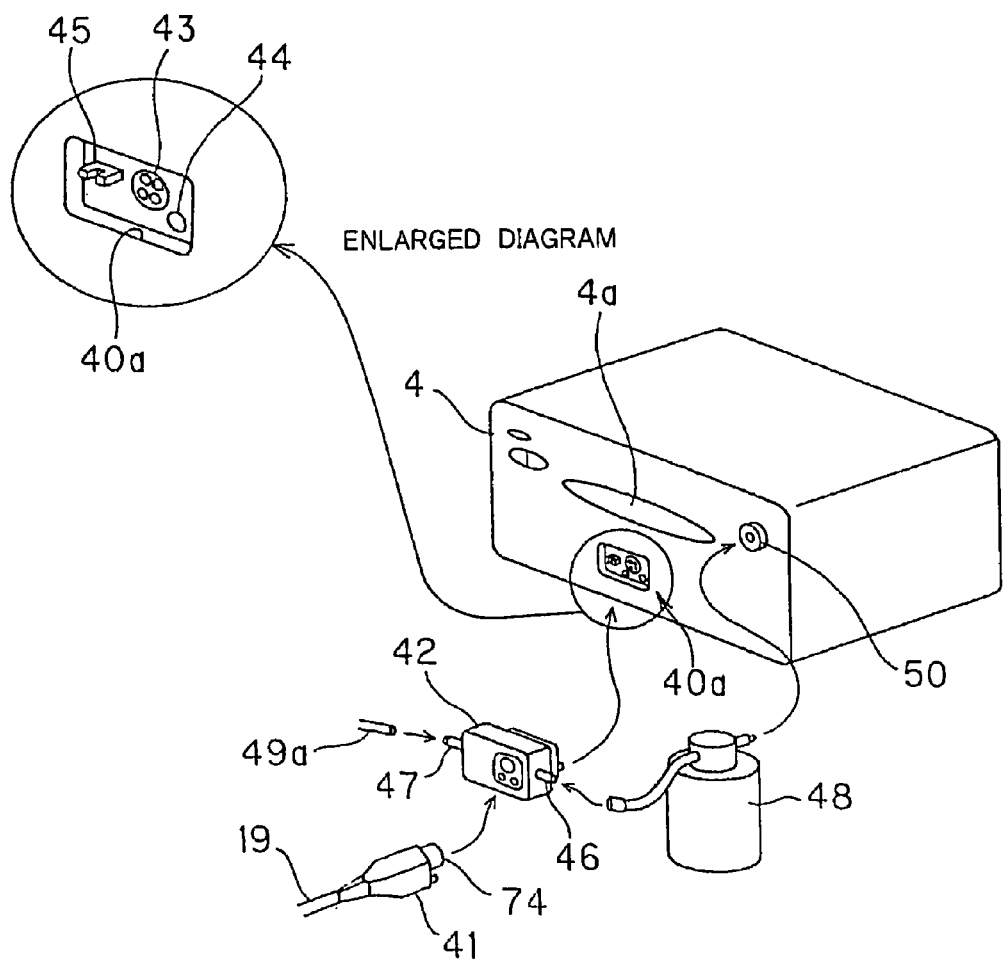
FIG. 4B is a perspective view showing an AWS unit in a state where the AWS adaptor has been removed.

Actually, as shown in FIG. 4B, a concave shape AWS adaptor attaching portion 40a is provided on the front side of the AWS unit 4, and the AWS adaptor (conduit connecting adaptor) 42 shown in FIG. 5 is mounted on the AWS adaptor attaching portion 40a thereof to form the scope connector 40 thereby and the scope connector 41 in the side of the endoscope 3 is connected to the scope connector 40 thereof.

The AWS adaptor attaching portion 40a is provided with a scope electric connector 43, an air-feed connector 44 and a pinch valve 45 so that the interior end side of the AWS adaptor 42 is detachably attached to the AWS adaptor attaching portion 40a while the scope connector 41 of the endoscope 3 is brought into connection from the exterior end side thereof.

That AWS adaptor 42 is shown in detail in FIG. 5. FIG. 5A shows a front view of the AWS adaptor 42; FIG. 5B and FIG. 5C show left and right side views; and FIG. 5D and FIG. 5E show A-A' section of FIGS. 5A and B-B' section of FIG. 5A respectively.

The scope connector 41 is inserted into the AWS adaptor 42 thereof in the concave portion 42a in the front side thereof, and in that case, the electric connector portion in the scope connector 41 is inserted into a through hole 42b provided inside the concave portion thereof so as to be connected to the scope electric connector 43 guided toward inside the through hole 42b thereof.

In addition, a water-feed/air-feed mouth ring 42c and a suction mouth ring 42d are provided in the lower side of the through hole 42b thereof so that the water-feed/air-feed mouth ring 63 and a suction mouth ring 64 (see FIG. 6 as well as FIG. 7) in the scope connector 41 are connected thereto respectively.

Here, a concave portion 42f of housing the pinch valve 45 protruding from the AWS adaptor attaching portion 40a is provided in the side of the base end of the AWS adaptor 42.

As shown in FIG. 5E, in the water-feed/air-feed mouth ring 42c provided in the AWS adaptor 42, the internal conduit communicated thereto is branched to form an air-feed mouth ring 42e connected to the air-feed connector 44 of the AWS unit 4 and a water-feed mouth ring 46 protruding in the side direction. In addition, in the suction mouth ring 42d, the conduit communicated thereto is bent in the side direction to form a suction mouth ring 47 protruding in the side face and form, for example, a relief conduit 47a branched upward halfway and the relief conduit 47a thereof is sandwiched by the pinch valve 45 halfway and thereafter the upper end thereof is open.

In the case of setting a suction pump, which is not shown in the drawing and forms suction means all time in an operating state, the relief conduit 47a thereof is ordinarily set to a releasing state by the pinch valve 45 so that the pinch valve 45 is driven in the case where a suction operation is carried out. And, the relief conduit 47a is closed by the pinch valve 45 and thereby the release is stopped so that the suction operation will be carried out.

The water-feed mouth ring 46 and the suction mouth ring 47 thereof are respectively connected to a water-feed tank 48 and (with a suction tank 49*b* caused to intervene halfway through the suction tube 49*a*) a suction device as shown in FIG. 3 or the like. The water-feed tank 48 is connected to the water-feed tank connector 50 of the AWS unit 4. Here, the operating panel 4*a* is provided in the upper side of the scope connector 40 in the front face of the AWS unit 4.

Next, with reference to FIG. 7 to FIG. 8E, a specific configuration of the endoscope 3 of Embodiment 1 of the present invention will be described. Here, FIG. 8A shows the vicinity of the operation portion of the endoscope 3 from the side; FIG. 8B shows a front view viewed from the right side of FIG. 8A; FIG. 8C shows a rear view viewed from the left side of FIG. 8A; and FIG. 8D shows a plan view viewed from above FIG. 8A. In addition, FIG. 8E shows an example of an angle range of a nearly optimum inclined surface.

In FIG. 1, as described on the diagrammatic points thereof, the flexible endoscope 3 comprises an endoscope main body 18 having a long and narrow flexible insertion portion 21 to be inserted into a body cavity and an operation portion 22 provided in the rear end of the insertion portion 21 thereof and a tube unit 19 of a disposable type (herein to be abbreviated as dispo type) in which a (tube unit connection) connector portion 51 provided in the vicinity of a base end (forward end) of the operation portion 22 in the endoscope main body 18 thereof is detachably connected to a comprehensive connector portion 52 of the base end thereof connected.

The above described scope connector 41 detachably connected to the AWS unit 4 is provided in the very end of the tube unit 19 thereof.

The insertion portion 21 comprises a rigid tip portion 24 provided in the tip of that insertion portion 21, a curving portion 27 curvably provided at the rear end of that tip portion 24 and a long and narrow flexible portion (meandering conduit portion) 53 from the rear end of that curving portion 27 to the operation portion 22. Rigidity-variable actuators 54A and 54B formed of electrically conductive polymer artificial muscle (to be abbreviated as EPAM) that expands/shrinks with voltage to be applied and can be changed in rigidity as well are provided in a plurality of places intervening the flexible portion 53 thereof, specifically in two places.

A light emitting diode 56 (to be abbreviated as LED) is attached, as lighting means, to the interior of lighting window provided in the tip portion 24 of the insertion portion 21 so that lighting light of that LED 56 is emitted forward through a lighting lens integrally attached to that LED 56 to light a shooting subject such as a patient and the like. Here, light emitting element of forming lighting means will not be limited to the LED 56 but can be formed with an LD (laser diode) and the like.

In addition, an object lens not shown in the drawing is mounted on the observation window provided adjacent to the lighting window and a CCD 25 with a gain-variable function being built-in is disposed in the image forming position thereof to form image capturing means of shooting a subject.

A signal line, respective end of which are connected to the LED 56 and the CCD 25 and inserted to go through inside the insertion portion 21 is provided inside the operation portion 22 and is connected to a controlling circuit 57 which carries out concentrated controlling processing (intensive controlling processing).

In addition, UPD coils 58 are provided in a predetermined distance in plurality along the longitudinal direction thereof inside the insertion portion 21. Signal lines connected to the respective UPD coils 58 are connected to the controlling circuit 57 through the UPD coil driving unit 59 provided inside the operation portion 22.

In addition, angle actuators 27*a* as an angle element (curving element) formed with EPAM disposed in the longitudinal direction thereof are provided in four places in the circumference direction in the interior of the outer skin in the curving portion 27. In addition, the angle actuator 27*a* thereof and the rigidity-variable actuators 54A and 54B are connected to the controlling circuit 57 respectively through the signal lines. The controlling circuit 57 is configured by mounting electronic circuit elements onto, for example, a switch substrate 57*a* and a track ball substrate 57*b*.

Figure 9A:
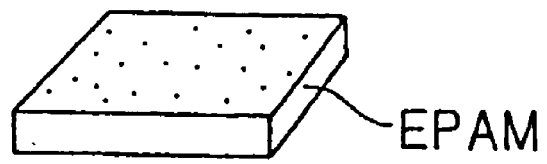
FIG. 9A to 9C are explanatory drawings for showing schematic functions of electrically conductive polymer artificial muscle (EPAM) used for an angle member and a rigidity-variable actuator.
Figure 9B:
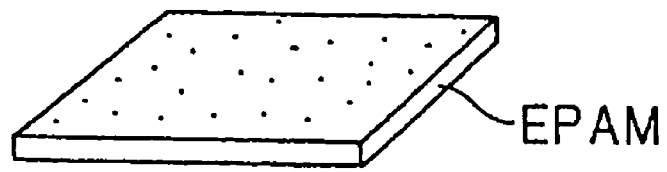
Figure 9C:
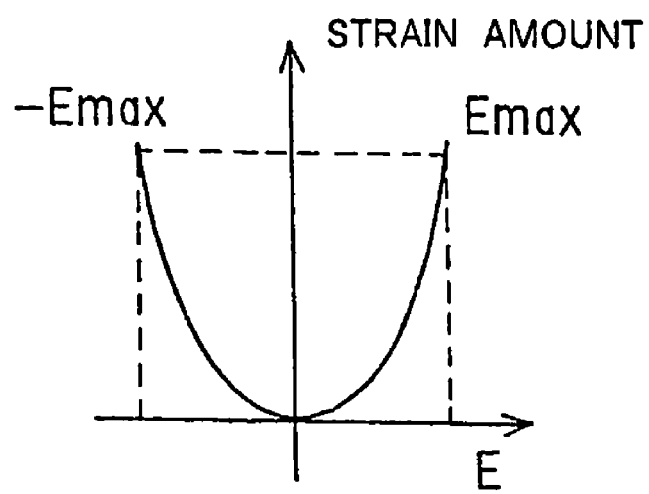

EPAM used in the angle actuator 27*a* and the rigidity-variable actuators 54A and 54B is shown in FIG. 9A. Electrodes are attached to the both sides of a plate-shaped EPAM by applying a voltage, which thereby can be caused to, for example, shrink in the thickness direction and expand in the longitudinal direction as shown in FIG. 9B. Here, it is possible to make the distortion amount of that EPAM variable, for example, in proportion to substantially the square of the electric field intensity E made by the applied voltage as shown in FIG. 9C.

In the case of utilizing it as an angle actuator 27*a*, it is formed to shape a wire and the like so that one is caused to expand and the opposite side is caused to shrink and thereby the curving portion 27 can be caused to curve likewise the function by an ordinary wire. In addition, those expansion or shrink can make rigidity thereof variable and utilization of function thereof makes rigidity of the portion thereof variable in the rigidity-variable actuators 54A and 54B.

In addition, an air-feed/water-feed conduit 60*a* and a suction conduit 61*a* are inserted through inside the insertion portion 21 and the rear end thereof forms a conduit connector 51*a* opening in the connector portion 51. And, a conduit connector 52*a* in a comprehensive connector portion 52 of the base end of the tube unit 19 is detachably connected to that conduit connector 51*a*.

And the air-feed/water-feed conduit 60*a* is connected to air-feed/water-feed conduit 60*b* inserted through the tube unit 19; the suction conduit 61*a* is connected to a suction conduit 61*b* inserted through the tube unit 19 and branched inside the conduit connector 52*a* to open externally to get communicated to an insertion port (also called as clamp port) 62 which enables insertion of treatment tools such as clamp and the like. The clamp port 62 thereof is blocked by a clamp cap 62*a* if it is not used.

The rear ends of the water-feed/air-feed conduit 60*b* and the suction conduit 61*b* thereof will become a water-feed/air-feed mouth ring 63 and a suction mouth ring 64 in the scope connector 41.

The water-feed/air-feed mouth ring 63 and the suction mouth ring 64 are respectively connected to the water-feed/air-feed mouth ring 42*c* and the suction mouth ring 42*d* of the AWS adaptor 42 shown in FIG. 4 and FIG. 5 and the like. And, as shown in FIG. 5, the water-feed/air-feed mouth ring 42*c* is branched into an air-feed conduit and a water-feed conduit in the interior of the AWS adaptor 42 so that the air-feed conduit is connected to an air-feed pump 65 in the interior of the AWS unit 4 with an electromagnetic valve B1 to intervene and the water-feed conduit is connected to the water-feed tank 48. In addition, that water-feed tank 48 is connected on its way to the air-feed pump 65 through the electromagnetic valve B2.

The air-feed pump 65 and the electromagnetic valves B1 and B2 are connected to the AWS controlling unit 66 with a controlling line (driving line) so that opening and closing is designed to be controlled with that AWS controlling unit 66 to carry out air-feed and water-feed. Here, the AWS controlling unit 66 controls the suction operation by controlling opening/closure of the pinch valve 45.

In addition, the operation portion 22 of the endoscope main body 18 is provided with a grip portion 68 which an operator grasps. In the present embodiment, as shown in FIG. 8A to FIG. 8D, that grip portion 68 is formed of, for example, a cylindrically shaped side portion in the vicinity of the rear end (base end) (to become an opposite side of the insertion portion 21 side) in the operation portion 22.

That grip portion 68 is provided, along a longitudinal direction of the grip portion 68 in the periphery thereof inclusive of that grip portion 68, with, for example, three scope switches SW1, SW2 and SW3, which carry out remote controlling operations (to be abbreviated as remocon) such as release, freeze and the like, and are connected to the controlling circuit 57 (see FIG. 7) respectively.

Moreover the base end face (also called as a top end face since the base end side is ordinarily set to come to the top and used for endoscope inspection as in FIG. 8) provided in the rear end (base end) of the grip portion 68 (or operation portion 22) shapes an inclined surface Sa and there provided in the vicinity of the opposite side of the position where the scope switches SW1, SW2 and SW3 in that inclined surface Sa are provided is a track ball 69 as instructing/operation means in charge of the function of carrying out curve instructing operation of the curving portion 27 and the function of remote operating (remocon operating) different from that curve instructing operation. That track ball 69 is in waterproof structure so as to be capable of setting angle operation (curving operation), the other remocon operations subject to switching from the angle operation and the like.

That track ball 69 is retained rotatably and the rotation amount thereof is structured to be detected by an encoder covered by waterproof film.

Figure 7:
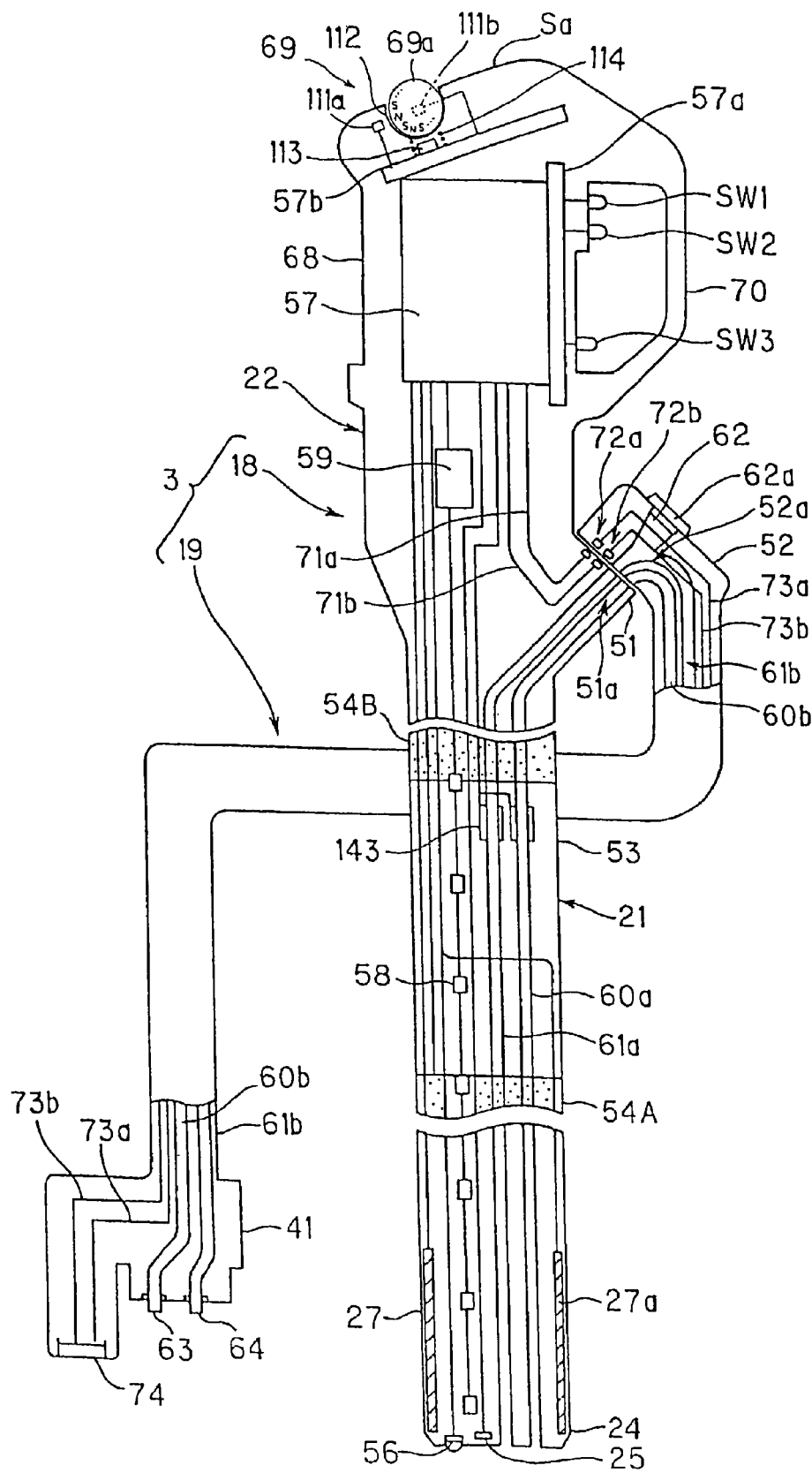
FIG. 7 is a diagram showing an internal configuration of an endoscope of Embodiment 1.

More specifically, diagrammatic structure in the periphery of the track ball 69 is designed as shown in FIG. 7.

The inclined surface Sa at the top end of the operation portion 22 is provided with a substantially semi-globally shaped concave portion. Hole elements 111a and 111b, for example, as magnetic sensors are disposed in two places perpendicularly crossing in the periphery of that concave portion. Detected signals of the respective hole elements 111a and 111b are inputted to the controlling circuit 57 through the track ball substrate 57b.

In addition, that concave portion is covered watertightly with expanding/shrinking waterproof film 112. A global ball 69a is housed from exterior of the concave portion covered by that waterproof film 112. The surface of that ball 69a is structured with the N pole and the S pole being disposed alternately and two-dimensionally.

And a user operates that ball 69a with a finger to rotate so that the rotation of the ball 69a moves magnetic pole on the surface of the ball 69a. The amount in change of magnetic field at that occasion is designed to be detected without contact to the ball 69a at the hole elements 111a and 111b so as to enable detection of the movement direction as well as the movement amount of the ball 69a in the perpendicular two directions.

In addition, a switch 113, for example, is designed to be provided in the track ball substrate 57b adjacent to the concave portion covered watertightly with waterproof film 112 so that a user operates to push or press the ball 69a to the side of the concave portion and thereby the pushed ball 69a switches the contact point of the switch 113 from OFF to ON or from ON to OFF. The switch detecting signal from that switch 113 is also inputted to the controlling circuit 57. Here, a coil spring 114 is disposed in the ball 69a in the circumference of the switch 113. When the operation of pushing the ball 69a is stopped, the ball 69a is returned to the side of the concave portion.

One of characteristics of the present embodiment is to provide such configured track ball 69 so that a user operates the ball 69a to rotate to thereby enable operation of an instruction to the curving portion 27 of carrying out curving in an any direction; and to provide switching means capable of using the switch 113 to be put ON/OFF by pushing operation of the ball 69a as will be described below from a function of operating a curving instruction to another function.

Here, in the above described description, in the case where the N and S magnetic poles are disposed two-dimensionally on the surface of the ball 69a and the ball 69a is rotated to move, there employed is structure of detecting in a magnetic method of detecting changes in the magnetic field at that time with the hole elements 111a and 111b and thereby detecting the movement direction of the ball 69a and the movement amount thereof, but it is also advisable that optical detection is employed as described below.

The ball 69a is provided, on the surface, with a black point (with low reflectivity), for example, two-dimensionally at a predetermined pitch (the other portions are colored white and the like with high reflectivity); two places of the waterproof film 112 in the circumference of the concave portion where the ball 69a is housed are formed by a transparent member; and photoreflectors, for example, as optical sensors are respectively disposed in the interior side of the waterproof film 112.

And it is also advisable that the respective photoreflectors are designed to emit light onto the surface of the ball 69a through the transparent member so as to enable detection of movements in the mutually perpendicular directions; and in the case where the ball 69a is rotated by receiving the reflected light thereof, detection in the perpendicular direction and the movement amount (rotation amount) is detected optically.

Here, it is also advisable that the pressure sensor of detecting pressure instead of the switch 113 is employed to detect pushing operation or pressing operation of the ball 69a by a user. That is, it is also advisable that a comparator compares the outputs of the pressure sensors so that corresponding controlling processing is carried out in the case of detecting pressure exceeding a predetermined value, taking it that switching operation has been carried out.

In addition, a substantially U-shaped hook 70 is provided to link the portions in the vicinity of the both ends, in the longitudinal direction, of the grip portion 68 provided in the vicinity of the rear end of that operation portion 22; and, since hand fingers are inserted inside the hook 70 in order that an operator grasps it with the right hand (or the left hand) as shown in FIG. 8B, the endoscope 3 can be effectively prevented from dropping due to its weight even in the case where the grip portion 68 is not grasped firmly.

That is, even if the endoscope 3 is about to drop due to its weight, the hook 70 hits the hand located below it so that the endoscope 3 can be prevented from dropping. Thus, in the present embodiment, even if an operator does not grasp (retain) the grip portion 68 firmly, the endoscope 3 can be effectively prevented from dropping downward due to its weight. Accordingly, an operator can prevent the endoscope 3 from dropping out and the like to improve operability if he/she inserts a part of his/her hands inside the hook 70 even if he/she gives up grasping (retaining) the grip portion 68 in the case where he/she grasps the grip portion 68 to carry out various kinds of operations and in the case where the hands or fingers grasping it get exhausted with those operations.

In addition, as shown in FIG. 8A to FIG. 8C, the air-feed/water-feed switch SW4 and the suction switch SW5 are disposed axisymmetrically in the both sides of the track ball 69 in that inclined surface Sa.

That track ball 69 and the scope switches SW4 and SW5 are also connected to the controlling circuit 57. Proceeding further with description with reference to FIG. 8A to FIG. 8D, in the front view shown in FIG. 8B, the operation portion 22 or the grip portion 68 are shaped axisymmetrically on a center line O (as a reference line) extending in the longitudinal direction of the operation portion 22 or the grip portion 68; and the track ball 69 is disposed on the inclined surface Sa located on that center line O. And the air-feed/water-feed switch SW4 and the suction switch SW5 are respectively disposed in axisymmetric locations in the both sides of that track ball 69.

In addition, the rear view on the opposite side of that front view will impart FIG. 8C; that rear view also comprises the axisymmetric shape on that center line O so that three scope switches SW 1, SW2 and SW3 are disposed on the exterior surface of the grip portion 68 so as to be disposed along that center line O.

In addition, in the present embodiment, as shown in FIG. 8A, the inclined surface Sa is formed to make an angle φ of an obtuse angle larger than 90° from the center line O of the grip portion 68 or a line in parallel to the side surface thereof. In other words, the inclined surface Sa is formed in a slope to make an angle of θ from a surface perpendicular to the center line O of the grip portion 68 so that the track ball 69, the air-feed/water-feed switch SW4 and the suction switch SW5 are disposed axisymmetrically in the position of the lower portion side in that inclined surface Sa. And as shown in FIG. 8B, the track ball 69 and the like are designed to be operated easily with a thumb of the grasping hand.

As described above, the inclined surface Sa can be well operated if the angle φ making an obtuse angle from the center line O, that is 90° to 180°, and further specifically, as shown in FIG. 8E, in the case of falling within a range from the angle φ1 of 120° to the angle φ2 of 150°, further good operability can be secured.

One of characteristics of the present embodiment is that the operation means (instruction inputting portion) such as the track ball 69 and the like provided in the operation portion 22 are designed to be disposed axisymmetrically on the center line O in the longitudinal direction of the grip portion 68 so that an operator can carry out a grasping operation with any of right hand or left hand.

In addition, the grip portion 68 is provided with a hook 70 being substantially U-shaped to link the substantially both ends of the grip portion 68 in the longitudinal direction, and thereby even in such a state that a operator hypothetically grasps the grip portion 68 insufficiently, an index finger and the like are inserted inside the hook 70; and therefore in the case where the endoscope 3 is about to drop downward due to its weight, the hook 70 is restrained by the index finger and the like, imparting a function efficiently enabling prevention of the endoscope 3 from dropping.

In addition, in the present embodiment, the grip portion 68 is formed in the vicinity of the rear end of the operation portion 22 so as to provide a connecting portion to the tube unit 19 in a location closer to the insertion portion 21 than to the position of that grip portion 68, and therefore, an eccentricity of the location of the center of gravity from the position of the center axis in the case of grasping the grip portion 68 can be reduced.

That is, when the tube unit 19 is extended out toward the side direction more from the position of the rear side (top side) than the position of the grip portion in a prior art, the position of the center of gravity is apt to impart eccentricity with weight due to the tube unit; but since, in the present embodiment, the tube unit 19 will be extended out toward the side direction more from the position of the side of the insertion portion 21, that is, the downward side than the grip portion 68, the amount of eccentricity of the center of gravity can be made small to improve operability.

In addition, also in the endoscope 3 of the present embodiment, the case where an operator (user) such as an operator grasps the grip portion 68 with the left hand or the right hand will impart a case where the inner both sides of the hook 70 will touch that index finger in the vicinity of the side portion, and therefore even if eccentricity takes place on the position of the center of gravity to affect the center axis to get inclined (that is, the longitudinal direction of the operation portion 22 gets inclined), the hook 70 hits the hand so as to be capable of restraining that inclination and of securing good operability.

As shown in FIG. 7, the power supply line 71a and the signal line 71b extended out from the controlling circuit 57 are brought into contactless electric connection to the power supply line 73a and the signal line 73b inserted inside the tube unit 19 through the contactless transmitting portions 72a and 72b formed in the connector portion 51 and the comprehensive connector portion 52. Those of the power supply line 73a and the signal line 73b are connected to power supply & signal terminal forming an electric connector 74 in the scope connector 41.

And, the user connects that scope connector 41 to the AWS unit 4, and thereby the power supply line 73a is connected to the power supply unit 75 through the scope electric connector 43 of the AWS unit 4 as shown in FIG. 6 while the signal line 73b is connected to the UPD unit 76, the transmitting/receiving unit 77 and the AWS controlling unit 66 (through the power supply unit 75). Here, the transmitting/receiving unit 77 is connected to the antenna portion 77a of transmitting/receiving radio waves in a wireless system.

Here, the contactless transmitting portions 72a and 72b are respectively structured to form a transformer of causing a pair of coils to come closer so as to undergo electromagnetic coupling. That is, an end portion of the power supply line 71a is connected to a coil forming a contactless transmitting portion 72a; and an end portion of the other power supply line 73a is connected to a coil adjacent to the coil in the contactless transmitting portion 72a.

And, the alternate power transmitted by the power supplying line 73a is transmitted to the side of the power supply line 71a through the coil of carrying out electromagnetic coupling in the contactless transmitting portion 72a.

In addition, an end portion of the signal line 71b is connected to a coil forming a contactless transmitting portion 72b; and an end portion of the other signal line 73b is connected to a coil adjacent to the coil in the contactless transmitting portion 72b.

Undergoing electromagnetic coupling to form a transformer, signals are transmitted from the side of the signal line 71b to the side of the signal line 73b through the coil to make a pair and the signals are also transmitted to the inverse direction.

Thus, the endoscope 3 of the present embodiment is also characterized in that influence of corrosion and the like taking place in the case of electric contact even if the endoscope main body 18 is configured to be detachably connected to the tube unit 19 contactlessly to repeat cleaning, sterilization and the like.

In addition, as shown in FIG. 7, transparency sensors 143 are provided halfway in the air-feed/water-feed conduit 60a and in the suction conduit 61a respectively and light is transmitted in the respective conduits of the air-feed/water-feed conduit 60a and the suction conduit 61a respectively formed of a transparent tube so as to make a dirt level of the inner wall of the conduits and transparency of the fluid coming through the interior of the conduits detectable.

Figure 10A:
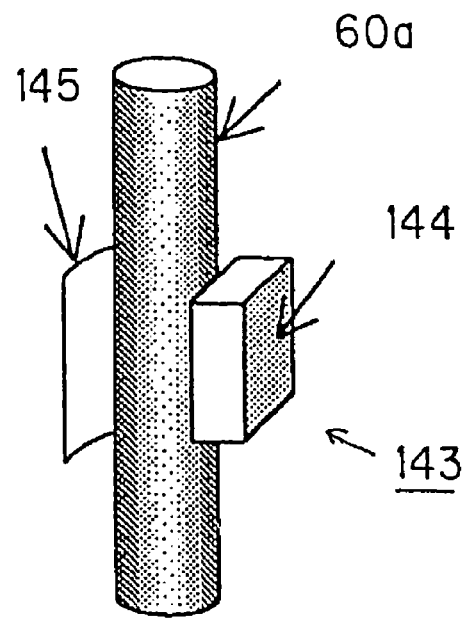
FIG. 10A is a drawing showing a configuration of a transparency sensor.
Figure 10B:
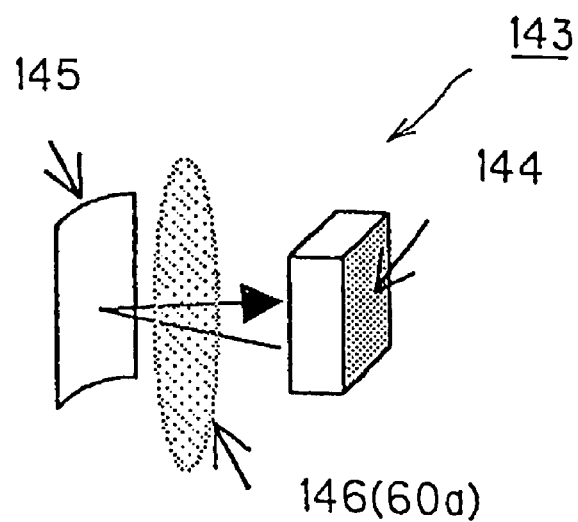
FIG. 10B is a drawing of showing a movement of a transparency sensor.

The transparency sensors 143 are connected to the controlling circuit 57 with signal lines. FIG. 10A and FIG. 10B shows explanatory views of cleaning level detecting action by the transparency sensor 143.

As shown in FIG. 10A, a photoreflector 144 and a reflecting plate 145 are disposed to face each other in the outer circumference of the air-feed/water-feed conduit 60a (also applicable to the suction conduit 61a) formed of the transparent tube to form the transparency sensor 143.

And, as shown in FIG. 10B, light from a light emitting element configuring a photoreflector 144 is emitted to the side of the reflecting plate 145 so that the reflected light reflected by the reflecting plate 145 is received by a light receiving element configuring a photoreflector 144.

In that case, actually, a transmission detecting member 146 such as an air-feed/water-feed conduit 60a and the like formed of a transparent tube is disposed between the photoreflector 144 and the reflecting plate 145; and therefore in the case of causing transparent cleaning liquid to flow inside the air-feed/water-feed conduit 60a to clean the inner wall side of the air-feed/water-feed conduit 60a, the inner wall surface will impart a clean state, then the light amount received by the light receiving element of the photoreflector 144 is increased and thereby a cleaning level is designed to be detected.

Accordingly, this function enables quantitative detection of the cleaning level of the inner wall surface of the air-feed/water-feed conduit 60a and the inner wall surface of the suction conduit 61a.

Here, that case was described with action in the case of cleaning with cleaning liquid, but with reference to detection outputs of the transparency sensor 143 during endoscope inspection and the like, a dirt level of the inner wall of the air-feed/water-feed conduit 60a and the inner wall of the suction conduit 61a can be known.

Figure 11:
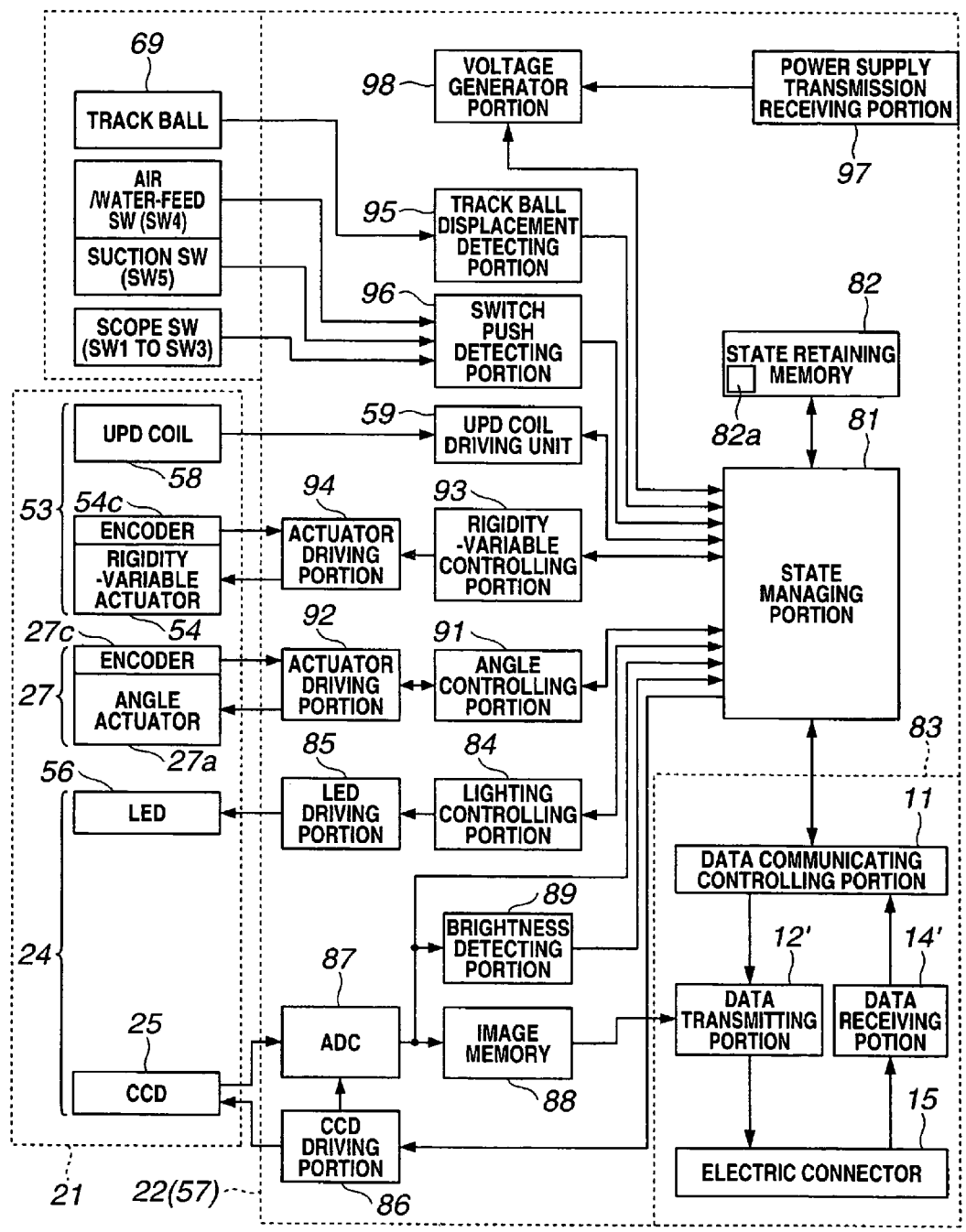
FIG. 11 is a block diagram showing a configuration of the electrical system in an endoscope.

FIG. 11 shows a configuration in an electric system in a controlling circuit 57 and the like disposed inside an operation portion 22 of the endoscope main body 18 and main components disposed in respective portions of an insertion portion 21.

A CCD 25 and an LED 56 are disposed at the tip portion 24 of the insertion portion 21 shown in the lower portion on the left side in FIG. 11; an angle actuator (specifically EPAM in the present embodiment) 27a and an encoder 27c are disposed in a curving portion 27 described thereabove in the drawing; and a rigidity-variable actuator (specifically EPAM in the present embodiment) 54 and an encoder 54c are disposed in a flexible portion 53 described thereabove in the drawing. In addition, a transparency sensor 143 and a UPD coil 58 are disposed in that flexible portion 53.

In addition, a track ball 69, an air-feed/water-feed SW (SW4), a suction SW (SW5) and scope SWs (SW1 to SW3) are disposed on the surface of the operation portion 22 described above the flexible portion 53 of the insertion portion 21. Here, as will be described below, the track ball 69 is operated to allocate functions of selecting/setting an angle operation and the other functions.

As shown in the left side of FIG. 11, they are connected to the controlling circuit 57 (except a UPD coil driving unit 59 and the like, however) including almost the interior of the operation portion 22 in its entirety shown in the right side thereof through the signal line so that the controlling circuit 57 carries out driving control of those functions, signal processing and the like.

The controlling circuit 57 has a state managing portion 81 configured by a CPU and the like of managing the controlling state; and that state managing portion 81 is connected to state retaining memory 82 of retaining (storing) states of respective portions. That state retaining memory 82 has program storing memory 82a as controlling information storing means; program data as controlling information stored in that program storing memory 82a are rewritten; and thereby also in the case of changing components shown in FIG. 11, (the CPU configuring) the state managing portion 81 is designed to be capable of controlling (managing) corresponding with those changed configurations.

In addition, that state retaining memory 82 or at least the program retaining memory 82a is configured by nonvolatile and electrically rewritable flash memory or EEPROM and the like, for example, so that the program data can be changed simply through the state managing portion 81.

A program data changing command is sent to the state managing portion 81 through a signal line 71b, for example, that is, a transmitting/receiving unit 83 in a wired system described below; program data to be rewritten subject to that command are transmitted from the side of the AWS unit 4; and thereby the program data are designed to be changeable. In addition, version up and the like are designed to be carried out easily through the signal line 71b.

In addition, it is also advisable that device type information inherent to respective endoscopes 3 as described below and individual information corresponding with states of use is written in that state retaining memory 82 to enable effective utilization of that information. Specifically, the state retaining memory 82 retains device type information of the endoscope 3, for example, (information such as kinds of CCD 25 and length of insertion portion, for example); individual information of respective endoscopes 3, which are different in use state such as endoscope inspection and the like, (information such as use period (lifetime or accumulated use period of endoscope inspection), times of cleaning, adjusted values, maintenance history and the like, for example) is retrained; and those pieces of information are utilized for determining system operations, providing information to users and the like.

In addition, those pieces of information are made editable with an endoscope system controlling apparatus 5, a cleaning apparatus not shown in the drawing and the like from outside.

Being designed like that, the state retaining memory 82 gets in charge of a function of prior art scope ID and is shared and utilized and thereby information (data) to be retained in the scope ID can be exploited efficiently.

In addition, since that state retaining memory 82 is present, there is no need to provide the scope ID separately so that performance higher than in the existing scope ID can be achieved and it will become possible to carry out suitable setting, adjustment, management, processing and the like in further detail.

As described above, the state managing portion 81 is connected to a transmitting/receiving unit 83 in a wired system of carrying out wired communication with the AWS unit 4.

In addition, through a lighting controlling portion 84 of controlling lighting, that state managing portion 81 controls an LED driving portion 85 controlled by that lighting controlling portion 84. That LED driving portion 85 applies LED driving signals of causing the LED 56, which will become lighting means, to emit light.

Due to emission of light from that LED 56, by an object lens not shown in the drawing mounted on the observation window a subject such as a discussed part illuminated forms images onto the image capturing surface of the CCD 25 disposed in that image forming position and that CCD 25 carries out photoelectric conversion.

Subject to application of CCD driving signals from the CCD driving portion 86 controlled by the state managing portion 81, that CCD 25 outputs, as image capturing signals, the accumulated signal charges subject to photoelectric conversion. Those image capturing signals are converted from analog signals to digital signals with an A/D converter (to be abbreviated as ADC) 87 and thereafter are inputted to the state managing portion 81 and the digital signals (image data) are stored in the image memory 88. The image data in that image memory 88 are sent to the data transmitting portion 12' of the transmitting/receiving unit 83.

And, the data are transmitted from the electric connector 15 to the side of the AWS unit 4 through the signal line 73b inside the tube unit 19. Moreover, the data are transmitted to the endoscope system controlling apparatus 5 from the AWS unit 4 in a wireless system.

As shown in FIG. 6, the image data transmitted to the endoscope system controlling apparatus 5 are received by the transmitting/receiving unit 101 in a wireless system; video signals are generated subject to image processing by the image processing unit 116; and the video signals are outputted from the monitor connector 35 to the observation monitor 6 through the system controlling unit 117 of controlling the endoscope system 1 in its entirety so that an endoscope image is displayed on a display screen of the observation monitor 6. Here, in FIG. 6, the power supply unit 100 supplies electric power to the transmitting/receiving unit 101, the image processing unit 116 and the system controlling unit 117.

As shown in FIG. 11, output signals of the above described ADC 87 are sent to a brightness detecting portion 89 and the information on brightness of images detected by the brightness detecting portion 89 is sent to the state managing portion 81. The state managing portion 81 controls light adjustment with this information through the lighting controlling portion 84 so that the light amount of lighting by the LED 56 reaches adequate brightness.

In addition, the state managing portion 81 controls the actuator driving portion 92 through the angle controlling portion 91 to control to drive the angle actuator (EPAM) 27a with that actuator driving portion 92. Here the amount of driving that angle actuator (EPAM) 27a is detected by the encoder 27c and the driving amount is controlled so as to match a value corresponding with the designated value.

In addition, the state managing portion 81 controls the actuator driving portion 94 through the rigidity-variable controlling portion 93 while that actuator driving portion 94 controls to drive the rigidity-variable actuator (EPAM) 54 (here only one of 54A and 54B is shown to represent them). Here, the amount of driving of that rigidity-variable actuator (EPAM) 54 is detected by the encoder 54c so that the driving amount thereof is controlled so as to reach a value corresponding with the designated value.

In addition, the detected signals from the transparency sensor 143 provided inside the flexible portion 53 are converted into signal data corresponding with transparency by the transparency detecting portion 148 and thereafter are inputted to the state managing portion 81; the state managing portion 81 carries out comparison with a reference value of transparency stored in the state retaining memory 82 and the like in advance and transmits that information, in the case of agreement with that reference value, from the transmitting/receiving unit 83 to the endoscope system controlling apparatus 5 through the AWS unit 4 to display on the observation monitor 6 that the agreement with the reference value has taken place.

In addition, an input to that state managing portion 81 is carried out through a track ball displacement detecting portion 95 corresponding with the operation amount from the track ball 69 and the like provided in the operation portion 22.

That track ball displacement detecting portion 95 has hole elements 111a and 111b of detecting rotation direction as well as rotation amount of the ball 69a of the track ball 69 and detects ON/OFF of the switch 113.

In addition, operation of switch pushing such as ON and the like by the air-feed/water-feed SW, the suction SW and the scope SW is detected by switch push detecting portion 96 and the detected information thereof is inputted to the state managing portion 81.

In addition, the controlling circuit 57 has a power supply transmission receiving portion 97 and a voltage generator portion 98. The power supply transmission receiving portion 97 is, specifically, a contactless transmitting unit 51b in the operation portion 22 and an electric connector 74 at the terminal end of the tube unit 19. And, the electric power transmitted by the voltage generator portion 98 is converted into direct voltage in the voltage generator portion 98. Power supply generated by the voltage generator portion 98 supplies respective portions inside the controlling circuit 57 with electric power required for action thereof.

Figure 12A:
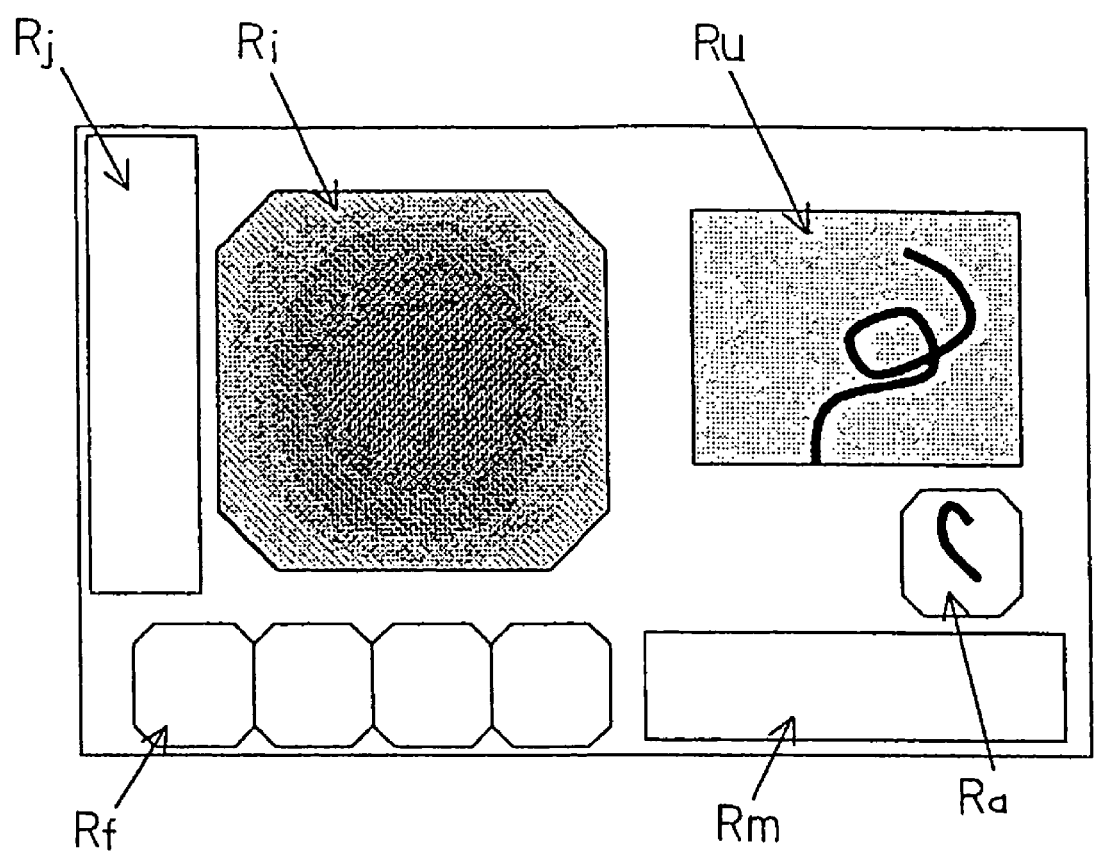
FIG. 12A is a diagram exemplifying display of an endoscope image and the like on a monitor.

In the case where the endoscope system 1 comprising the present embodiment takes in the power supply, the observation monitor 6 displays various kinds of images, for example, as in FIG. 12A. In that case, a information displaying region Rj of displaying patient information and the like; an endoscope image displaying region Ri; a UPD image displaying region Ru; a freeze image displaying region Rf; an angle-shaped displaying region Ra; and otherwise a menu displaying region Rm are provided. A menu is displayed in that menu displaying region Rm.

Figure 12B:
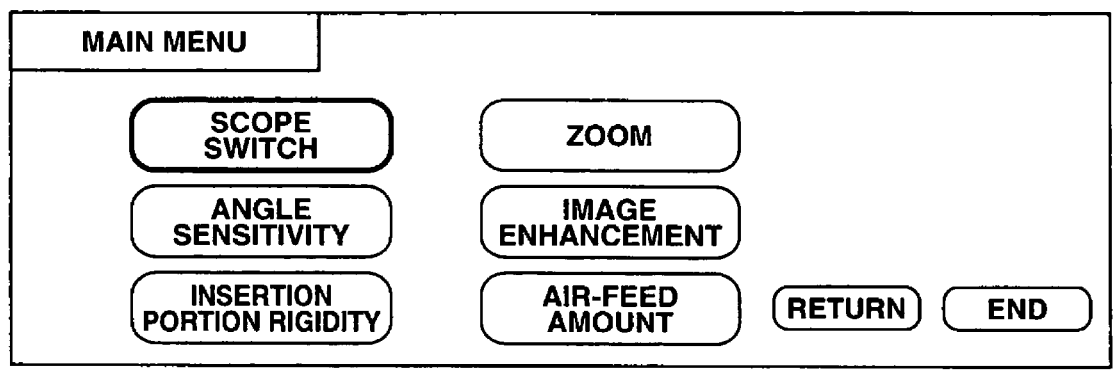
FIG. 12B is a drawing exemplifying a main menu on a monitor.

As a menu displayed in the menu displaying region Rm, the main menu shown in FIG. 12B is displayed. That main menu displays a scope switch, angle sensitivity, insertion portion rigidity, zoom, image enhancement, an air-feed amount, and moreover, a return item of carrying out operation instruction to bring the preceding menu window back and an ending item of carrying out operation instruction of ending the menu.

And a user can cause the selection frame or the cursor to move by rotating operation in the vertical direction or in the horizontal direction of the track ball 69; and for example, movement to a scope switch item will lead to thick display of the frame to show current selection.

Figure 12C:
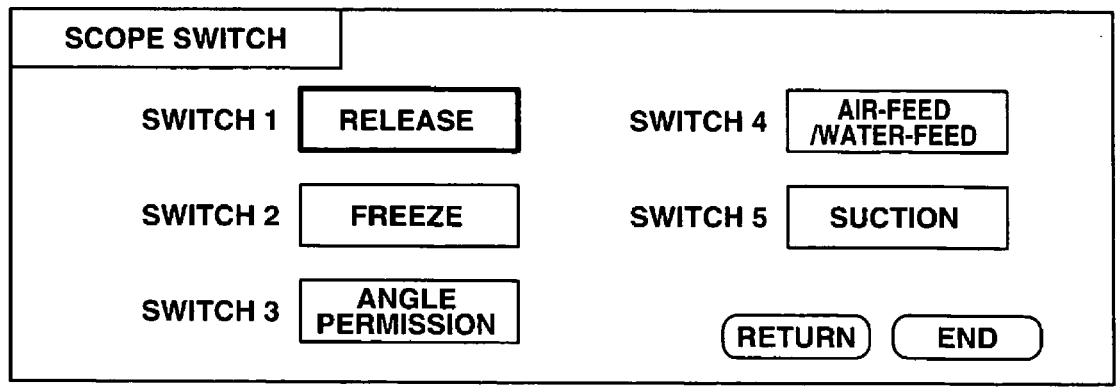
FIG. 12C is a drawing exemplifying allocation of functions to function switch on a monitor.

Moreover, determining operation is implemented by pushing one scope switch (for example) SW4 disposed on the both sides of the track ball 69, and thereby as shown in FIG. 12C, it is designed to be possible to select/set a function of allocating five scope switches SW1 to SW5.

In addition, in the case of desiring to change and set, for example, an air-feed amount, it is advisable to select/set the item of the air-feed amount. In that case, an operation of the track ball 69 enables instructing operation of increasing and decreasing in air-feed amount. Thus, it is hardly simple to implement an instructing operation of increasing and decreasing in air-feed amount simply in the case of an ordinary ON/OFF switch. But it is possible to cause instructing signals of increasing in air-feed amount to occur by rotating the track ball 69 upward, for example, in the present embodiment while it is possible to cause instructing signals of decreasing in air-feed amount to occur by rotating the track ball 69 downward and thus it is possible to improve operability for a user by a large margin.

In addition, it is also possible to simply implement instructing operation of increasing and decreasing in angle sensitivity by rotating operation of the track ball 69 also on angle sensitivity item (selection item) shown in FIG. 12B. In addition, also in the case of image enhancement and the like, it is possible to implement likewise appropriate instructing operation.

Thus in the present embodiment, the track ball 69 has a function of implementing an instructing operation (instructive inputting) of causing the curving portion 27 to curve in a desired direction and a function different from the curving operation, more specifically, an operation of allocating functions to scope switches SW1 to SW5 provided in the circumference portion of the grip portion 68 and the like are made feasible to improve operability.

That is, also in the prior art, the function of allocation on a plurality of scope switches provided in the circumference of the operation portion can be occasionally changed in setting, but those cases still used to require an operation on the signal processing apparatus side such as a video processor to which an endoscope is connected, and therefore, presence of defects with low operability has been made improvable.

In addition, in the present embodiment, instructing operation with the track ball 69 as described above makes it possible to carry out instruction operating function which used to be deemed difficult for an operation (instructing operation) with the scope switches SW1 to SW5 of simply switching ON/OFF.

Next, operations of the endoscope system 1 according to such a configuration will be described.

As prior preparation for carrying out endoscope inspection, at first a comprehensive connector portion 52 of the tube unit 19 of a dispo type is connected to the connector portion 51 of the operation portion 22 of the endoscope main body 18. In that case, the contactless transmitting portions 72a and 72b will be mutually brought into connection in an insulated and waterproof state. That connection completes preparation of the endoscope 3.

Next, the scope connector 41 of the tube unit 19 is connected to the connector 40 of the AWS unit 4. Employing one-touch connection to this part, a single connecting operation completes connection with respective types of conduit, power supply line, signal line and light. There is no need to implement connection of respective conduits, connection of electric connector and the like each time respectively as in conventional endoscope system.

In addition, a user connects a UPD coil unit 8 to the AWS unit 4 and connects the endoscope system controlling apparatus 5 to the observation monitor 6. In addition, complying with necessity, the endoscope system controlling apparatus 5 is connected to the image recording unit 7 and the like, thereby completing set-up of the endoscope system 1.

Next, the power supplies of the AWS unit 4 and the endoscope system controlling apparatus 5 are put ON. Then, the respective portions inside the AWS unit 4 reaches operating states while the power supply unit 75 will reach a state of being capable of supplying electric power to the side of the endoscope 3 through the power supply line.

In that case, the AWS unit 4 puts OFF the supply of electric power at first to start up a timer, and supplies electric power continuously after confirming that the signal is correctly returned from the side of the endoscope 3 within a constant time.

And, an operator inserts the insertion portion 21 of that endoscope 3 to inside the body cavity of a patient and thereby the shooting subjects such as affected area inside the body cavity undergo image capturing with a CCD 25 provided in the tip portion 24 of the insertion portion 21. The image-captured image data are transmitted wirelessly to the endoscope system controlling apparatus 5 through the AWS unit 4 so as to undergo image processing and generate video signals. Thereby images of the image-capturing subject are displayed as endoscope images on the display screen of the observation monitor 6. Accordingly, the operator observes those endoscope images and thereby diagnoses on the affected areas and the like and it is also possible to implement treatment for therapy in use of treatment tools in accordance with necessity.

In the endoscope 3 of the present embodiment, as shown in FIG. 8, a track ball 69 having a function of angle instruction inputting portion, scope switches SW 1 to SW3 of implementing respective types of operating instructions such as freeze instructing operation, an air-feed/water-feed switch (SW4) and a suction switch (SW5) are disposed axisymmetrically to the center line O in the longitudinal direction of the grip portion 68.

Accordingly, in the case where an operator grasps the grip portion 68 of the operation portion 22 with his/her right hand as shown in FIG. 8B, the track ball 69 is located in an operation-friendly location for a thumb, and the air-feed/water-feed switch (SW4) and the suction switch (SW5) disposed axisymmetrically on the both sides thereof can be simply operated as well.

In addition, in the case of grasp, the scope switches SW1 and SW2 are located respectively in the vicinity of the location where the index finger and the middle finger grasp while the scope switch SW3 is located in the vicinity where a little finger participates in grasping.

Accordingly, an operator can carry out respective types of operations under good operability with the grasping right hand.

In addition, also in the case of an operator who grasps with his/her left hand, the gripping position in the outer circumference where the grip portion 68 is grasped will come to the side portion side facing the side portion grasped by the right hand, but the positions of respective fingers will be likewise in the case of grasping with the left hand with regard to the instruction inputting portion.

That is, in the case where an operator grasps the grip portion 68 of the operation portion 22 with his/her left hand, the track ball 69 is located in an operation-friendly location for a thumb, and the air-feed/water-feed switch (SW4) and the suction switch (SW5) disposed axisymmetrically on the both sides thereof can be simply operated as well.

In addition, in the case of grasp, the scope switches SW1 and SW2 are located respectively in the vicinity of the location where the index finger and the middle finger grasp while the scope switch SW3 is located in the vicinity where a little finger participates in grasping.

Accordingly, an operator can carry out respective types of operations under good operability with the grasping left hand.

In addition, as described above, in the present embodiment, the both ends, in the longitudinal direction, of the grip portion 68 are linked; and, there provided is a hook 70 in the interior side of which the grasping hand will be inserted through; and therefore the endoscope 3 can be effectively prevented from dropping due to its weight even in the case where the grip portion 68 is not grasped firmly.

In addition, in the present embodiment, as shown in FIG. 12, it is also possible to change and set allocation of function for the scope switch SW1 to the scope switch SW5. Accordingly, the respective operators change and set allocation of functions for the scope switches SW 1 to SW5 in a most operation-friendly fashion to carry out endoscope inspection.

In addition, by allocating to the track ball 69 functions different from the angle operation, a user can also carry out various types of operations in such a state that a user desires in a state with a user grasping the endoscope 3.

For example, in FIG. 12B, by selecting air-feed amount item, for example, it is possible to change air-feed amount easily. Therefore, it is also possible to simplify configuration of implementing air-feed instruction.

Next with reference to FIG. 13, processing of angle operating control will be described. When angle control processing starts, as shown in Step S41, the state managing portion 81 determines whether angle control is effective or not.

In the present embodiment, on the track ball 69, the state managing portion 81 determines, as shown in Step S41, whether angle control is effective or not, based on whether or not that track ball 69 is being pressed. Specifically, the state managing portion 81 can detect a displacement operation with rotation operation of the track ball 69 and a pushing or pressing operation with an output of the track ball displacement detecting portion 95. Here, when the track ball 69 is being pressed, the angle control is put OFF.

The state managing portion 81 determines whether the angle control is effective or not with outputs of the track ball displacement detecting portion 95.

And in the case of determination that the angle control is not effective, the step moves to Step S45 and retains the preceding command value. On the other hand, in the case of determination that the angle control is effective, the step goes forward to the next Step S42 and then the state managing portion 81 obtains the state data thereof derived by operation of the track ball 69. And, in the next Step S43, the state managing portion 81 further determines whether a state change is present or not with outputs of the track ball displacement detecting portion 95.

In that case, in the case of determination that no state change is present, the state managing portion 81 moves to Step S45 and on the contrary in the case of determination that a state change is present, next Step S44 calculates a command value corresponding with the rotation direction and the rotation amount of the track ball 69.

After processing of Step S44 or S45, the state managing portion 81 sends, as shown in Step S46, the command value to the actuator driving portion 92 through the angle controlling portion 91 and implements servo processing on the angle actuator.

That is, based on the command value, the actuator driving portion 92 drives the angle actuator so as to reach the angle state (curving angle and curving direction) corresponding with the command value thereof. At that occasion, detecting the angle state of the angle actuator with an encoder (Step S47), the actuator driving portion 92 drives the angle actuator so that the value detected by that encoder matches the target angle state corresponding with the command value. Thus, the target angle state is derived, and then the angle control processing is over.

In addition, in the present embodiment, as shown in FIG. 12A, the display screen of the observation monitor 6 is provided with a angle-shaped display region Ra, and the angle state (curved state) on the tip side of the endoscope 3 is three-dimensionally displayed in that display region Ra to thereby make it easier for an operator to understand the angle state on the tip side of the endoscope 3.

An operation of processing of thus displaying the angle state (curved state) on the tip side of the endoscope 3 three-dimensionally will be described below with reference to FIG. 14 and the like.

Figure 13:
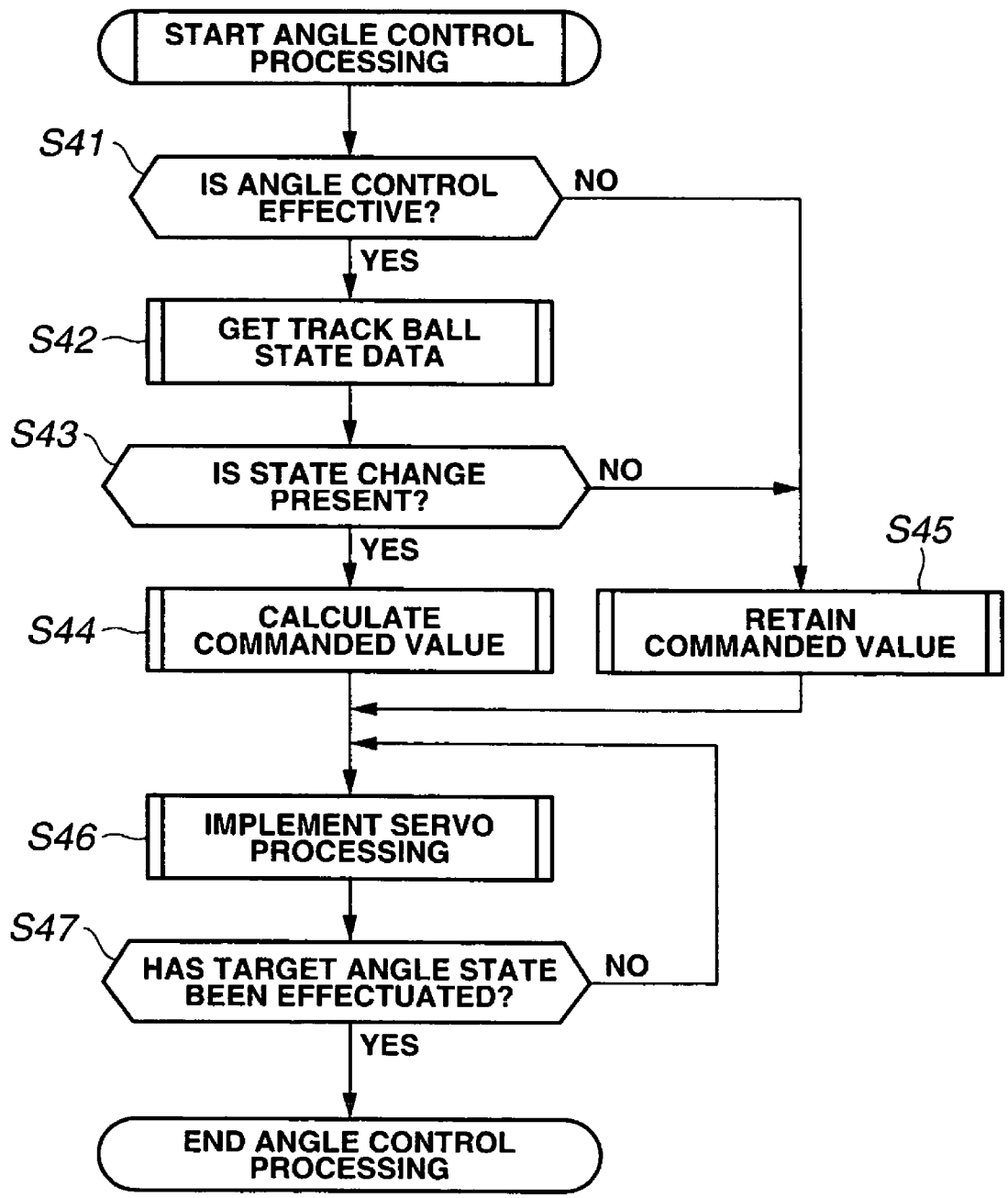
FIG. 13 is a flow chart showing a control processing with regard to an angle operation.
Figure 14:
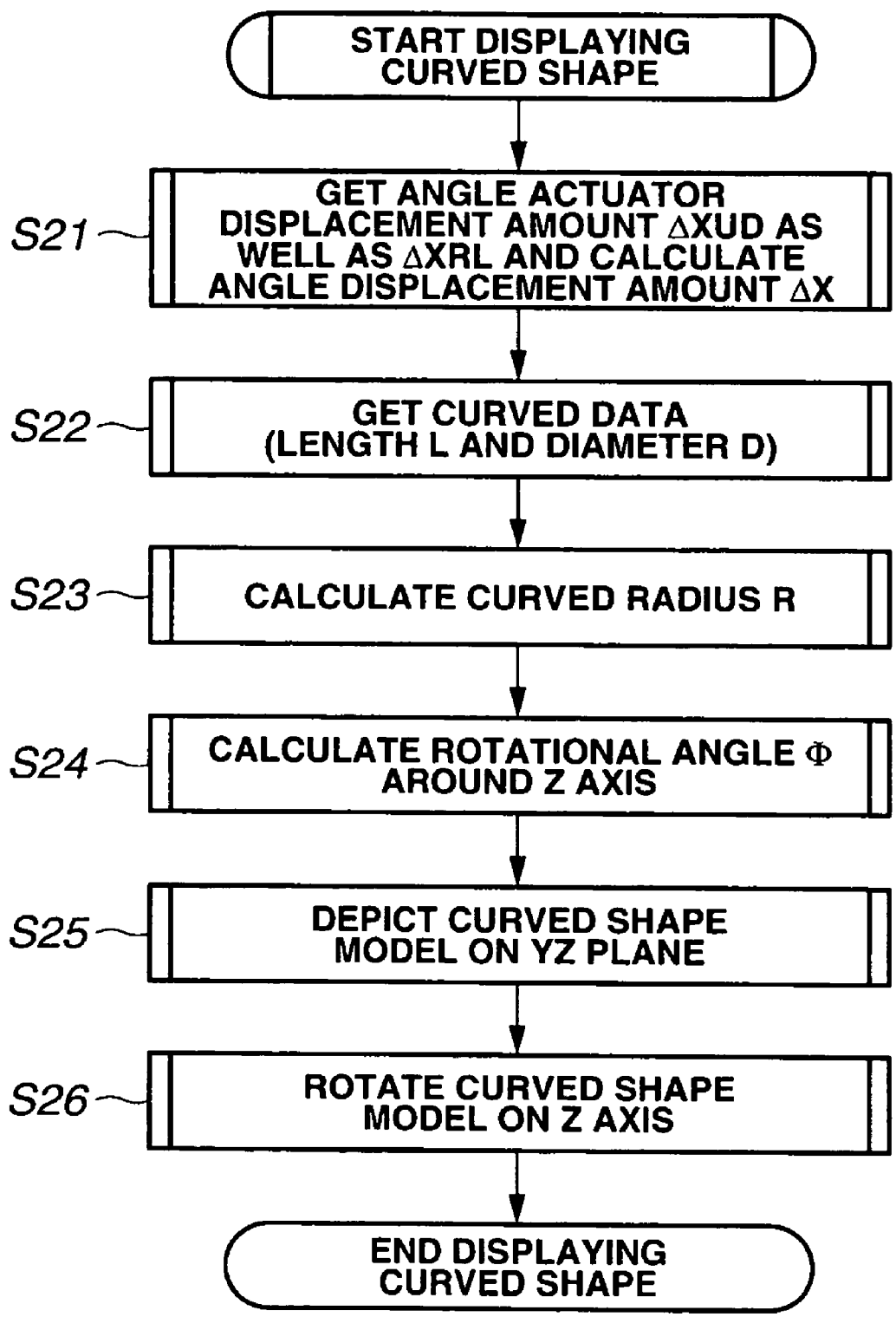
FIG. 14 is a flow chart showing a curved shape display processing.

As shown in FIG. 13, the angle control processing starts and the angle control is set effectively, the state managing portion 81 takes in, as shown in Step S21 in FIG. 14, data of displacement $\Delta Xud$ and $\Delta Xr1$ of the angle actuator 27a in the vertical direction and in the horizontal direction from the encoder 27c through the actuator driving portion 92 and the angle controlling portion 93.

Figure 15:
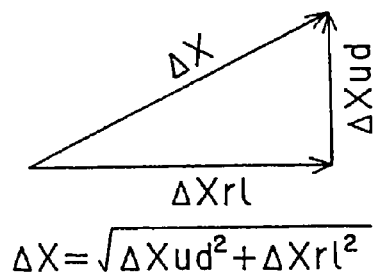
FIG. 15 is a drawing showing relation between the volume of displacement in the vertical direction and in the horizontal direction and the total displacement.

In addition, as shown in FIG. 15, the displacement $\Delta Xud$ and $\Delta Xr1$ is respectively squared and added so as to calculate a square root of the added value and thereby the total displacement $\Delta X$ of the angle actuator 27a is calculated.

In next Step S22, the state managing portion 81 reads and obtains the curving portion data of the endoscope 3 with this state managing portion 81, which is built-in, (specifically, length L and diameter D of the curving portion 27 in the insertion portion 21) from the state retaining memory 82.

Figure 16:
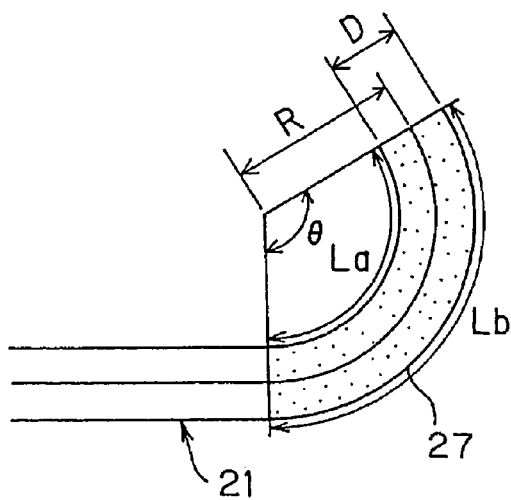
FIG. 16 is an explanatory diagram showing radiuses of curves in a state where a curving portion has been curved.

And, in next Step S23, the state managing portion 81 calculates the curving radius R. In that case, in the case where the curving portion 27 is curved, as shown in FIG. 16, the curving portion 27 can be approximated to curve in a substantially circular arc shape and length La of the curving portion 27 to become the interior side of the curving portion and length Lb of the curving portion 27 to become exterior side are respectively calculated as follows, in consideration of temporary shrinkage of $\Delta X$ on the inner side from the length L along the center and temporary elongation of $\Delta X$ on the outer side respectively, $$La = L - \Delta X = \theta \cdot (R - D/2)$$

$$Lb = L + \Delta X = \theta \cdot (R + D/2)$$

Here, $\theta$ denotes a center angle heading for the circular arc with curving radius R in the case of taking the curving portion 27 to be a circular arc. That is, the circular shaped curving portion 27 can be approximated to have curving radius R and to be present on that center angle $\theta$.

From those formulas (specifically, $L = \theta \cdot R$), the state managing portion 81 uses, as shown in Step S23, the following formula on the center angle $\theta$, $$\theta = 2 \cdot \Delta X / D$$

and thereby, calculates the curving radius R with the following formula, $$R = L \cdot D / (2 \cdot X).$$

Figure 17:
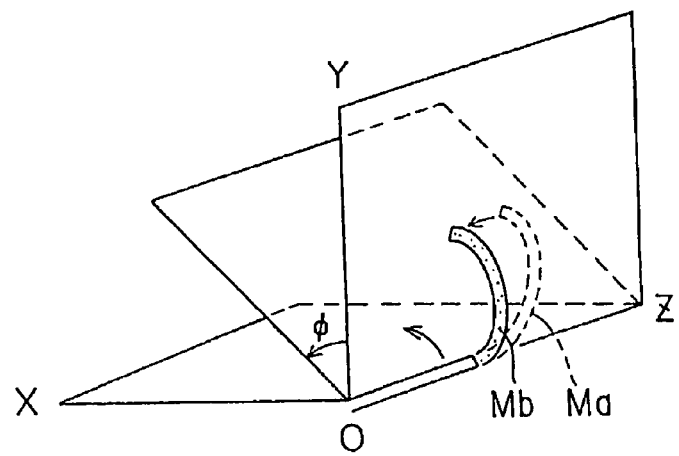
FIG. 17 is an explanatory view depicting three-dimensionally a curved shape of a curving portion.

FIG. 16 shows a case where the curving portion 27 has been made to bend in form of a plane including the inner side and the outer side of the curving. In the case of displaying a curved state of the curving portion 27 on the tip side of the insertion portion 21, the curve-shaped model is displayed three-dimensionally by setting the base end side of the curving portion 27 to the Z axis at the time of displaying, for example, as shown in FIG. 17.

In that case, for example, the curving in the vertical direction is set to the YZ plane so as to relate that YZ plane to the display screen of the observation monitor 6. In addition, depiction is carried out so as to display the curve-shaped model depicted on that YZ plane as if rotation around the Z axis as shown in FIG. 17 took place only by the angle $\phi$ equivalent to the displacement $\Delta Xr1$ component in the horizontal direction.

In order to implement such display, in Step S24 shown in FIG. 14, the state managing portion 81 calculates the rotation angle 4 around the Z axis. That rotation angle φ will be:

$$\phi = (\pi/2) \cdot (1 - \Delta Xud/(\Delta Xud + \Delta Xr1))$$

In next Step S25, the state managing portion 81 depicts the curve-shaped model at first on the YZ plane. That is, the curve-shaped model Ma shown in dotted lines in FIG. 17 is at first set onto the YZ plane and depicted.

And, in next Step S26, the state managing portion 81 rotates the curve-shaped model Ma shown in dotted lines only by rotation angle φ around the Z axis. That is, a curve-shaped model Mb indicated in full lines is depicted three-dimensionally so as to dispose that curve-shaped model Ma on a plane subject to rotation only by a rotation angle φ around the Z axis. And, that processing of display of curved shape is over.

By displaying the curving portion 27 in the vicinity of the tip side of the insertion portion 21 as a curve-shaped model Mb, the curved state on the tip side of the insertion portion 21 will be understood easily so that diagnosis and the like will become easy to implement.

Next, with reference to FIG. 18, control processing of rigidity-variable operation will be described.

When control processing on a rigidity-variable operation starts, the state managing portion 81 determines, as shown in Step S51, whether the rigidity-variable control is effective or not.

Specifically, as having been shown in FIG. 12B, the main menu has allocated the insertion portion rigidity to the scope switches SW1 to SW5 and the state managing portion 81 determines whether the scope switch of the insertion portion rigidity is pushed and made effective or not.

And, in the case where the state managing portion 81 determines that the rigidity-variable control is not effective, the step moves to Step S55 to retain the preceding command value. On the other hand, in the case of determination that the rigidity-variable control is effective, the step goes forward to next Step S52, the state managing portion 81 obtains state data thereof by operations of the track ball 69. That is, in this case, switched from the function of the angle instructing operation, the track ball 69 is used for the instruction function of changing rigidity and the state managing portion 81 obtains the state data thereof derived by an operation of that track ball 69.

In that case, the track ball 69 is disposed in an operation-friendly position, a user will be able to give an instruction to change rigidity in a good state of operability.

And in next Step S53, the state managing portion 81 further determines whether the state change is present or not based on outputs of the track ball displacement detecting portion 95.

In that case, in the case of determination that no state change is present, the state managing portion 81 moves to Step S55 and, in contrast, in the case of determination that a state change is present, command value corresponding with rotation direction and rotation amount of the track ball 69 is calculated in next Step S54.

After processing of Step S54 or S55, the state managing portion 81 sends, as shown in Step S56, the command value to the actuator driving portion 94 through the rigidity-variable controlling portion 93 and implements servo processing on the rigidity-variable actuator 54A or 54B.

That is, based on the command value, the actuator driving portion 94 drives the rigidity-variable actuator 54A or 54B so as to derive the target rigidity corresponding with the command value thereof. In that case, a rigidity-variable state of the rigidity-variable actuator 54A or 54B is detected by the encoder 54c; the actuator driving portion 94 drives the rigidity-variable actuator 54A or 54B so that the value detected by that encoder 54c reaches a target rigidity.

In Step S57 where such servo processing will be going on, the rigidity-variable controlling portion 93 or the state managing portion 81 determines with the actuator driving portion 94 whether the rigidity-variable actuator 54A or 54B is in variable range or not; and in the case of departure from that variable range, that rigidity-variable control processing is over.

In addition, in Step S57, in the case where the rigidity-variable actuator 54A or 54B is within a variable range, further in next Step S58, the rigidity-variable controlling portion 93 or the state managing portion 81 determines whether the target rigidity has been derived or not; and in the case where the target rigidity has not yet derived, the step returns to Step S56 to continue the servo processing. Thus, in the case of reaching the target rigidity, rigidity-variable control processing is over.

In addition, the UPD unit 76 detects, with the UPD coil unit 8, the position of the UPD coil 58 disposed inside the insertion portion 21 of the endoscope 3, calculates an inserting shape of the insertion portion 21 and displays the insertion portion shape, that is, a UPD image, on the display screen of the observation monitor 6.

Next, contents of processing on the side of the endoscope 3 of a human interface realizing a remocon operation by a user and on the side of the endoscope system controlling apparatus 5 will be described with reference to FIG. 19 and FIG. 20. Here, in FIG. 19 and FIG. 20, a human interface is abbreviated as HMI.

Figure 19:
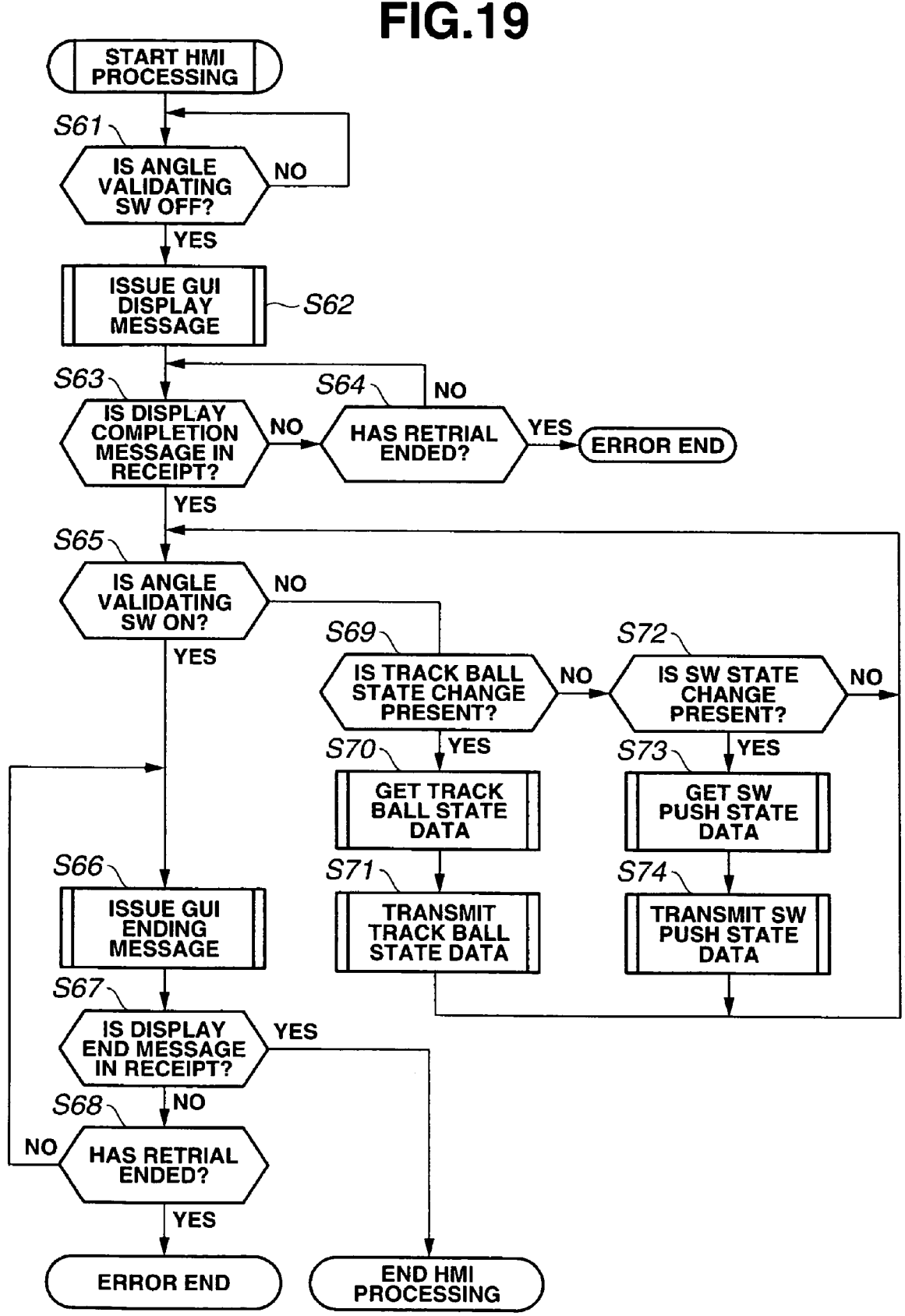
FIG. 19 is a flow chart showing contents of processing at the endoscope side in a human interface.

As shown in FIG. 19, when the processing of the human interface starts, the state managing portion 81 will wait until the angle effective switch is put OFF. That is, it will wait until the track ball 69 is pressed and the angle effective switch is put OFF.

And, when the angle effective switch is put OFF, the state managing portion 81 issues, as shown in next Step S62, GUI (Graphical User Interface) display message. That GUI display message is sent wirelessly to (control CPU) inside the system controlling unit 117 of the endoscope system controlling apparatus 5 from the endoscope 3 through the AWS unit 4.

After issuing the GUI display message, the state managing portion 81 will enter, in next Step S63, a state of waiting for reception of display completion message of GUI from the side of the endoscope system controlling apparatus 5. And, in the case of receiving none of that GUI display completion message, the state managing portion 81 goes forward to Step S64 to determine whether or not the conditions of retrial finalization are applicable, and in the case where no retrial finalization conditions are applicable, goes back to Step S63 and on the contrary in the case where the retrial finalization conditions are applicable, adopts an error end.

In the processing in Step S63, in receipt of the display completion message, the state managing portion 81 moves to Step S65 to determine whether or not the angle effective switch is put ON. And, in the case where the angle effective switch is put ON, the state managing portion 81 issues GUI completion message as shown in Step S66.

Likewise the case of the GUI display message, that GUI completion message is transmitted wirelessly to the endoscope system controlling apparatus 5 from the endoscope 3 through the AWS unit 4. And, after issuing the GUI completion message, the state managing portion 81 will enter, in next Step S67, a state of waiting for reception of display completion message of GUI from the side of the endoscope system controlling apparatus 5. And, in reception of that GUI display completion message, the state managing portion 81 finalizes that human interface processing.

On the other hand, in the case of receiving none of that GUI display completion message, the state managing portion 81 goes forward to Step S68 to determine whether or not the conditions of retrial finalization are applicable, and in the case where no retrial finalization conditions are applicable, goes back to Step S66 and on the contrary in the case where the retrial finalization conditions are applicable, adopts an error end.

And in Step S65, in the case where the angle effective switch is not put ON, the step moves to the processing with the menu window on the side of Step S69. In that Step S69, the state managing portion 81 determines whether or not any change in the state of the track ball 69 is present based on whether any displacement in excess of a certain threshold value is present or not based on the outputs of the track ball displacement detecting portion 95.

And, as shown in Step S70, the state managing portion 81 obtains state data (change data) of the track ball 69 in the case of determination that a change in state of that track ball 69 is present.

In that case, a user can select and instruct a function of the desired item with a cursor moving corresponding with operations of the track ball 69 on the main menu window in FIG. 12B. The state managing portion 81 also implements the processing of displaying the cursor.

And, as shown in Step S71, the state managing portion 81 transmits state data corresponding with operations of the track ball 69 by the user. Those state data are transmitted from the endoscope 3 to the endoscope system controlling apparatus 5 through the AWS unit 4 as packet data in synchronization with the image-captured data of the CCD 25. After transmission of those state data, the step goes back to the processing of Step S65.

In Step S69, in the case of determination that no change in state of the track ball 69 is present, the state managing portion 81 determines, as shown in Step S72, whether or not any change in switch state (switches SW1 to SW5) is present based on the detection outputs from the switch push detecting portion 96.

In that Step S72, in the case of determination that no change in switch state is present, the step goes back to Step S65, and on the contrary in the case of determination that any change in switch state is present, the state managing portion 81 obtains, as shown in Step S73, switch push state data and moreover transmits, in next Step S74, the obtained switch push state data and goes back to the processing of Step S65.

Thus, the state managing portion 81 controls operations by a user such as on the track ball 69, the scope switches SW1 to SW5 and the like and implements processing and the like as well for displaying for a user the state currently under setting and the like visually-friendly as shown in FIG. 12A and the like.

Figure 20:
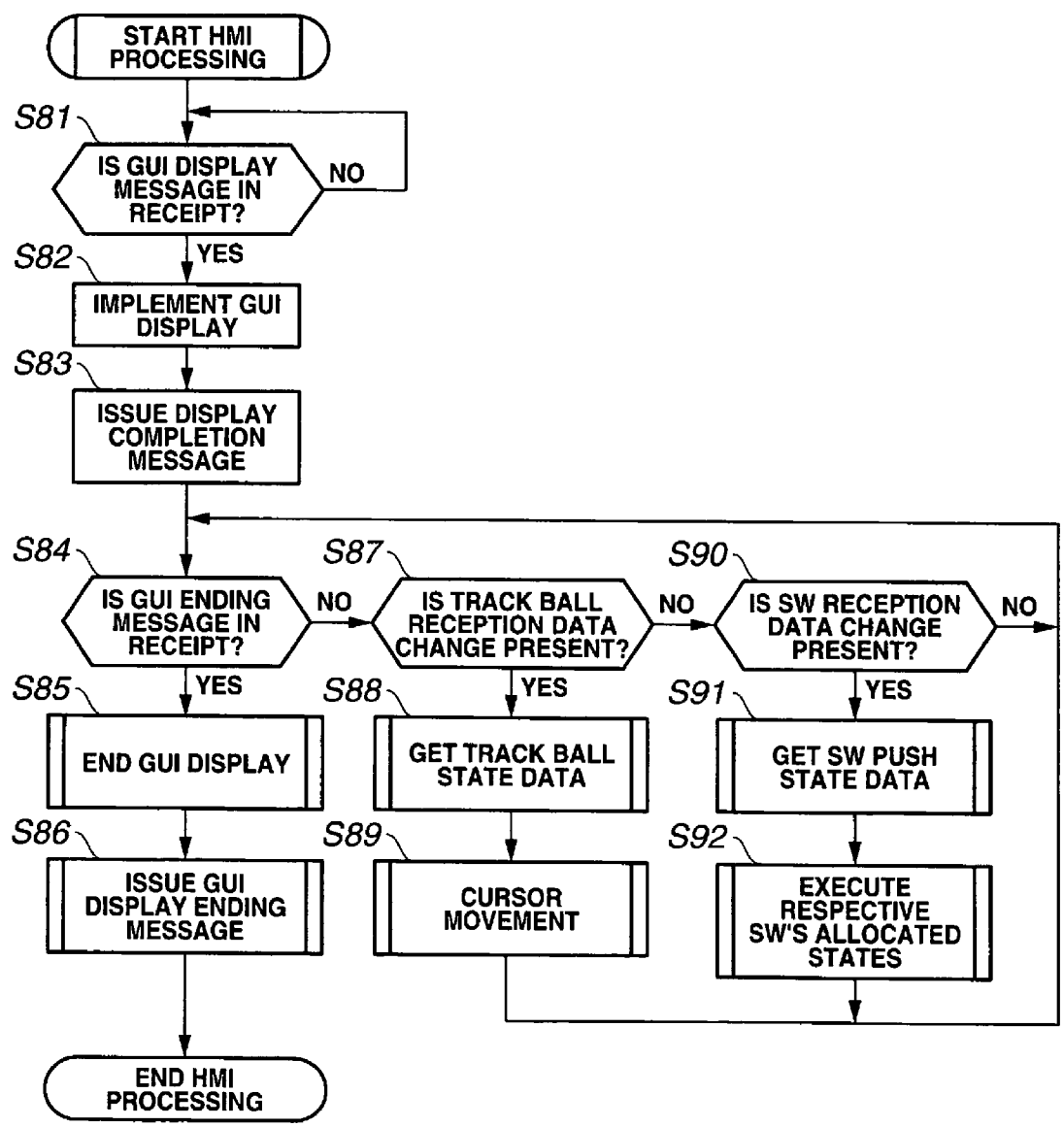
FIG. 20 is a flow chart showing contents of processing at the endoscope system controlling apparatus side in a human interface.

On the other hand, as shown in FIG. 20, when processing of the human interface starts, the CPU of the system controlling unit 117 of the endoscope system controlling apparatus 5 will enter, in the first Step S81, a state of waiting for reception of GUI display message from the side of the endoscope 3. That CPU waits for reception of GUI display message in a wireless system through the transmitting/receiving unit 101 in FIG. 6. And as shown in Step S82, upon receipt of the GUI display message, the CPU of that system controlling unit 117 carries out control processing for GUI display. That is, the CPU controls GUI display on the image processing unit 116.

After GUI display processing in Step S82, as shown in Step S83, the CPU issues display completion massage. The CPU transmits that display completion message through the transmitting/receiving unit 101. In next Step S84, the CPU determines whether or not GUI finalization message is in receipt from the side of the endoscope 3. And, in the case of receiving that GUI finalization message, the CPU carries out processing of finalizing GUI display in Step S85 and thereafter issues GUI finalization message in next Step S86 and finalizes that processing of the human interface.

In Step S84, in the case of receiving no GUI finalization message, the CPU moves to Step S87 to determine whether or not any change is present in reception data on the track ball 69. That determination on presence of change in reception data on the track ball 69 is implemented in receipt of determination result on change in the state of the track ball 69 on the side of the endoscope 3. And in the case where any change is present in the reception data, the state data of the track ball 69 is obtained as shown in Step S88. Moreover, in next Step S89, the CPU moves the movement amount corresponding with the obtained state data (change data) of the track ball 69 and the cursor. And, the step goes back to the processing in Step S84.

In addition, in the processing in Step S87, in the case of determining that no change is present in reception data on the track ball 69, the CPU determines based on reception data in receipt on transmission data on the determination result on the side of the endoscope 3, as shown in Step S90, whether or not any change in present in reception data on switch.

And, in the case of determination that any change is present in the reception data on switch, the CPU obtains, as shown in Step S91, switch push state data from the transmission information from the side of the endoscope 3. Moreover, as shown in Step S91, the CPU implements processing of carrying out the function allocated to a switch which has undergone switch push and goes back to the processing of Step S84. In addition, in Step S90, also in the case where no change is present in reception data of the switch, the step goes back to the processing of Step S84.

According to the endoscope 3 of the present embodiment of forming the endoscope system 1 of carrying out such operations, it is possible to implement a function of instructing the curving portion 27 to curve and in addition operations on the other functions by operations on the track ball 69 of implementing curve instruction operations to be disposed to make a user to operate the endoscope 3 easily and it is possible to secure existing operation functions and realize further better operability.

In addition, according to the endoscope 3 of the present embodiment, that endoscope 3 is made splittable in the operation portion 22 to the endoscope main body 18 and the tube unit 19 to make the side of tube unit 19 into a disposable type and thereby it is possible to implement cleaning, sterilization and the like on the endoscope main body 18.

That is, the air-feed/water-feed conduit 60a and the suction conduit 61a in the endoscope main body 18 can be made substantially short and accordingly is apt to undergo cleaning and sterilization compared with the cases of the prior art where a universal cable corresponding with the tube unit 19 is formed integrally.

In addition, in that case, in the case of the prior art where a universal cable corresponding with the tube unit 19, the universal cable is provided in a connected row arrangement from the operation portion 22 so as to be made bent, but in the present embodiment, the connector portion 51 of the operation portion 22 will be replaced by a conduit connector 51a which is slightly bent and the other portions are replaced by the air-feed/water-feed conduit 60a which extends approximately linearly and the suction conduit 61a, and therefore it is possible to implement processing such as cleaning, sterilization, drying and the like inside the conduits easily and in a short time period. Accordingly, it is possible to set within a short time period to such a state that endoscope inspection can be implemented.

In addition, the present embodiment is structured to connect the endoscope main body 18 to the tube units 19 contactless and detachably, even if the endoscope main body 18 is cleaned and sterilized repeatedly, no conduction defects in contact and the like will occur in the case of not being contactless but reliability can be improved.

Embodiment 2

Next, Embodiment 2 of the present invention will be described with reference to FIG. 21A to FIG. 21D. FIG. 21A to FIG. 21C show an endoscope 3B of Embodiment 2 of the present invention. Here, FIG. 21A shows the operation portion and its surrounding in a partially cutaway state viewed from the side direction; FIG. 21B shows a front elevation viewed from the right side in FIG. 21A; FIG. 21C shows a plan view viewed from the top in FIG. 21A; and FIG. 21D shows a part of an endoscope 3F as a variation. The endoscope 3B of the present embodiment is the endoscope 3 in embodiment 1 provided with no signal line 73b for signal transmission but, in its stead, with a transmitting/receiving antenna portion 121 built-in inside the operation portion 22.

And information such as image data image-captured by a CCD 25, operation data and the like in the case of operating a track ball 69 as operation means and the like are transmitted to the side of the AWS unit 4 through that antenna portion 121. The other configurations are likewise Embodiment 1.

In the endoscope 3B of the present embodiment, an air-feed/water-feed conduit 60a, a suction conduit 61b and an electric power line 73a are inserted through inside the tube unit 19.

In addition, according to the present embodiment, since no signal line 73b is required to be inserted through inside the tube unit 19, it is possible to make a configuration more appropriate to disposal use. Otherwise, likewise Embodiment 1, in the case where a right-hander, a left-hander and the like grasps the grip portion 68 of the endoscope 3B with any of right hand or left hand, operations provide good operability.

FIG. 21D shows an endoscope 3F of a first variation. In the endoscope 3B in FIG. 21A to FIG. 21C, the hook 70 links the both upper and lower ends (in the longitudinal direction) in the grip portion 68 grasped by a hand, but in the endoscope 3F herein, a hook 70' is formed to shape the letter L viewed from the upper end side of the grip portion 68 and the lower end of the hook 70' is not linked to the grip portion 68, and therefore the lower end of the hook 70' is configured to form an opening.

Also in the variation herein, the operation portion 22 or the grip portion 68 will be axisymmetrically on a center line O in their longitudinal direction, and the instruction inputting portion is formed axisymmetrically, operability likewise in the case of Embodiment 1 or Embodiment 2 can be secured.

In addition, a function of preventing the endoscope 3B from possibly dropping in the case of insufficient gripping will be disposed in the portion on the upper end side in the hook 70', and therefore, likewise in the case with the hook 70, approximately likewise function can be maintained. That is, also in that endoscope 3B, the hook 70' is formed to have a protruding portion of protruding in the direction perpendicular to the axis direction of the grip portion 68 from the rear end side of the grip portion 68, and therefore it will be possible to effectively prevent the endoscope 3B from dropping.

In addition, since the lower end side of the hook 70' is open, that portion is hanged onto an endoscope hanger and the like and thereby can be utilized for retaining the endoscope 3F. Thus, the present variation has operations and effects approximately similar to those of Embodiment 2.

FIG. 22A to FIG. 22C show an endoscope 3C of a second variation. That endoscope 3C adopts an operating pad 161 instead of a track ball 69 as operation means.

Here, FIG. 22A is a side view viewed from a side of the endoscope 3C; FIG. 22B is a front elevation viewed from the right side in FIG. 22A; FIG. 22C is a plan view viewed from upward in FIG. 22A; FIG. 22D shows an operating pad viewed from a direction perpendicular to the inclined surface Sa in FIG. 22A, and moreover, in a state disposed along the center line in parallel to the inclined surface Sa; and FIG. 22E shows an operating pad 161' in a state likewise disposed as in FIG. 22D in the variation.

That endoscope 3C adopts a disk-shaped operating pad 161 instead of the track ball 69 in the endoscope 3B shown in FIG. 21A to FIG. 21C. That is, an operating pad 161 is attached onto the inclined surface Sa. That operating pad 161 is provided with switches 162a, 162b, 162c and 162d for instructing operations to vertical and horizontal four directions in four places respectively corresponding with vertical and horizontal four directions. Here, in the case of that operating pad 161, the function of the switch 113 in the track ball 69 is designed to be substituted by two switches for instructing operations in the opposite directions, for example, and specifically, by operations in the case where the switches 162a and 162b are pushed at the same time.

The other configurations are likewise the endoscope 3B shown in FIG. 21A to FIG. 21C.

In addition, as a variation of the operating pad 161A of the second variation, it is advisable that, as shown in FIG. 22E, a cross-shaped operating pad 161' is adopted. That operating pad 161' is also provided with switches 162a, 162b, 162c and 162d for instructing operations to vertical and horizontal four directions in four places respectively corresponding with vertical and horizontal four directions.

In addition, FIG. 23A to FIG. 23C show an endoscope 3D of a third variation. The endoscope 3D herein is provided with two operating pads 163A and 163B in parallel in the direction perpendicular to the center axis O of the endoscope 3C as shown in FIG. 23C, for example, in the location of the track ball 69 on the inclined surface Sa of the endoscope 3B shown in FIG. 21A to FIG. 21C.

The operating pad 163A is provided with switches 162a, 162b in the vertical direction and the operating pad 163B is provided with switches 162c, 162d in the horizontal direction.

The other configurations are likewise those of the endoscope 3B shown in FIG. 21A to FIG. 21C.

In the endoscope 3D in FIG. 23A to FIG. 23C, two operating pad pads 163A and 163B were provided in parallel in the direction substantially perpendicular to the center axis O of the endoscope 3D, but it is advisable that, as shown in the endoscope 3D of the third variation shown in FIG. 24A to FIG. 24C, two operating pads 163C and 163D are provided in parallel in the direction parallel to the center axis C of the endoscope 3D.

Here, the above described embodiment was described in the case of the endoscope system 1 in use of the endoscope 4, but is likewise applicable to the other medical system as well.

Embodiment 3

Next, Embodiment 3 of the present invention will be described with reference to FIG. 25 to FIG. 40. An object of the present embodiment is to provide an endoscope which is simple in physical mechanism for changing the shape of the curving portion and which can change its shape in the curving portion by a predetermined same amount each time by carrying out a predetermined same operation at the time of changing the shape of the curving portion.

Prior to description on specific configurations of the present embodiment, schematic configurations of the present embodiment will be described with reference to FIG. 25 and FIG. 26. Here, the same components as in Embodiment 1 will share the same numbers and characters.

Figure 25:
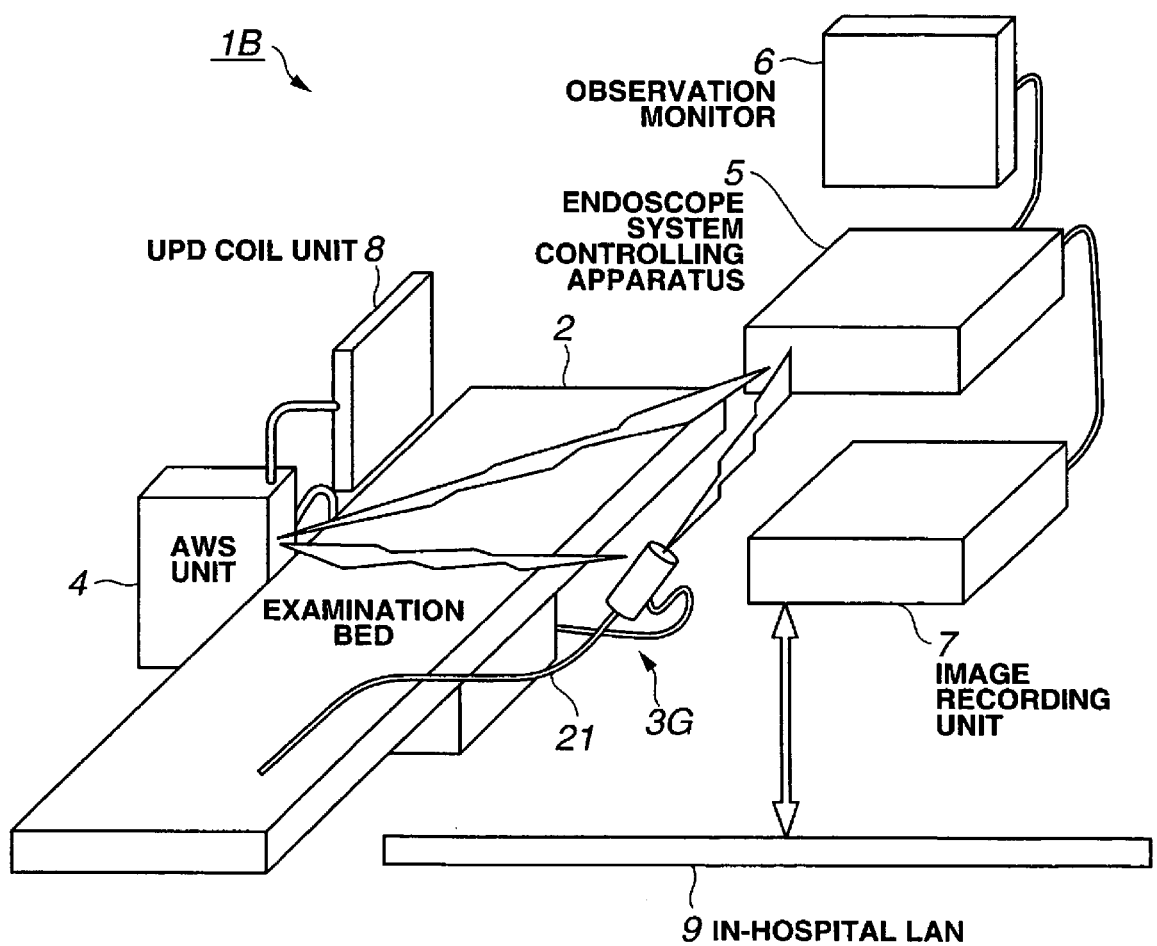
FIG. 25 is a drawing of a schematic configuration of an endoscope system comprising Embodiment 3 of the present invention.

As shown in FIG. 25, an endoscope 1B comprising the present embodiment has; a flexible endoscope (also called as a scope) 3G which is inserted inside a body cavity of a patient not shown in the drawing, who is lying down on an examination bed 2, carrying out endoscope inspection; a air-feed/water-feed/suction unit (hereinafter to be abbreviated as AWS unit) 4 to which the endoscope 3G thereof is connected and which comprises air-feed, water-feed and suction functions; endoscope system controlling apparatus 5 of carrying out signal processing for image capturing elements built-in in the endoscope 3G, controlling processing on respective kinds of operation means provided in the endoscope 3G and the like; and an observation monitor 6 in use of a liquid crystal monitor and the like of displaying video signals generated by the endoscope system controlling apparatus 5 thereof.

In addition, the endoscope system 1B thereof is connected to an image recording unit 7 of carrying out filing digital image signals, for example, generated by the endoscope system controlling apparatus 5 and the like and the AWS unit 4. In the case that a shape detecting coil (hereinafter referred to as UPD coil) is incorporated in the insertion portion of the endoscope 3, the endoscope system 1B has a UPD coil unit 8 for receiving electromagnetic filed signals generated by the UPD coil thereof and the like to detect respective UPD coil positions and display shapes of the insertion portion of the endoscope 3G.

In addition, an image recording unit 7 is connected to a LAN 9 in the hospital provided with the endoscope system 1B hereof so that respective terminal apparatuses in wired or wireless connection can be designed to refer to images and the like filed in the image recording unit 7.

In addition, as shown in FIG. 25, the AWS unit 4 and the endoscope system controlling apparatus 5 are arranged to carry out transmission/reception of information (data) wirelessly. Here, in FIG. 25, the endoscope 3G is connected to the AWS unit 4 with a cable, but it is also advisable that transmission/reception (bilateral transmission) of information (data) is carried out wirelessly. In addition, it is also advisable that the endoscope system controlling apparatus 5 is arranged to carry out transmission/reception of information wirelessly to and from the endoscope 3G. Here, the communication systems described in FIG. 2A to FIG. 2C can be utilized.

Figure 26:
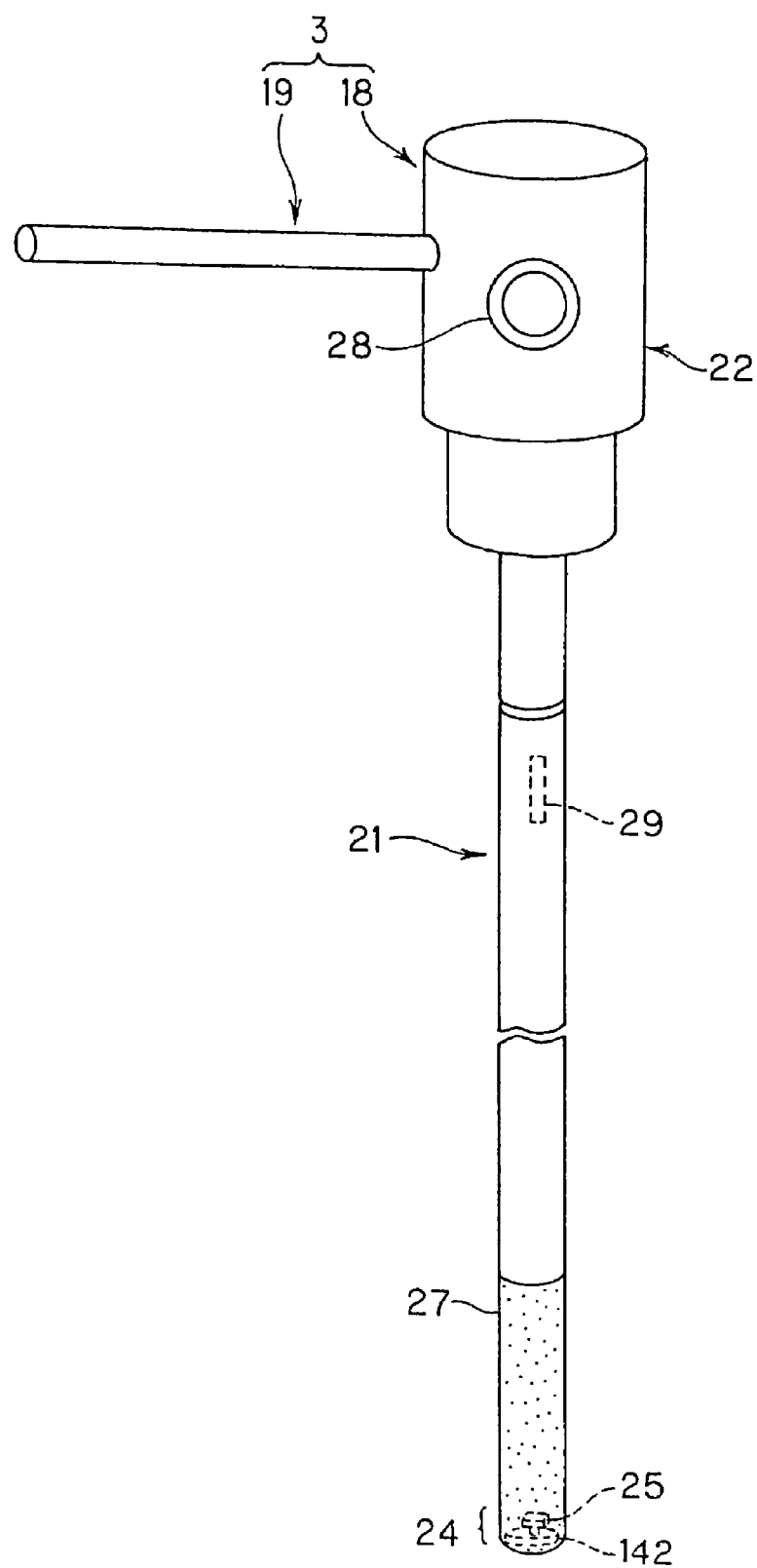
FIG. 26 is a drawing showing a schematic configuration of an endoscope of Embodiment 3.

In addition, FIG. 26 shows a schematic configuration of the endoscope 3G of the present embodiment. That endoscope 3G comprises an endoscope main body 18 and a tube unit 19, which is detachably connected to that endoscope main body 18 and, for example, is a throwaway type (disposable type). The tube unit 19 is caused to have diameter smaller than that of the prior art universal cables and is configured only by an air-feed/water-feed conduit 60b and a suction conduit 60b as two conduit tubes in the present embodiment, a power supply line 73a and a signal line 73b (see FIG. 28).

The endoscope main body 18 has a flexible insertion portion 21 to be inserted into a body cavity and an operation portion 22 provided in the rear end of the insertion portion 21 thereof and a base end of the tube unit 19 is detachably connected to the operation portion 22 thereof.

In addition, an image capturing unit in use of CCD 25 which makes gain variable inside the image capturing unit as an image capturing element is disposed at the tip portion 24 of the insertion portion 21. In addition, the tip portion 24 is provided with a contact sensor 142 of detecting a state where the tip portion 24 is in contact (pressure contact) with the inner wall and the like inside the body cavity. In addition, a curving portion 27 capable of forming a curve with a low force amount is provided in the rear end of the tip portion 24 so as to curve the curving portion 27 by operating an angle/remocon operation element 28 provided in the operation portion 22. The angle/remocon operation element 28 is designed to be capable of implementing an angle operation (curving operation), operations such as air-feed/water-feed, suction and the like, remocon operations and the like as remote controlling operations (specifically, freeze instructing operation and release instruction operation) onto the endoscope system apparatus 5 and the like. In addition, in the insertion portion 21, rigidity-variable portion is formed so as to implement an inserting operation and the like more smoothly.

In addition, the insertion portion 21 is provided in its inside with a cleaning level detecting portion 29 so as to be capable of detecting cleaning level and the like of conduits.

Next, with reference to FIG. 27, further specific configurations of the endoscope system 1B will be described.

There disposed is an observation monitor 6 configured by a liquid crystal monitor and the like being adjacent to the side surface of the examination bed 2; there disposed on a cart 31 disposed movably in the vicinity of one tip portion of the examination bed 2 in the longitudinal direction are an endoscope system controlling apparatus 5, an AWS unit 4, an image file/LAN/an electric scalpel/ultrasonic unit (an image file unit, a wireless LAN or wired LAN, an electric scalpel apparatus, ultrasonic unit and the like are described in a simplified fashion) 32; and a touch paneled monitor 33' is disposed in the top portion.

In addition, the UPD coil unit 8 is embedded on an upper surface portion of the examination bed 2 where a patient lies. That UPD coil unit 8 is connected to the AWS unit 4 with a UPD cable 34.

In the present embodiment, the AWS unit 4 and the endoscope system controlling apparatus 5 transmit/receive data with wireless transmitting/receiving units 77 and 101, for example, as shown in FIG. 6. In addition, as shown in FIG. 27, the observation monitor 6 is connected to a monitor connector of the endoscope system controlling apparatus 5 by a monitor cable 35'.

Figure 27:
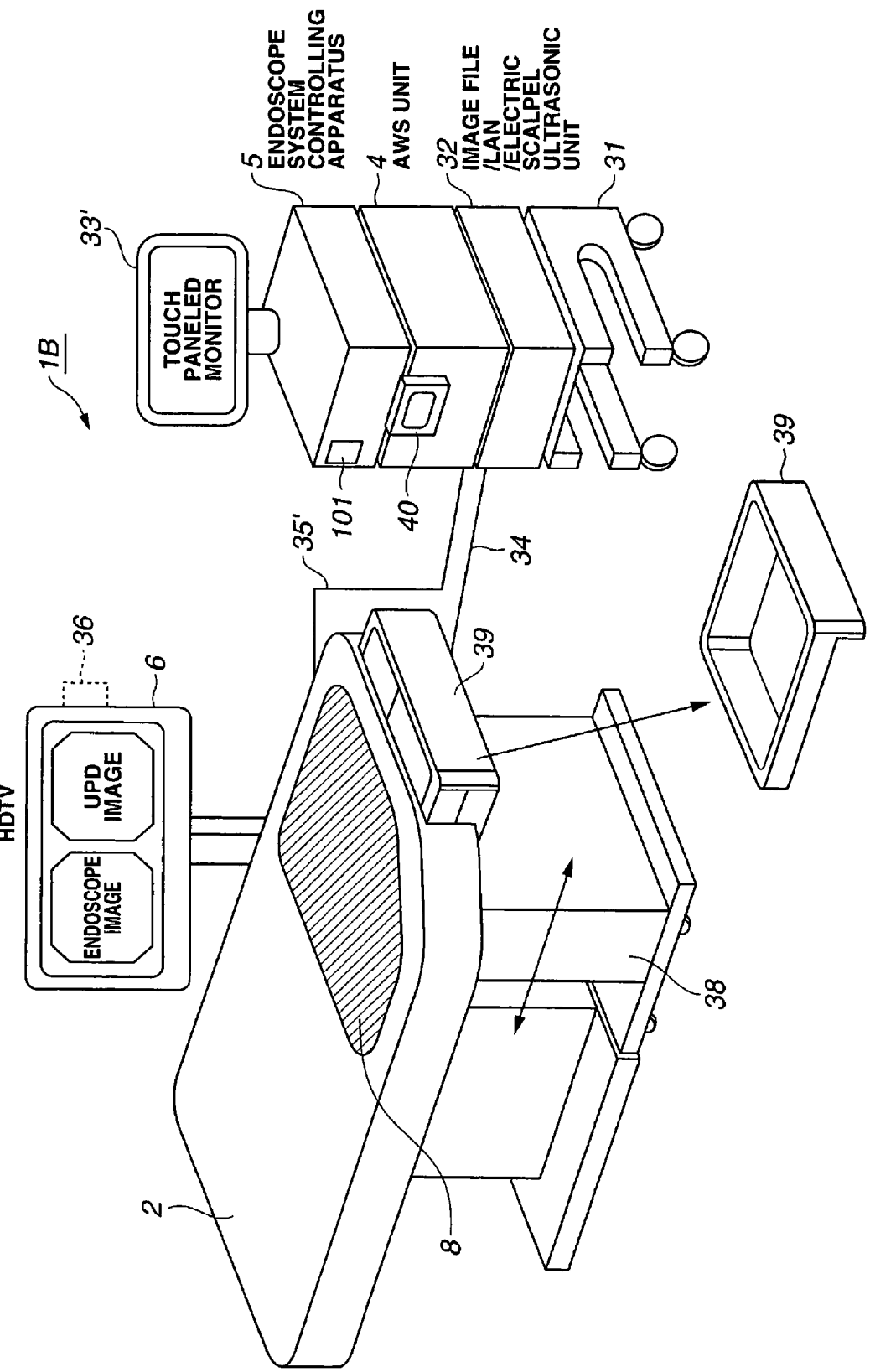
FIG. 27 is a perspective view showing an entire configuration of an endoscope system comprising Embodiment 3.

Here, as shown in FIG. 27, it is advisable that the transmitting/receiving units 101 and 36 are respectively mounted on the endoscope system controlling apparatus 5 and the observation monitor 6 and video signals are transmitted from the endoscope system controlling apparatus 5 to the observation monitor 6 so as to make it possible to display endoscope images corresponding with those video signals onto the display screen.

As will be described below, image data having undergone image capturing with a CCD 25 as well as image data on shapes of the insertion portion detected with a UPD coil unit 8 (UPD image) are transmitted to the endoscope system controlling apparatus 5, from the side of the AWS unit 4, and accordingly the endoscope system controlling apparatus 5 is designed to be capable of sending video signals corresponding with the image data thereof to the observation monitor 6 to display endoscope images as well as UPD images on the display screen thereof.

The observation monitor 6 is configured by a high definition TV (HDTV) monitor so as to be capable of displaying thus a plurality of kinds of images on that display screen concurrently.

Figure 28:
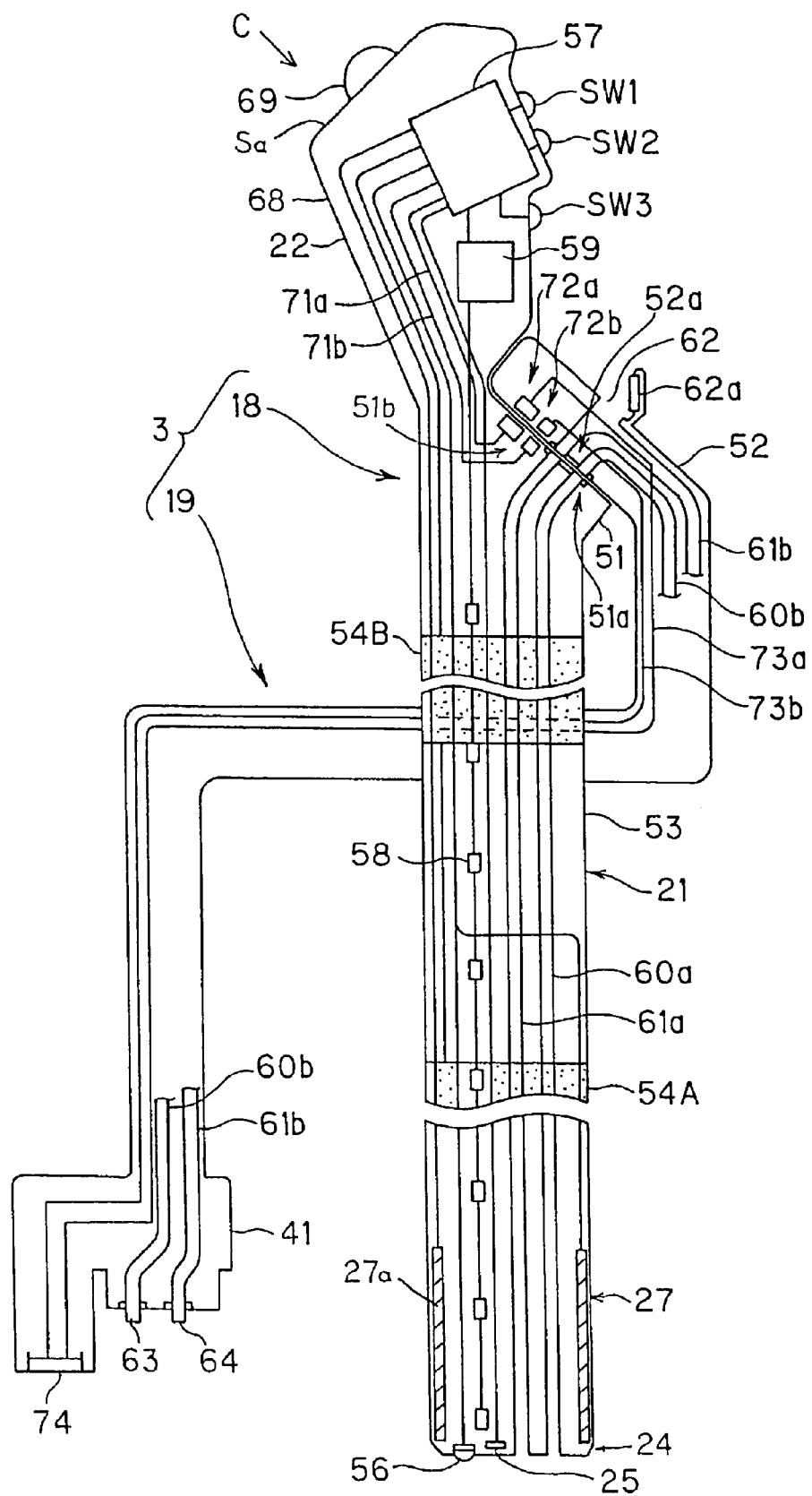
FIG. 28 is an entire view showing a detailed configuration of an endoscope.

In addition, in the present embodiment, a housing concave portion is formed at one end portion of the examination bed 2 in the longitudinal direction and in the positioning of the lower portion thereof, and that housing concave portion is made to be capable of slidably housing a tray conveying trolley 38. A scope tray 39 where the endoscope 3G shown in FIG. 28 is housed is disposed on the top of that tray conveying trolley 38.

And, the scope tray 39 where the endoscope 3G subject to sterilization or disinfection can be conveyed with the tray conveying trolley 38 and can be housed in the housing concave portion of the examination bed 2. An operator can pull out the endoscope 3G from the scope tray 39 to use in endoscope inspection and the last thing to do is to house that scope tray 39 again after endoscope inspection is over. Thereafter, by conveying the scope tray 39 housing the post-use endoscope 3G with the tray conveying trolley 38, sterilization or disinfection can be carried out smoothly.

In addition, as shown in FIG. 27, the AWS unit 4, for example, is provided with a scope connector 40. In addition, a scope connector 41 of the endoscope 3G is detachably connected to the scope connector 40 thereof.

Next, with reference to FIG. 28, a specific configuration of the endoscope 3G of the present embodiment will be described.

In FIG. 26, as described on the diagrammatic points thereof, the endoscope 3G of the present embodiment comprises an endoscope main body 18 having a flexible insertion portion 21 to be inserted into a body cavity and an operation portion 22 provided in the rear end of the insertion portion 21 thereof and a tube unit 19 of a throwaway type (herein to be abbreviated as dispo type) in which a (tube unit connection) connector portion 51 provided in the vicinity of a base end (forward end) of the operation portion 22 in the endoscope main body 18 thereof is detachably connected to a comprehensive connector portion 52 of the base end thereof connected; and the above described scope connector 41 detachably connected to the AWS unit 4 is provided in the very end of the tube unit 19 thereof.

The insertion portion 21 comprises a rigid tip portion 24 provided in the tip of that insertion portion 21, a curving portion 27 curvably provided at the rear end of that tip portion 24 and a longitudinal flexible portion (meandering conduit portion) 53 from the rear end of that curving portion 27 to the operation portion 22; and rigidity-variable actuators 54A and 54B called electrically conductive polymer artificial muscle (to be abbreviated as EPAM) that expands/shrinks with voltage to be applied and can be changed in rigidity as well are provided in a plurality of places intervening the flexible portion 53 thereof, specifically in two places.

A light emitting diode 56 (to be abbreviated as LED) is attached, as lighting means, to the interior of lighting window provided in the tip portion 24 of the insertion portion 21 so that lighting light is emitted forward through a lighting lens integrally attached to that LED 56 to light a shooting subject such as a patient and the like. Here, that LED 56 may be an LED generating white light or may be configured by using an LED for R, an LED for G and an LED for B generating light of respective wavelength ranges of red (R), green (G) and blue (B). Light emitting element of forming lighting means will not be limited to the LED 56 but can be formed with an LD (laser diode) and the like.

In addition, an object lens not shown in the drawing is mounted on the observation window provided adjacent to the lighting window and a CCD 25 with a gain-variable function being built-in is disposed in the image forming position thereof to form image capturing means of shooting a subject. The CCD 25 in the present embodiment has a gain-variable function being built-in in the CCD element itself so that the gain of the CCD output signals can be made easily variable to reach around several 100 times larger with the gain-variable function, and therefore even under the lighting light by the LED 56, bright images with less S/N drop are made derivable.

In addition, since the LED 56 has good light-emitting efficiency compared with the case of an electric lamp, temperature increase in the vicinity of the LED 56 can be restrained.

The other end of a signal line, respective ends of which are connected to the LED 56 and the CCD 25 and inserted to go through inside the insertion portion 21 is provided inside the operation portion 22, for example, and is connected to controlling circuit 57 which carries out concentrated controlling processing (intensive controlling processing).

In addition, UPD coils 58 are provided in a predetermined distance in plurality along the longitudinal direction thereof inside the insertion portion 21. Signal lines connected to the respective UPD coils 58 are connected to the controlling circuit 57 through the UPD coil driving unit 59 provided inside the operation portion 22.

In addition, angle actuators 27a as a curving portion shape variable mechanism formed with EPAM disposed in the longitudinal direction thereof are provided in four places in the circumference direction in the interior of the outer skin in the curving portion 27. The angle actuator 27a is designed to expand/shrink with voltage to be applied and be able to be changed in shape of the curving portion 27.

Due to the above described operations that the angle actuator 27a has, it will become no longer necessary to provide separately a physical mechanism such as curving piece, curving wire and the like as a physical mechanism for changing the shape of the curving portion 27.

Accordingly, it is possible to simplify a physical mechanism for changing the shape of the curving portion 27. In addition, the angle actuators 27a may not have to be provided only in the above described four places, but if they are provided in the interior of the outer skin, they may be provided in four or more places.

Figure 40:
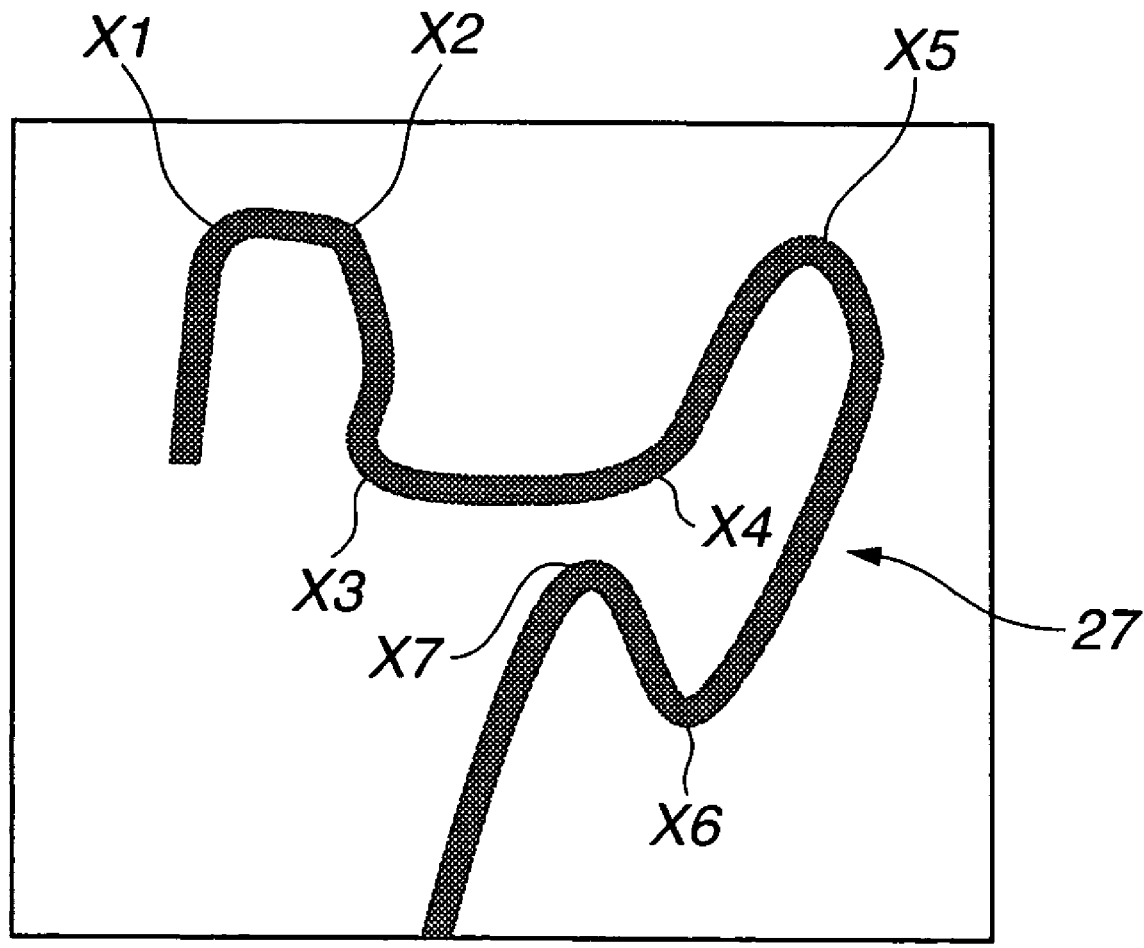
FIG. 40 is a shape of curving portions in appearance at the time when a multi-stage angle operation is implemented.

Moreover, due to the above described operations that the angle actuator 27a has, in the case of providing the angle actuators 27a in four or more places in the circumference direction in the interior of the outer skin, it is possible to cause the curving portion 27 to curve in multiple stages as shown in FIG. 40. Here, in FIG. 40, in the portions X1 to X7, the curving portion 27 is caused to undergo curving to seven stages, but neither will the curving points be limited to the portions X1 to X7 in FIG. 40 nor the number of portions to undergo curving will be limited to seven portions. In addition, the angle actuator 27a thereof and the rigidity-variable actuators 54A and 54B are connected, respectively through the signal lines, to the controlling circuit 57 having a function as curving portion shape controlling means.

EPAM used in the angle actuator 27a and the rigidity-variable actuators 54A and 54B, which has been described in FIG. 9, can be used.

In the case of utilizing it as an angle actuator 27a, it is formed to shape a wire and the like so that one side is caused to expand and the opposite side is caused to shrink and thereby the curving portion 27 can be caused to curve likewise the function by an ordinary wire. Moreover, due to the above described operations that the EPAM has, in the case of utilizing EPAM as an angle actuator 27a, it can change its shape in the curving portion by a predetermined same amount each time by carrying out a predetermined same operation at the time of changing the shape of the curving portion. In addition, those expansion or shrink can make rigidity thereof variable and utilization of function thereof makes rigidity of the portion thereof variable in the rigidity-variable actuators 54A and 54B.

In addition, an air-feed/water-feed conduit 60a and a suction conduit 61a are inserted through inside the insertion portion 21 and the rear end thereof forms a connector portion 51a opening in the connector portion 51. And, a conduit connector 52a in a comprehensive connector portion 52 of the base end of the tube unit 19 is detachably connected to that conduit connector 51a.

And the air-feed/water-feed conduit 60a is connected to air-feed/water-feed conduit 60b inserted through the tube unit 19; the suction conduit 61a is connected to a suction conduit 61b inserted through the tube unit 19 and branched inside the conduit connector 52a to open externally to get communicated to an insertion port (also called as clamp port) 62 which enables insertion of treatment tools such as clamp and the like. The clamp port 62 thereof is blocked by a clamp cap 62a if it is not used.

The rear ends near hands of the water-feed/air-feed mouth ring 60b and the suction mouth ring 61b thereof will become a water-feed/air-feed mouth ring 63 and a suction mouth ring 64 in the scope connector 41.

The water-feed/air-feed mouth ring 63 and the suction mouth ring 64 are respectively connected to the water-feed/air-feed mouth ring 42c and the suction mouth ring 42d of the AWS adaptor 42 shown in FIG. 5A and the like.

In addition, as shown in FIG. 28, the operation portion 22 of the endoscope main body 18 is provided with a grip portion 68 which an operator grasps, and in the periphery thereof inclusive of that grip portion 68, three scope switches SW1, SW2 and SW3, for example, which carry out remote controlling operations (to be abbreviated as "remocon operation") such as release, freeze and the like are provided along an axis in a longitudinal direction of the operation portion 22 and are connected to the controlling circuit 57 respectively.

Moreover on an inclined surface Sa which has been inclined and formed as an upper surface of the opposite side of the position where those scope switches SW1, SW2 and SW3 in the operation portion 22 are provided, there provided in a location to make operable with a hand grasping the grip portion 68 is a track ball 69 in waterproof structure so as to set angle operation (curving operation), the other remocon operations subject to switching and the like.

Figure 29:
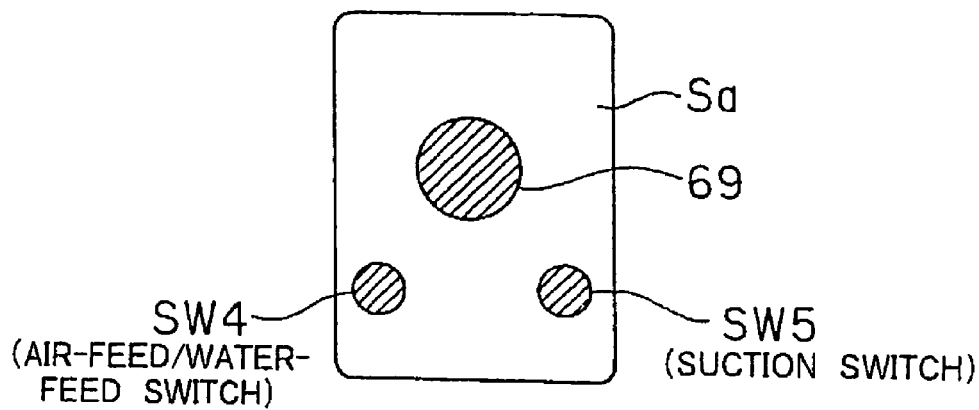
FIG. 29 is a drawing showing a track ball and the like provided in an operation portion viewed in the C direction in FIG. 28.

In addition, FIG. 28 viewed in the C direction is shown in FIG. 29. As shown in FIG. 29, on the both sides of the track ball 69 in that inclined surface Sa, two scope switches SW4 and SW5 are provided in positions axisymmetrical in the horizontal direction to become the both side in the longitudinal direction of the operation portion 22. Normally, functions of an air-feed/water-feed switch and a suction switch are allocated to the scope switches SW4 and SW5 respectively.

In the case of taking it the front elevation in the case of viewing the operation portion 22 of the endoscope 3 in the C direction in FIG. 28, the track ball 69 will come on the center line in the longitudinal direction against the operation portion 22 or the insertion portion 21 in the longitudinal direction; and two scope switches SW4 and SW5 are disposed axisymmetrically together with scope switches SW1, SW2 and SW3 being disposed on the rear side thereof along that center line.

Thus, the operation portion 22 has a plurality of operation means. In addition, in the operation portion 22, respective kinds of operation means such as a track ball 69 and the like are provided axisymmetrically on the center axis in the longitudinal direction thereof and, therefore, in the case where an operator grasps to operate the grip portion 68 of the operation portion 22, in any case of grasping with the left hand and grasping with the right hand to operate, likewise good operability is made to be securable.

Those track ball 69 and scope switches SW4 and SW5 are also connected to the controlling circuit 57. The track ball 69 and scope switches SW1 to SW5 are corresponding to the angle/remocon operation element 28 in FIG. 26.

Here, as will be described below, curving portion shape variable operation means can be allocated to one or a plurality of the track ball 69 and scope switches SW1 to SW5 being operation means. In addition, curving portion shape variable operation means allocated to one or a plurality of the track ball 69 and scope switches SW1 to SW5 give instructions, through operations of an operator, to an angle controlling portion 91 being curving portion shape variable operation means to be described below. And the angle controlling portion 91 in receipt of the instructions shrinks/elongates the angle actuators 27a and thereby can change the shape of the curving portion 27.

Figure 30:
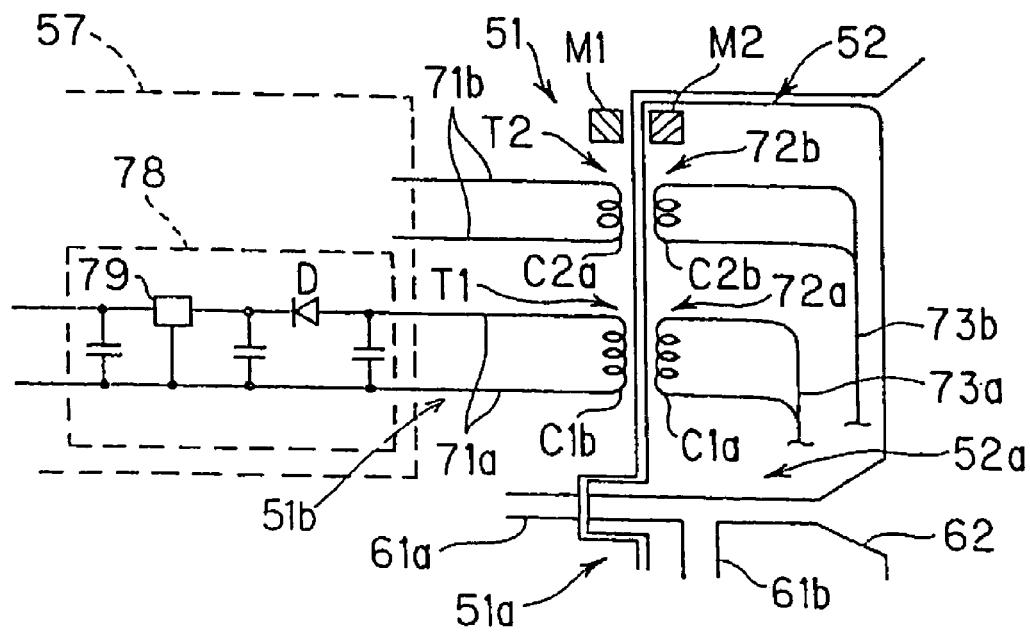
FIG. 30 is a circuit diagram showing a configuration of a contactless transmitting portion a tube unit base tip of which is detachably connected to the operation portion main body.

In addition, the power supply line 71a and the signal line 71b extended out from the controlling circuit 57 are brought into contactless electric connection to the power supply line 73a and the signal line 73b inserted inside the tube unit 19 through the contactless transmitting portions 72a and 72b formed in the connector portion 51 and the comprehensive connector portion 52 (see FIG. 30 for the details). Those of the power supply line 73a and the signal line 73b are connected to an electric connector 74 comprising power supply & signal terminal contacts in the scope corrector 41. Here, the side of the connector portions 51 in the contactless transmitting portions 72a and 72b are called, for example, contactless transmitting units 51b.

And, the user connects that scope connector 41 to the AWS unit 4, and thereby the power supply line 73a is connected to the power supply unit 75 through the electric connector 43 of the AWS unit 4 as having been shown in FIG. 6, while the signal line 73b is connected to the UPD unit 76, the transmitting/receiving unit 77 and the AWS controlling unit 66 (through the power supply unit 75). Here, the transmitting/receiving unit 77 is connected to the antenna of transmitting/receiving radio waves in a wireless system.

FIG. 30 shows a configuration of the contactless connecting portion with the contactless transmitting portions 72a and 72b in the connector portions 51 and 52.

Alternating currency electric power supplied from the power supply unit 75 by the power supply line 73a inserted through inside the tube unit 19 is supplied to coil C1a being on the primary side housed inside the exterior armoring case of the connector portion 52 to form a contactless transmitting portion 72a.

Inside the exterior armoring case of the connector portion 51, a coil C1b being on the secondary side is disposed the above described primary coil C1a and secondary coil C1b are disposed adjacent to form a transformer T1 of implementing electromagnetic coupling in a state with less magnetic flux leakage.

And with that electromagnetic coupling, the alternating current electric power supplied to that coil C1a is efficiently transmitted to the secondary coil C1b. That coil C1b is connected to the power supply circuit 78 inside the controlling circuit 57 to generate, with the power supply circuit 78, direct current electric power required on the side of the controlling circuit 57.

The power supply circuit 78 converts the direct current voltage rectified though a rectifier diode D and a smoothing capacitor into a direct current voltage necessary for operations of the controlling circuit 57 with, for example, three-terminal power supply IC 79 and a smoothing capacitor and supplies it to the controlling circuit 57.

In addition, a signal line 71$b$ (forming a common signal transmitting means) connected to the controlling circuit 57 is connected to the coil C2$a$ forming the contactless transmitting portion 72$b$; and the coil C2$b$ opposite to and adjacent to that coil C2$a$ is connected to the signal line 73$b$ inserted through inside the tube unit 19. That is, approximately likewise the case of the transformer T1, the contactless transmitting portion 72$b$ is formed with the transformer T2 of bringing the coils C2$a$ and C2$b$ into electromagnetic coupling.

Through the coils C2$a$ and C2$b$ undergoing electromagnetic coupling, signals are transmitted from the side of the signal line 71$b$ to the side of the signal line 73$b$ and the signals are also transmitted to the inverse direction.

As will be described on its interior configuration with reference to FIG. 31, the present embodiment is configured to control or manage the respective types of operation means and image capturing means and the like in a concentrated fashion with the controlling circuit 57, and thereby is designed to make it possible to reduce the number of electric signal lines to be inserted through inside the tube unit 19. In addition, also in the case where the functions provided to the endoscope 3G are changed, the signal line 73$b$ inside the tube unit 19 can be used as is without any change. That is, the signal line 73$b$ forms common signal transmitting means of commonly transmitting respective types of signals.

Here, as shown in FIG. 30, magnets M1 and M2 are disposed, for example, adjacent to the transformer T2 and opposite each other against the heterogeneous magnetic pole; and at the time of connecting the comprehensive connector portion 52 to the connector 51, the coils C1$a$ and C1$b$ are designed to be mounted detachably to be disposed adjacent to and opposite to the coils C2$a$ and C2$b$ each other. Here, it is advisable that, instead of the magnets M1 and M2, relief portions are provided to fit the both of connector portions 51 and 52 mutually so as to implement positioning.

Thus, one of characteristics of the endoscope 3G of the present embodiment is to be configured to connect the endoscope main body 18 to the tube unit 19 contactlessly and detachably.

Figure 31:
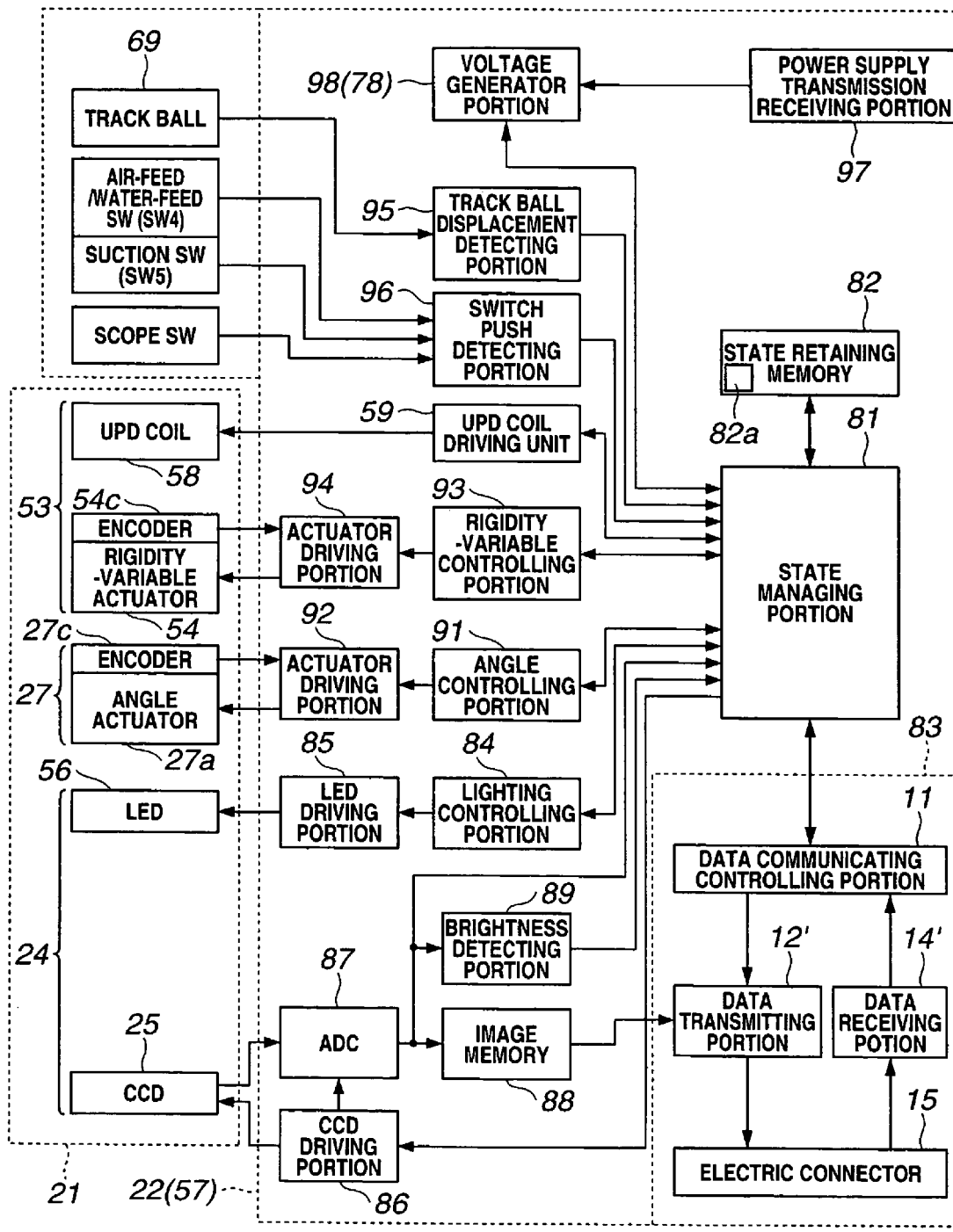
FIG. 31 is a block diagram showing a configuration of the electric system of the configuring elements provided inside an endoscope.

FIG. 31 shows a configuration of the electric system in the main components disposed in the respective portions of the controlling circuit 57 and the like disposed inside the operation portion 22 of the endoscope main body 18 and insertion portion 21. Since the configuration in FIG. 31 has been described in FIG. 11, major portions of that description will be omitted.

Here, the state managing portion 81 is connected to a transmitting/receiving unit 83 in a wired system of carrying out wired communication with the AWS unit 4 (in the present embodiment) (the transmitting/receiving unit 83 hereof is corresponding to FIG. 2B and symbols in FIG. 2B are applied to its components for showing. However, the electric connector 15 is a contactless transmitting portion 72$a$ and 72$b$ inside the operation portion 22 and will become an electric connector 74 at the end portion of the tube unit 19).

In addition, the state managing portion 81 controls the actuator driving portion 92 through the angle controlling portion 91 being curving portion shape variable operation means to manage to drive the angle actuator (EPAM) 27$a$ with that actuator driving portion 92. Here the amount of driving that angle actuator (EPAM) 27$a$ is detected by the encoder 27$c$ and the driving amount is controlled so as to match a value corresponding with the designated value. In addition, the angle controlling portion 91 being curving portion shape variable operation means controls the angle actuator 27$a$ being curving portion shape variable mechanism to expand/shrink and to thereby change shape of the curving portion 27.

In addition, the state managing portion 81 controls the actuator driving portion 94 through the rigidity-variable controlling portion 93 while that actuator driving portion 94 manages to drive the rigidity-variable actuator 54. Here, the amount of driving that rigidity-variable actuator 54 is detected by the encoder 54$c$ so that the driving amount thereof is controlled so as to reach a value corresponding with the designated value.

In addition, an input to that state managing portion 81 is carried out through a track ball displacement detecting portion 95 corresponding with the operation amount from the track ball 69 and the like provided in the operation portion 22.

In addition, operation of switch pushing such as ON and the like by the air-feed/water-feed SW, the suction SW and the scope SW is detected by switch push detecting portion 96 and the detected information thereof is inputted to the state managing portion 81. The EPAM has a property to generate electromotive force by deformity due to external force and it is advisable that the EPAM disposed on the opposite side of the EPAM to be driven is used as an encoder.

In addition, the controlling circuit 57 has a power supply transmission receiving portion 97 and a voltage generator portion 98. The power supply transmission receiving portion 97 is, specifically, a contactless transmitting unit 72$a$ in the operation portion 22. And, the alternating current power supply transmitted by the voltage generator portion 98 is converted into direct voltage in the voltage generator portion 98. That voltage generator portion 98 is equivalent to the power supply circuit 78 in FIG. 30. Direct current power supply generated by the voltage generator portion 98 supplies respective portions inside the controlling circuit 57 with electric power required for action thereof.

Figure 32:
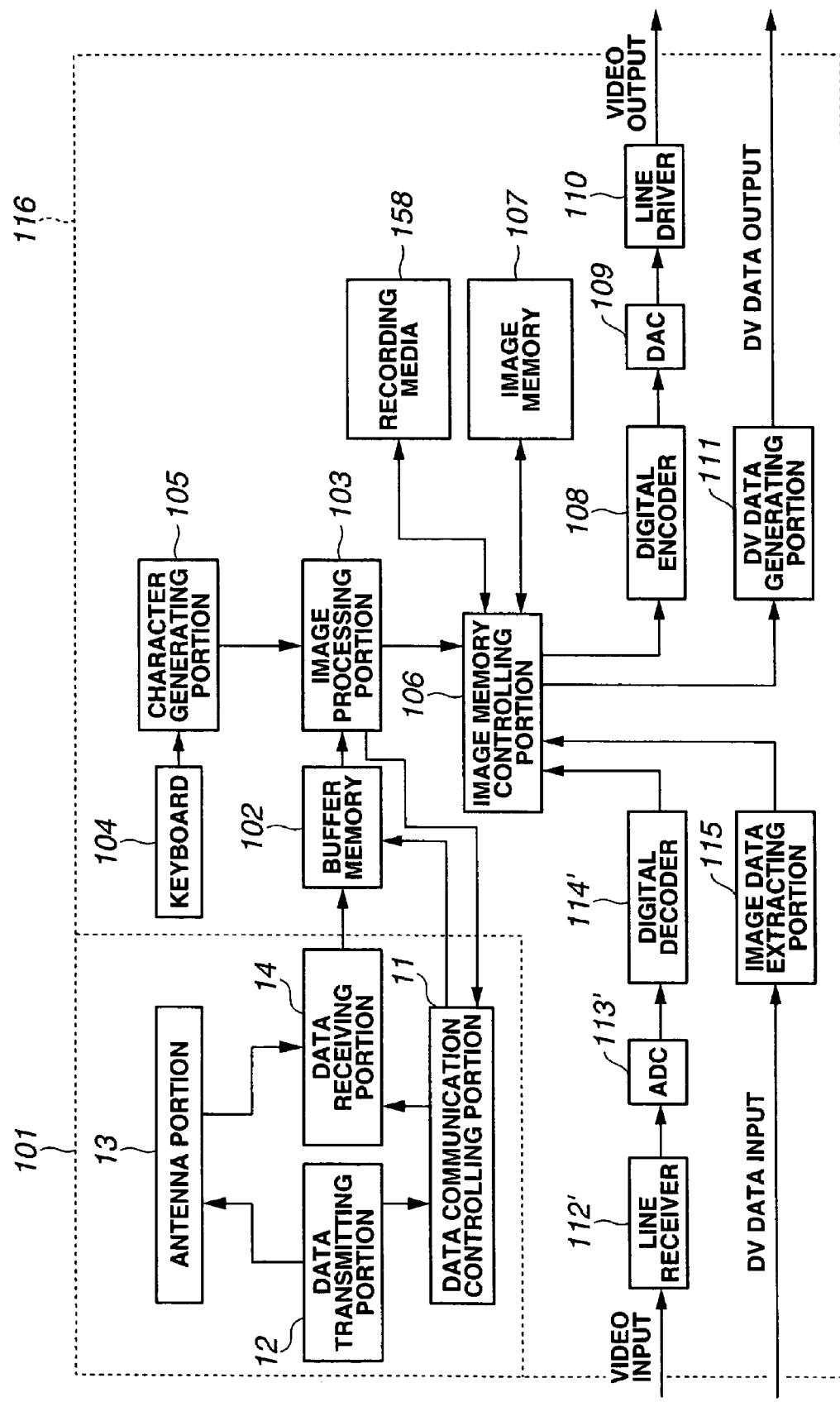
FIG. 32 is a block diagram showing a configuration of the electric system of main portions of an endoscope system controlling apparatus.

FIG. 32 shows an interior configuration of the transmission/reception unit 101 and the image processing unit 116 shown in FIG. 6 in the endoscope system controlling apparatus 5.

That endoscope system controlling apparatus 5 has, for example, a transmission/reception unit 101 in a wireless system. Data such as image signals and the like transmitted wirelessly from the AWS unit 4 are taken in by the antenna portion 13 and transmitted to the data receiving portion 14 and amplified and thereafter undergo demodulation. Operations of that data receiving portion 14 are controlled by the data communicating controlling portion 11 and the data in receipt are sequentially stored in the buffer memory 102.

Image data of that buffer memory 102 are sent to the image processing portion 103 of implementing image data processing. To that image processing portion 103, character information from a character generating portion 105 of generating character information by key input of a keyboard 104 beside image data from the buffer memory 102 is inputted so that the character information can be superimposed and the like into the image data.

The image processing portion 103 sends the inputted image data and the like to the image memory controlling portion 106, temporarily stores the image data in the image memory 107 through that image memory controlling portion 106 and records them into recording media 158.

In addition, the image memory controlling portion 106 read the image data temporarily stored in the image memory 107 and sends them to a digital encoder 108; then the digital encoder 108 encodes the image data in a predetermined video system and outputs them to a D/A converter (to be abbreviated to DAC) 109. That DAC 109 converts digital video signals to analog video signals. Those analog video signals are outputted to the observation monitor 6 from the video output end further through a line driver 110; and images corresponding with the video signals are displayed on the observation monitor 6.

In addition, the image data temporarily stored in the image memory 107 are read out and inputted to a DV data generating portion 111 as well; DV data are generated by that DV data generating portion 111; and the DV data are outputted from the DV data output end.

In addition, that endoscope system controlling apparatus 5 is provided with a video input end and a DV data input end; and video signals inputted from the video input terminal and video signals converted into digital signals through a line receiver 112' and an ADC 113' are demodulated by a digital decoder 114' and inputted to the image memory controlling portion 106.

In addition, as for the DV data inputted to the DV data input end, image data are extracted (decoded) by an image data extracting portion 115 and inputted to the image memory controlling portion 106.

The image memory controlling portion 106 temporarily stores, in the image memory 107, video signals (image data) inputted from the video input end or the DV data input end; records them in the recording media 158; or outputs them from the video output end to the observation monitor 6.

In the present embodiment, image data captured by a CCD 25 of the endoscope 3 and UPD image data generated by the UPD unit 76 are inputted wirelessly from the side of the AWS unit 4 to the endoscope system controlling apparatus 5; and the endoscope system controlling apparatus 5 converts those image data into a predetermined video signals and outputs them to the observation monitor 6. Here, it is also advisable that the endoscope system controlling apparatus 5 receives UPD coil position data instead of the UPD image data to generate UPD image data inside the image processing portion 103.

Figure 33:
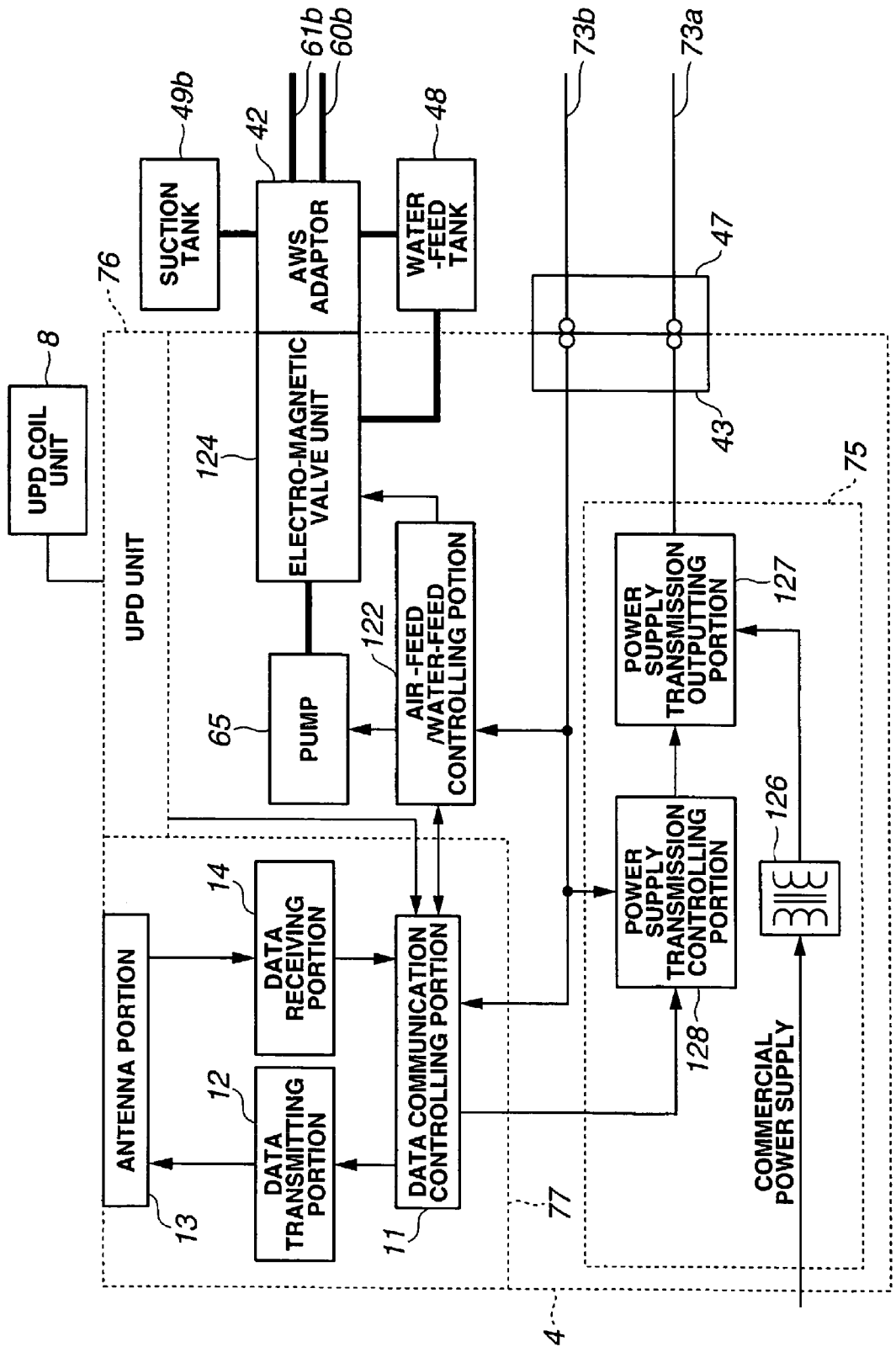
FIG. 33 is a block diagram showing a configuration of six electric systems of an AWS unit.

FIG. 33 shows an internal configuration of the AWS unit 4.

The image data and operation data such as switches and the like inputted from the controlling circuit 57 of the endoscope 3G to scope electric connector 43 are outputted to the data communication controlling portion 11 of the transmission/reception unit 77 and are transmitted, together with the UPD image data from the UPD unit 76, from the antenna portion 13 to the antenna portion 13 of the endoscope system controlling apparatus 5.

On the other hand, AWS related information such as operations on air-feed/water-feed switches, suction switch and the like provided in the operation portion 22 of the endoscope 3G are sent to the air-feed/water-feed controlling portion 122, and that air-feed/water-feed controlling portion 122 controls operations of the pump 65 and the electromagnetic valve unit 124 corresponding with the operated information. The air-feed/water-feed conduits 60b and 61b are connected to the electromagnetic valve unit 124 through the AWS adaptor 42. In addition, a water-feed tank 48 is connected to the electromagnetic valve unit 124 and the AWS adaptor 42; and a suction tank 49b is connected to the AWS adaptor 42.

In addition, a commercial power supply is supplied to the AWS unit 4; and that commercial power supply is sent to a power supply transmission outputting portion 127 through an insulated transformer 126. That power supply transmission outputting portion 127 supplies alternating current power supply insulated from the commercial power supply from the electric connector 43 to the power supply line 73a of the endoscope 3 connected to that electric connector 43.

Electric power transmitting output of the above described power supply transmission outputting portion 127 is controlled by the power supply transmission controlling portion 128 connected to the data communication controlling portion 11.

In the case where the endoscope system 1B comprising the present embodiment takes in the power supply, the observation monitor 6 displays various kinds of images, for example, as in FIG. 12A.

As a menu displayed in the menu displaying region Rm, the main menu shown in FIG. 12B is displayed. That main menu displays an ending item of carrying out operation instruction of ending the menu when a scope switch, angle sensitivity, insertion portion rigidity, zoom, image enhancement, an air-feed amount, and operation instruction to bring the preceding menu window back are implemented.

And a user operates the track ball 69 and the like to move the selection frame to a scope switch item for selection, then the frame of the item of that scope switch will be displayed thickly to show current selection; and moreover, determining operation is implemented by pushing the track ball 69, and thereby as shown in FIG. 12C, it is possible to select/set a function of allocating five scope switches SW1 to SW5.

Next, operations of the endoscope system 1B according to such a configuration will be described.

As prior preparation for carrying out endoscope inspection, at first a comprehensive connector portion 52 on the side of the tube unit 19 of a dispo type is connected to the connector portion 51 of the operation portion 22 of the endoscope main body 18. In that case, the transformers T1 and T2 forming the contactless transmitting portions 72a and 72b will be mutually brought into electromagnetic connection in an insulated and waterproof state. That connection completes preparation of the endoscope 3G.

Next, the scope connector 41 of the tube unit 19 is connected to the connector 43 of the AWS unit 4. Employing one-touch connection, a single connecting operation completes connection with respective types of conduit, power supply line, signal line and light. There is no need to implement connection of respective conduits, connection of electric connector and the like each time respectively as in conventional endoscope system.

In addition, a user connects the AWS unit 4 to a UPD coil unit 8 and connects the endoscope system controlling apparatus 5 to the observation monitor 6. In addition, complying with necessity, the endoscope system controlling apparatus 5 is connected to the image recording unit 7 and the like, thereby completing set-up of the endoscope system 1B.

Next, the power supplies of the AWS unit 4 and the endoscope system controlling apparatus 5 are put ON. Then, the respective portions inside the AWS unit 4 reaches operating states while the power supply unit 75 will reach a state of being capable of supplying electric power to the side of the endoscope 3 through the power supply line 73a and the like.

Operations at the time of start-up of the AWS unit 4 and the endoscope 3 in that case will be described with reference to FIG. 34 and FIG. 35.

Figure 34:
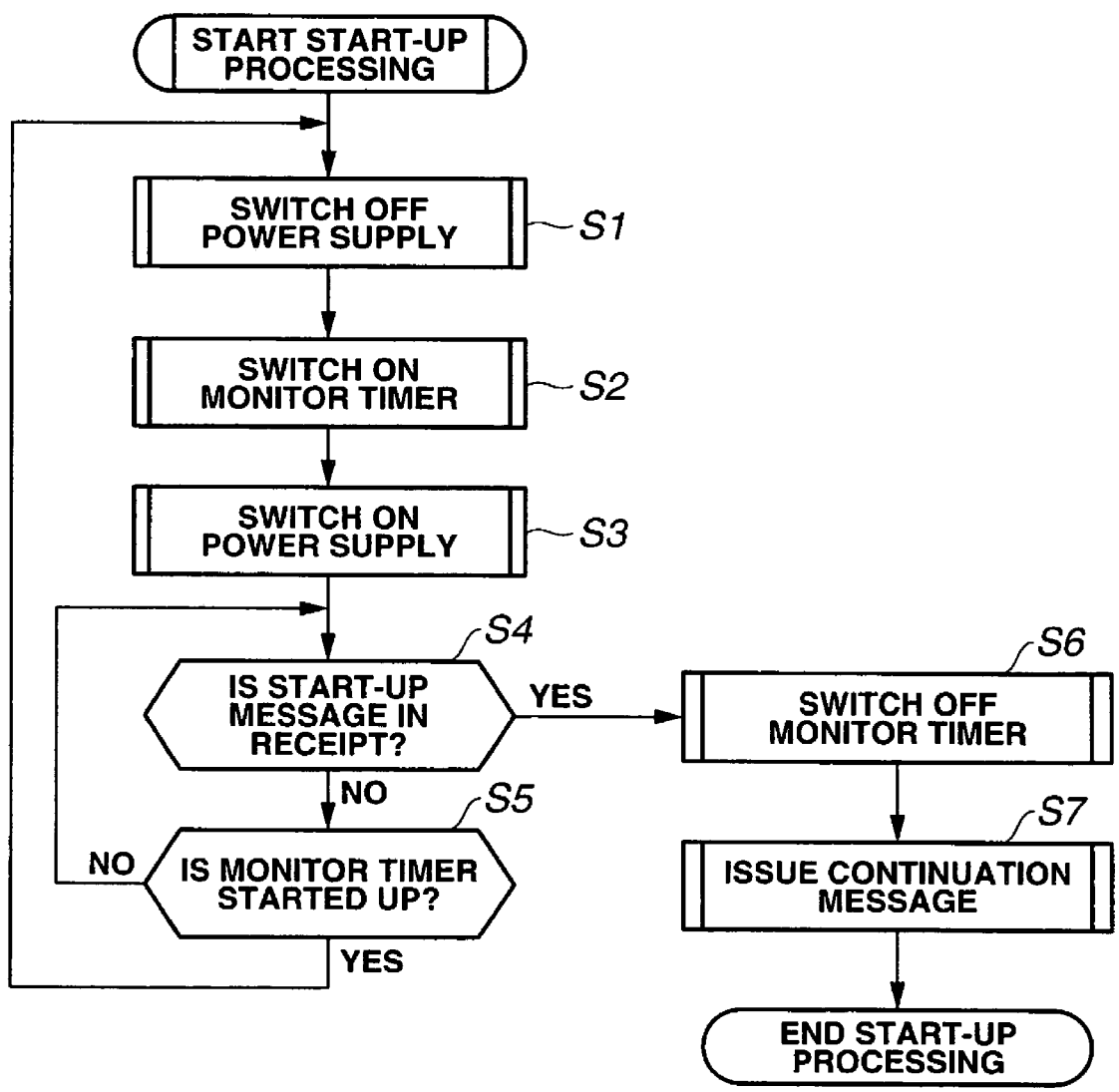
FIG. 34 is a flow chart showing contents of operating start-up processing of an AWS unit.
Figure 35:
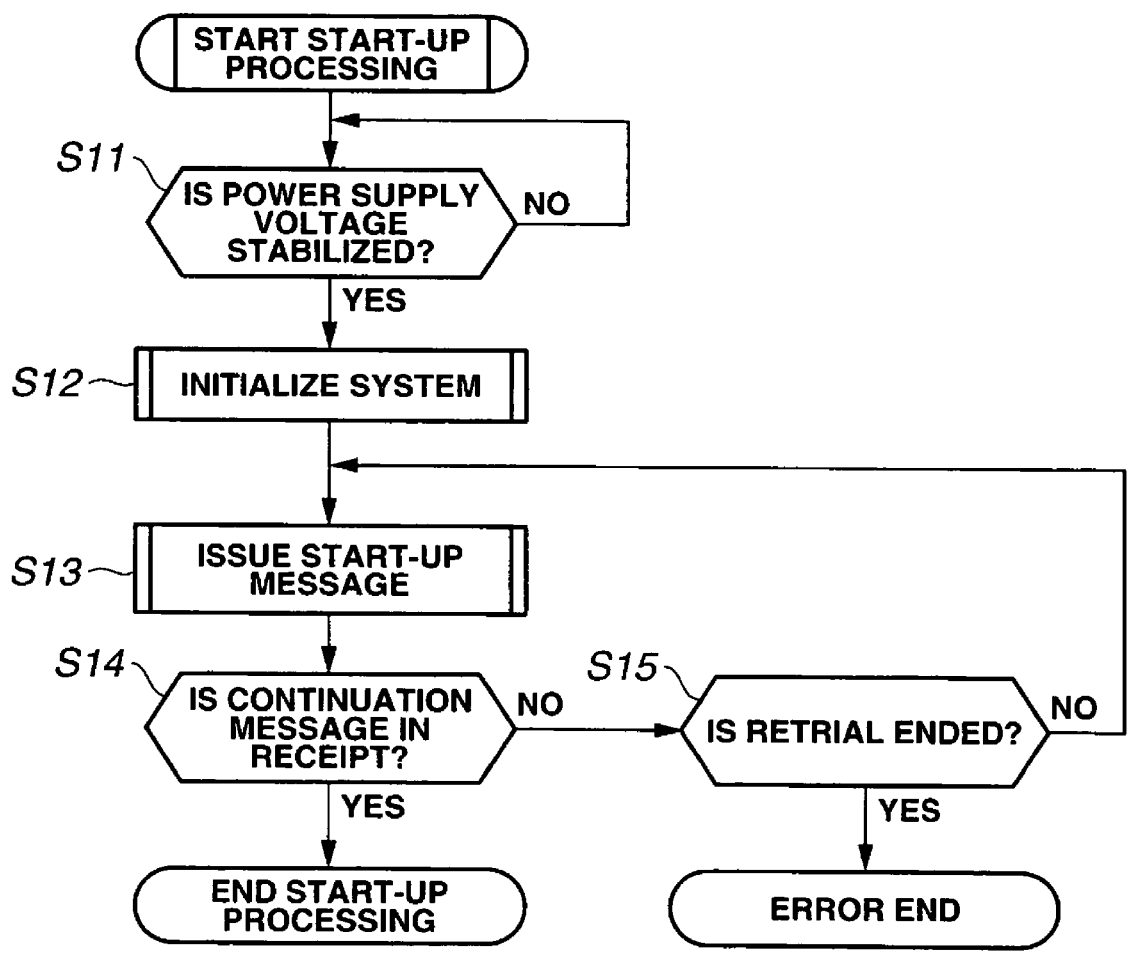
FIG. 35 is a flow chart showing contents of operating start-up processing of an endoscope.

The power supply transmission controlling portion 128 inside the power supply unit 75 of the AWS unit 4 shown in FIG. 33 starts start-up processing, and then sets the state of the power supply transmission outputting portion 127 to a halt on electric power supply in first Step S1 as shown in FIG. 34, that is, put OFF electric power supply.

Thereafter, in Step S2, after putting ON a monitor timer, it sets the state of the power supply transmission outputting portion 127 to a state of supplying electric power as shown in Step S3, that is, puts ON electric power supply. Now that the power supply transmission outputting portion 127 is in a state of supplying electric power, that electric power or alternating current electric power will be supplied to the voltage generator portion 98 inside the controlling circuit 57 of the operation portion 22 through the power supply line 73a inside the tube unit 19 and moreover through the contactless transmitting portion 72a.

Thereafter, as shown in Step S4, the power supply transmission controlling portion 128 will enter a state of waiting for reception of start-up message from the side of the endoscope 3 through the signal line 73b inside the tube unit 19. And, in the case of receiving no start-up message, the power supply transmission controlling portion 128 determines, as shown in Step S5, whether or not the monitor timer has run out of time; and in the case where the time is not up yet, the step goes back to Step S4 while, in the case where the time is up, the step goes back to first Step S1.

On the other hand, in Step S4, in the case of receiving the start-up message before running out of time, the power supply transmission controlling portion 128 put OFF time measurement of the monitor timer as shown in Step S6. And, as shown in Step S7, continuation message is issued and that start-up processing is over.

On the other hand, when the voltage generator portion 98 is supplied with alternate current electric power, the controlling circuit 57 of the endoscope 3G is supplied with alternate current electric power necessary for operations inside the controlling circuit 57 and starts start-up processing. And, the state managing portion 81 shown in FIG. 31 waits, in first Step S11, until the power supply voltage of the voltage generator portion 81 is stabilized.

And in the case where the power supply voltage is stabilized, the state managing portion 81 carries out, in next Step S12, system initialization on respective portions of the controlling circuit 57. After that system initialization, as shown in Step S13, the state managing portion 81 transmits start-up message to the power supply transmission controlling portion 128 through the transmitting/receiving unit 83 and moreover through the signal line 73b inside the tube unit 19.

After transmitting that start-up message, as shown in Step S14, the state managing portion 81 will enter a state of waiting for reception of continuation message from the side of the power supply transmission controlling portion 128; and in the case of receiving the continuation message, finalizes the start-up processing. On the other hand, in the case of receiving no continuation message, as shown in Step S15, the state managing portion 81 goes back to Step S13 to issue the start-up message again in the case where conditions of retrial finalization (for example, conditions of retrial rounds set in advance) are not fulfilled; and in the case where the retrial finalization conditions are applicable, adopts an error end.

When information start-up processing is normally over, image capturing by CCD 25 starts and a user can implement air-feed/water-feed, suction, an angle operation, a rigidity-variable operation and the like with operation means of the operation portion 22.

Figure 36:
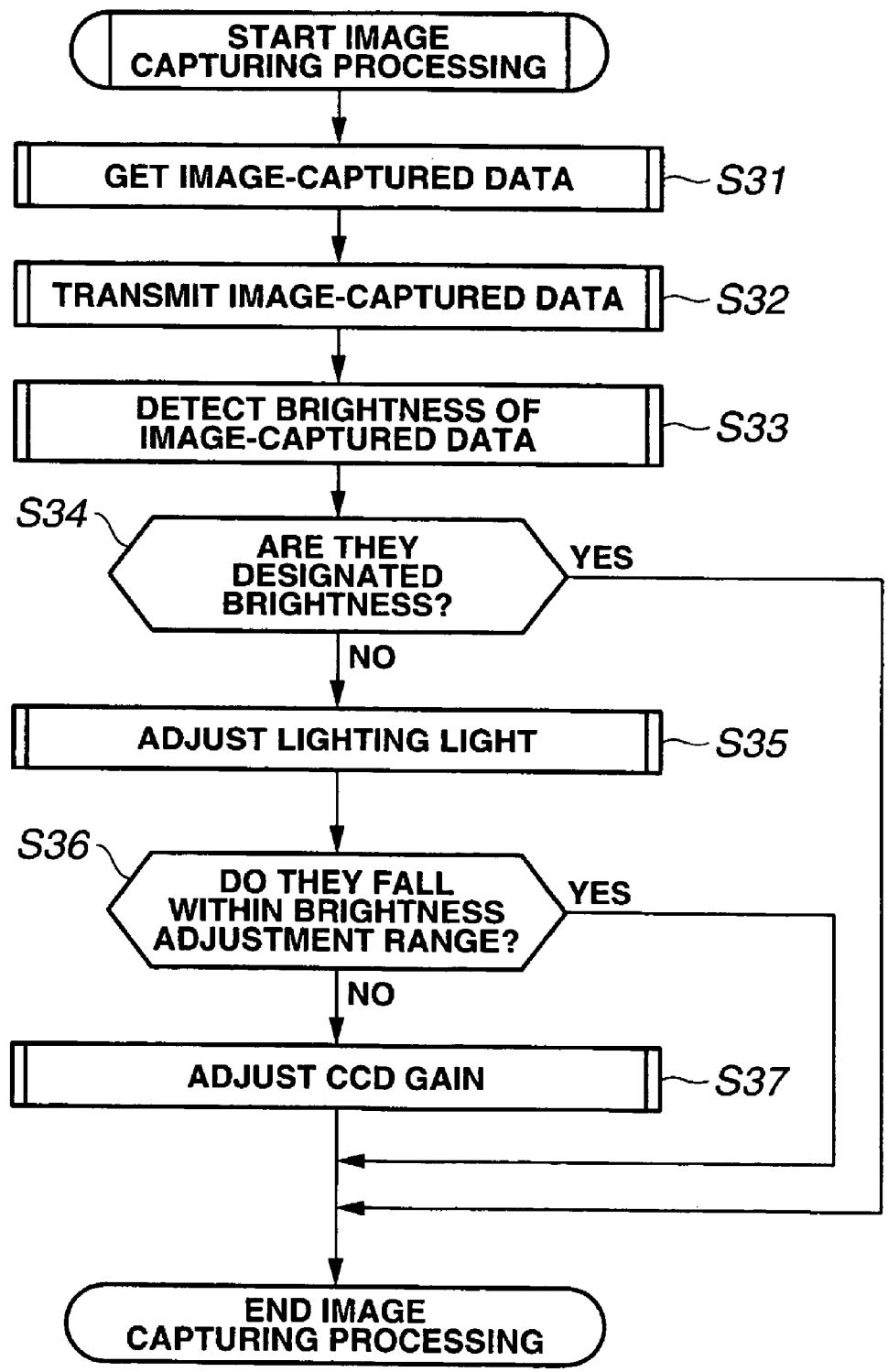
FIG. 36 is a flow chart showing contents of operation of an image capturing controlling processing.

Representative processing operations on them will be described with reference to FIG. 36 to FIG. 38. FIG. 36 shows contents of operations of image capturing controlling processing.

As shown in FIG. 36, when image capturing processing starts, the endoscope 3G obtains, as shown in step S31, image-captured data. Specifically, under management (control) of the state managing portion 81, the LED 56 emits light and the CCD driving portion 86 starts an operation to drive the CCD 25; and the image capturing signals captured by the CCD 25 are converted to digital signals (image-captured data) by an ADC 87. Those image-captured data (image data) are sequentially stored in the image memory 88 to obtain the image-captured data.

The obtained image data are sequentially transmitted as shown in Step S32. The image data read from the image memory 88 are transmitted from the transmitting/receiving unit 83 to the AWS unit 4 in a wired system; and are transmitted wirelessly from the transmitting/receiving unit 77 of that AWS unit 4 to the side of the endoscope system controlling apparatus 5; are converted to video signals inside the endoscope system controlling apparatus 5; and will be displayed on the observation monitor 6.

In addition, the image-captured data of the ADC 87 are inputted to the brightness detecting portion 89. As shown in Step S33, that brightness detecting portion 89 detects brightness of the image-captured data by calculating the average value of luminance data of the image-captured data on an appropriate time basis.

Detected data of that brightness detecting portion 89 are inputted, for example, into the state managing portion 81 so as to determine whether or not they match designated brightness (Step S34). And, in the case of designated brightness, the image capturing processing is finalized to move on to the next image capturing processing.

On the other hand, in Step S34, in the case of determination that the designated brightness is not detected, the state managing portion 81 transmits, as shown in Step S35, instructing signals (controlling signals) for lighting light adjustment to the lighting controlling portion 84; and the lighting controlling portion 84 adjusts the light amount of lighting. For example, the lighting controlling portion 84 adjusts the light amount of lighting by increasing or decreasing the driving current to cause the LED 56 to emit light. The lighting controlling portion 84 returns that adjustment result to the state managing portion 81.

Accordingly, the state managing portion 81 determines, based on the adjustment result information, whether or not brightness falls within the brightness adjustment range that the lighting controlling portion 84 can handle (Step S36). And, in the case where brightness adjustment is made by the lighting controlling portion 84, processing in Step S37 is not implemented but that image capturing processing control is finalized.

On the other hand, in the case where the range of brightness adjustment by the lighting controlling portion 84 is not applicable, as shown in Step S37, the state managing portion 81 outputs signals of CCD gain adjustment to the CCD driving portion 86 to adjust gains of the CCD 25 and thereby implement brightness adjustment on the image-captured data. And, that image capturing processing is over.

Next, air-feed/water-feed processing in FIG. 37 will be described. As shown in FIG. 29, functions of an air-feed/water-feed switch and a suction switch are normally allocated to the both side of the track ball 69 in the operation portion 22.

Figure 37:
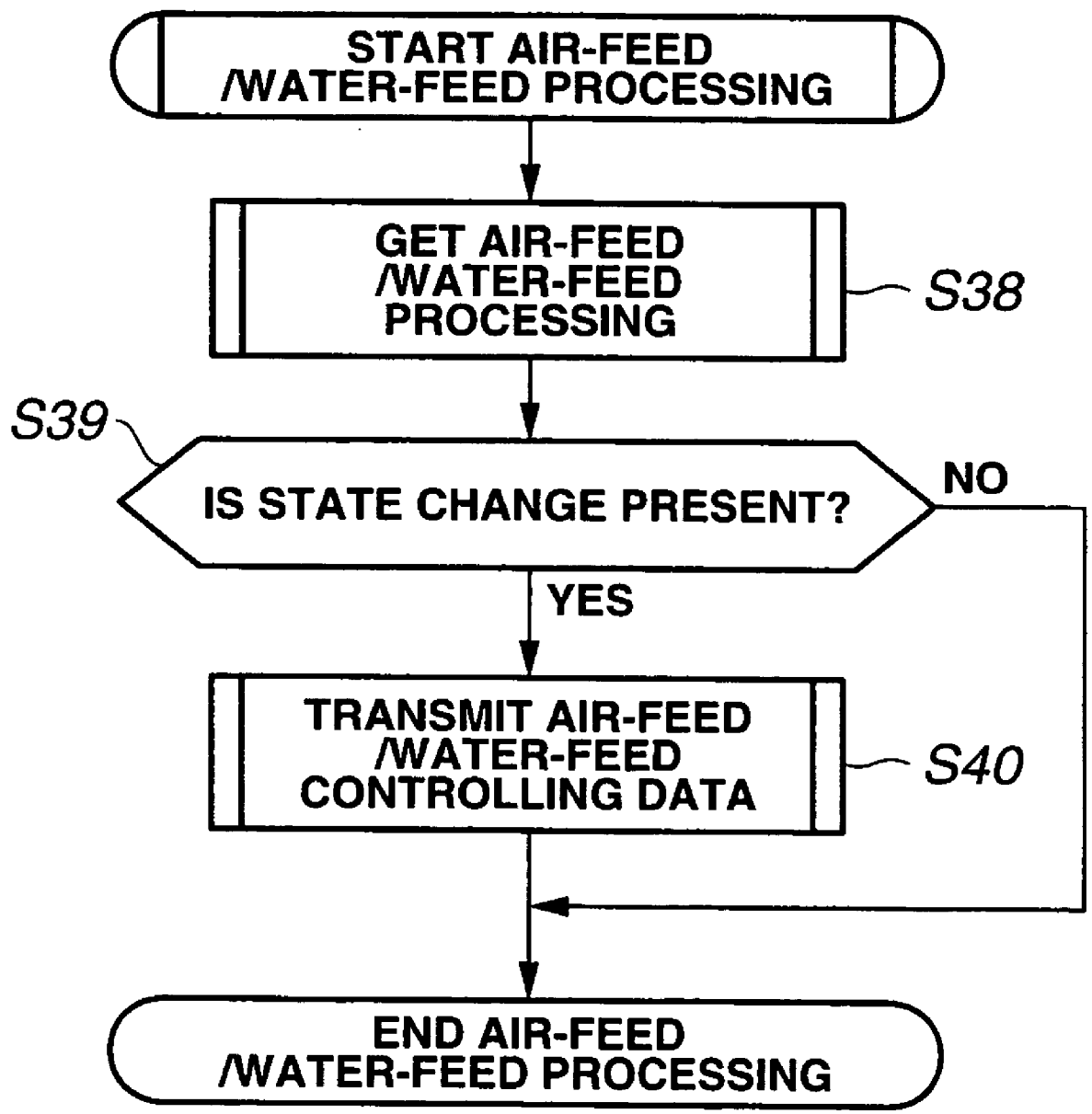
FIG. 37 is a flow chart showing contents of operation of controlling processing of air-feed and water-feed.

When air-feed/water-feed processing starts, as shown in Step S38 in FIG. 37, the state managing portion 81 of the controlling circuit 57 obtains state data of the air-feed/water-feed switch.

Operations of the air-feed/water-feed switch are detected by a switch push detecting portion 96 shown in FIG. 31; inputs information of that detection result is inputted; thereby the state managing portion 81 obtains state data of the air-feed/water-feed switch.

And as shown in Step S39, the state managing portion 81 determines a state change of the air-feed/water-feed switch. In Step S39, in the case where the state change of the air-feed/water-feed switch is determined to have occurred, the state managing portion 81 transmits, as shown in Step S40, air-feed/water-feed controlling data corresponding with the instruction of the air-feed/water-feed switch operated by a user to the side of AWS unit 4 through the transmitting/receiving unit 83.

The air-feed/water-feed controlling portion 122 in the AWS unit 4 implements controlling operation of the pump 65 and the electromagnetic unit 124 corresponding with those air-feed/water-feed controlling data. And, that air-feed/water-feed processing operation is finalized. On the other hand, in Step S32, in the case where no state change of the air-feed/water-feed switch is determined to have occurred, then without implementing processing in Step S40, that air-feed/water-feed processing operation is finalized. Here, the suction processing approximately likewise the air-feed/water-feed processing, description thereof will be omitted. Next, with reference to FIG. 38, processing of angle operating control will be described with reference to FIG. 38.

Figure 38:
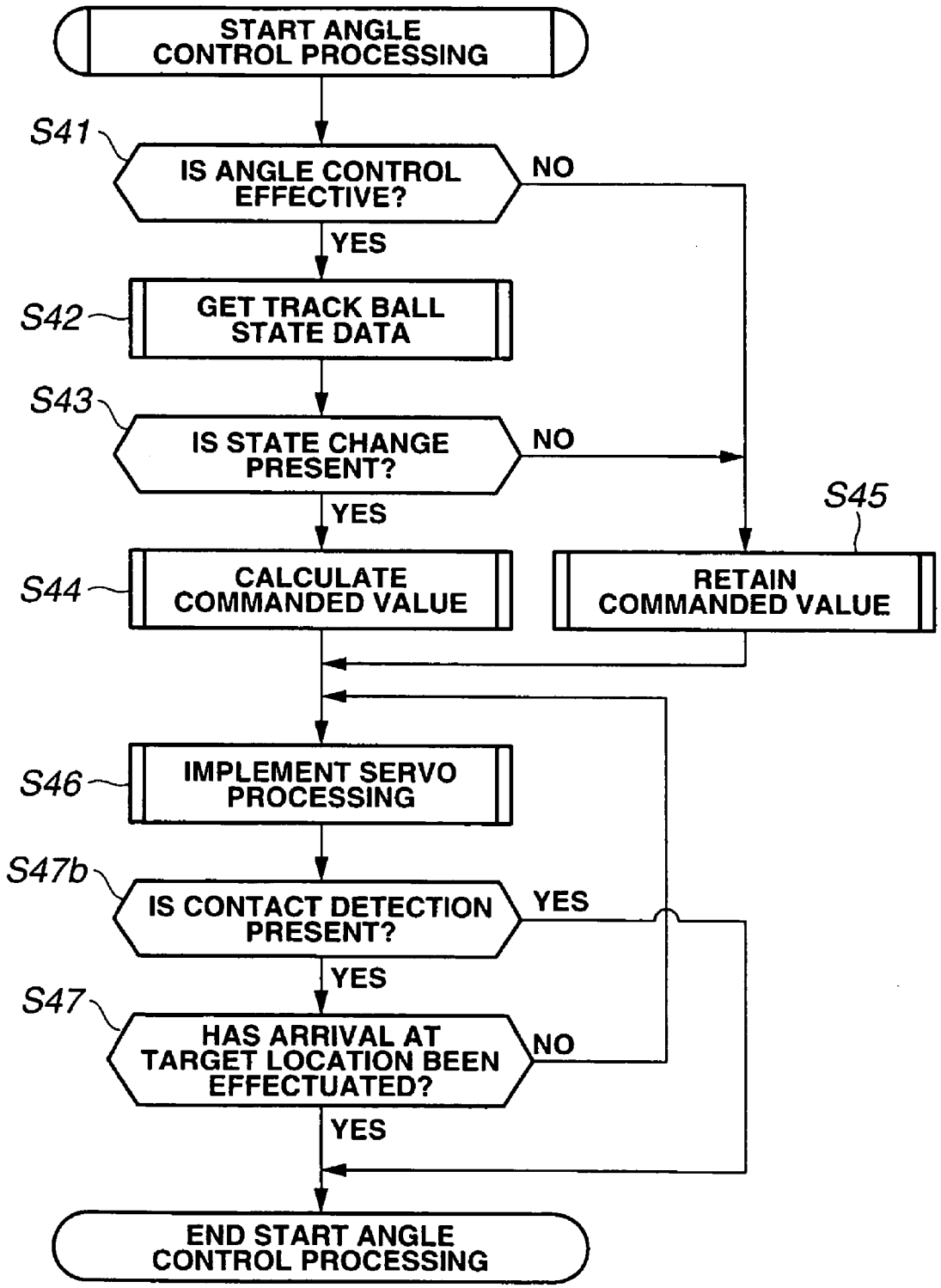
FIG. 38 is a flow chart showing controlling processing of an angle operation.

The flowchart in FIG. 38 shows a controlling processing in the case of providing the tip portion 24 of the insertion portion 21 with a contact sensor of implementing contact detection.

In the case of providing no contact sensor, processing shown in FIG. 13 will be implemented. As shown in FIG. 26, in the case of providing a contact sensor 124 as shown in FIG. 26, only processing after servo processing in Step S46 is difference from the case shown in FIG. 13. Therefore, operations after Step S46 will be described.

In the present embodiment, in the case where the state managing portion 81 implements angle operating control onto angle operation, the state managing portion 81 takes in the detection result by the contact sensor as shown in Step S47b through the contact sensor detecting portion, in the midst of starting servo processing by Step S46 as shown in FIG. 13, and thereby detects (determines) whether or not the tip portion 24 is in contact with the inner wall and the like inside the body cavity with pressure not less than an adequate value.

And in the case where the state managing portion 81 determines that the contact is made no less than an adequate value, the step goes forward to next Step S47, the state managing portion 81 determines, based on the detected value of the encoder, whether or not target positioning corresponding with the angle command value has been achieved; and in the case where target positioning has not yet been achieved, the step goes back to Step S46 and on the contrary in the case where target positioning has been achieved, control processing on that angle operation is finalized.

On the other hand, in Step S47b, in the case where the state managing portion 81 determines that the contact is made with an adequate value or more, no processing in next Step S47 will be implemented but the control processing on the angle operation is finalized.

Thus, in the case where an angle operation is implemented, the state managing portion 81 implements control processing to cause the curving portion 27 to curve up to the target position corresponding with the command value by the angle operation; but in the case where the tip portion 24 contacts the inner wall and the like of the body cavity with pressure over a set value, controls so as to restrain further curvature.

Accordingly, in the case of inserting the insertion portion 21 into a body cavity, a user tries to insert it along the interior of the curved conduit and therefore implements angle operations; and in that case, any contact with pressure over a set value can be avoided and therefore, pain imparted to a patient can be alleviated and smooth insertion becomes feasible.

Here, it is advisable that rigidity is further changed by the rigidity-variable actuator based on the detected output of the contact sensor.

Figure 18:
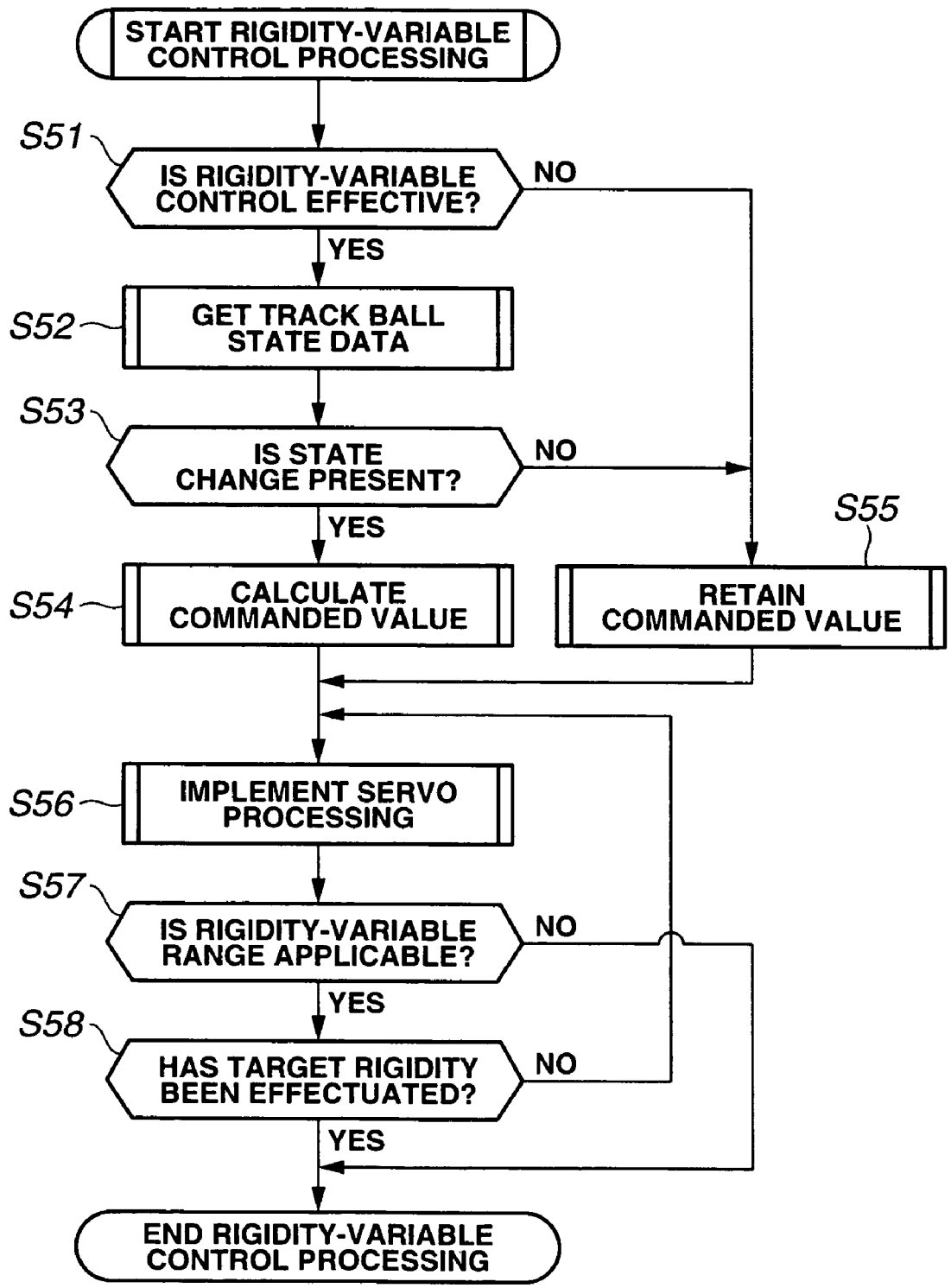
FIG. 18 is a flow chart showing a control operation with regard to a rigidity-variable operation.

In addition, also in the present embodiment, controlling processing of the rigidity-variable operation shown in FIG. 18 is implemented. In addition, the UPD unit 76 detects, with the UPD coil unit 8, the position of the UPD coil 58 disposed inside the insertion portion 21 of the endoscope 3G, calculates an insertion shape of the insertion portion 21 and display the insertion portion shape, that is, a UPD image, on the display screen of the observation monitor 6.

FIG. 39A to FIG. 39D respectively shows the right side menu window and the left side UPD image in a corresponding state; and shows that a user selects/sets rigidity of the rigidity-variable actuators 54A and 54B with the menu window, and in that case, colors correspond with the set rigidity on the rigidity portions of the rigidity-variable actuators 54A and 54B provided in a plurality of places (two places as a specific example) are displayed and thereby rigidity of those portions is made more identifiable.

Figure 39A:
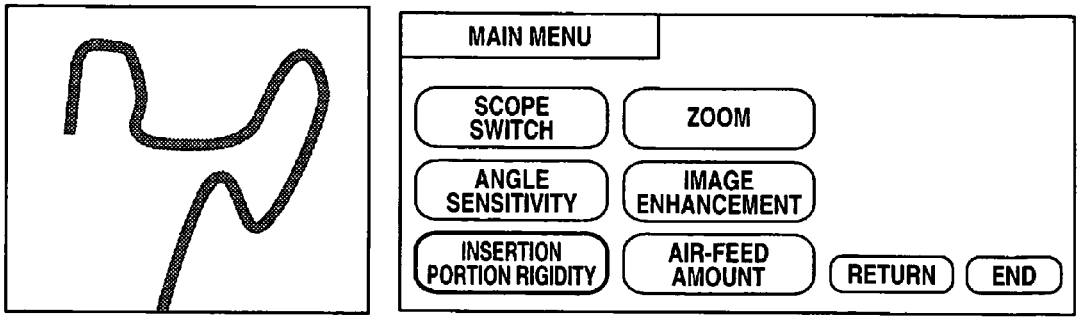
FIG. 39A to FIG. 39D are operation explanatory diagrams showing rigidity-variable setting operations and UPD images corresponding with those operations.

FIG. 39A shows the display state of the main menu and, under that display state, a user selects insertion portion rigidity-variable. In that case, since the UPD image will be immediately prior to selection of the insertion portion rigidity-variable, the sections A and B of the rigidity-variable actuators 54A and 54B are displayed without being discriminated from the portions other than those sections A and B.

Figure 39B:
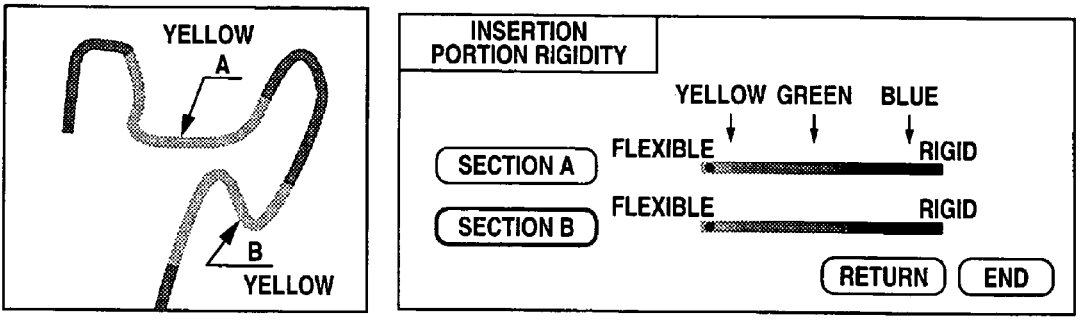

As in FIG. 39B, when the insertion portion rigidity-variable is selected, section ranges of set rigidity for the sections A and B of two rigidity-variable actuators 54A and 54B in the two places are shown to impart a rigidity setting window on which rigidity spanning from the state with flexible (soft) rigidity to the state with hard rigidity should be set on those sections A and B; and the current rigidity levels are indicated by circles respectively. In that case, from flexible state to rigid state, respectively difference display colors are displayed.

Accordingly, in the corresponding UPD image, the portion of the rigidity-variable actuator is displayed in color with display color corresponding with rigidity set to the rigidity-variable actuator. In the state of FIG. 39B, the rigidity section is set to a state close to "flexible"; and the sections A and B of the rigidity-variable actuators 54A and 54B in the UPD image in that case is displayed in yellow color.

Figure 39C:
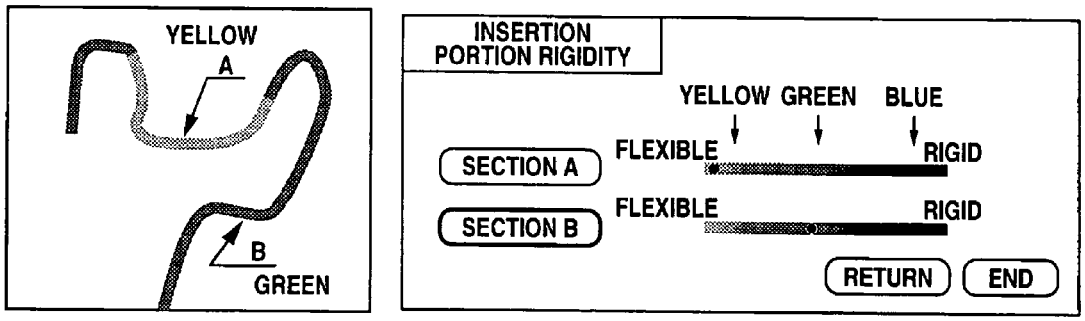

FIG. 39C is a case where rigidity of the section B of the rigidity-variable actuator 54B, for example, is set to rigidity in the vicinity to the center in the state of FIG. 39B; and the section B of the rigidity-variable actuator 54B in the UPD image in that case is displayed in green color.

Figure 39D:
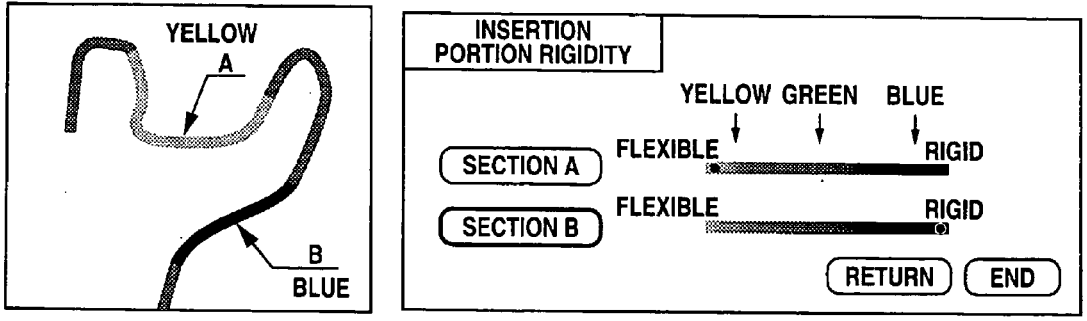

In addition, FIG. 39D is a case where rigidity of the section B of the rigidity-variable actuators 54B, for example, is set to rigid (rigid value) in the state of FIG. 39B or FIG. 39C; and the section B of the rigidity-variable actuator 54B in the UPD image in that case is displayed in blue color.

Displaying like that, a user can set rigidity of rigidity-variable actuators 54A and 54B freely and the portions of the sections A and B of the set rigidity-variable actuators 54A and 54B are displayed in colors corresponding with set rigidity, and therefore, the user can easily identify rigidity of the rigidity-variable actuators 54A and 54B.

In addition, since the shape of the insertion portion 21 is displayed by the UPD coil 58, an operator can implement insertion work and the like of the insertion portion 21 easily.

According to the endoscope 3G of the present embodiment forming an endoscope system 1B of implementing such an operation, that endoscope 3G is made splittable in the operation portion 22 to the endoscope main body 18 and the tube unit 19 to make the side of tube unit 19 into a disposable type and thereby it is possible to implement cleaning, sterilization and the like on the endoscope main body 18 easily.

That is, the air-feed/water-feed conduit 60a and the suction conduit 61a in the endoscope main body 18 can be made substantially short and accordingly is apt to undergo cleaning and sterilization compared with the cases of the prior art where a universal cable corresponding with the tube unit 19 is formed integrally.

In addition, in that case, in the case of the prior art where a universal cable corresponding with the tube unit 19 is formed integrally, the universal cable is provided in a connected row arrangement from the operation portion 22 so as to be made bent, but in the present embodiment, the connector portion 51 of the operation portion 22 will be replaced by a conduit connector 51a which is slightly bent and the other portions are replaced by the air-feed/water-feed conduit 60a which extends approximately linearly and the suction conduit 61a, and therefore it is possible to implement processing such as cleaning, sterilization, drying and the like inside the conduits easily and in a short time period. Accordingly, it is possible to set within a short time period to such a state that endoscope inspection can be implemented.

In addition, the present embodiment is structured to connect the endoscope main body 18 to the tube units 19 contactless and detachably, even if the endoscope main body 18 is cleaned and sterilized repeatedly, no conduction defects in contact and the like will occur in the case of not being contactless but reliability can be improved.

In addition, the present embodiment is structured to provide the operation portion 22 with a great number of operation means such as angle operation means, air-feed/water-feed operation means, suction operation means, rigidity-variable means, freeze operation means, release operation means and the like and carry out intensive (concentrated) control by the controlling circuit 57 with those operation means provided inside the operation portion 22. In addition, that controlling circuit 57 is structured to intensively control light emitting means of emitting lighting light for capturing images and image capturing means for capturing images together with the above described operation means.

Thus, the present embodiment is structured to intensively control respective functions provided in the endoscope main body 18 with the controlling circuit 57 provided inside the operation portion 22; and intensively control respective functions on operation means for the AWS unit 4 connected to the endoscope main body 18 and the endoscope system controlling apparatus 5 of transmitting/receiving information wirelessly; and therefore, a user (more specifically an operator) can implement respective types of operations freely with respective types of operation means provided in the operation portion 22 and thereby it is possible to improve operability by a large margin.

In particular, in the present embodiment, the controlling circuit 57 of implementing intensive control is provided inside the operation portion 22, and thereby the controlling circuit 57 is designed to packetize and the like the image data derived by capturing images with the CCD 25 and the respective signals by the operation means to transmit commonly with a pair of signal lines 71b and therefore the number of electric signal lines can be reduced (specifically, two signal lines for transmitting signals and two power supply lines for transmitting electric power can be reduced. In addition, utilization of respective one of the signal line and the power supply line in common will be able to make three cables in total.) Accordingly, it is possible to reduce the number of signal lines to be required to be inserted through into the tube unit 19 connected to the connecting portion in the operation portion 22, making the side of the tube unit 19 disposable.

In addition, reducing the number of signal lines to be inserted through the tube unit 19, the tube unit 19 can be made thinner in diameter and more apt to curve and operability in the case where a user operates can be improved.

Here, embodiments and the like configured by partially combining the above described respective embodiments and the like will belong to the present invention.

What is claimed is:

1. An endoscope comprising:
    an insertion portion provided with a freely curvable curving portion on a distal end side of the insertion portion;
    a grip portion provided at a base end side of the insertion portion and grasped by an operator;
    an instructing operation portion, which is present at the grip portion and in its periphery, with a function of implementing a curve instructing operation of the curving portion and a function of implementing another instructing operation different from the curve instructing operation; and
    a curved shape display processing portion for implementing curved shape display processing for displaying three-dimensionally a curved shape near the curving portion in the case of implementing a curve instructing operation on the curving portion by the instructing operation portion on a display, the curved shape display processing portion being provided inside the endoscope,
    wherein the curved shape display processing portion comprises:
        a displacement detecting portion for detecting displacement in a vertical direction and in a horizontal direction of a curve actuator and for detecting a total displacement in the vertical direction and the horizontal direction in the curve actuator, the curve actuator for curving the curving portion;
        a curve radius detecting portion for detecting curve radius when approximating a curved shape of a curving portion to a circular arc based on information from the curving portion;
        an angle component detecting portion for detecting angle components corresponding to displacement components in the horizontal direction of the total displacement;
        a depiction processing portion for implementing depiction processing of displaying a curve shape of the curving portion corresponding with the total displacement; and
        a rotational depiction processing portion for implementing depiction processing of causing a depiction model of the curving portion generated by the depiction processing to rotate by the angle component to the display.

2. The endoscope according to claim 1, wherein the instructing operation portion has a direction instructing operation portion in a plurality of different directions in order to implement a curving instructing operation of the curving portion; and a switching instructing portion for use in switching functions between the curving instructing operation and the other instructing operations.

3. The endoscope according to claim 2, wherein the direction instructing operation portion is formed of an operating pad having a track ball or a plurality of switches.

4. The endoscope according to claim 2, having a switching operation detecting portion for detecting a switching operation by the switching portion.

5. The endoscope according to claim 4, having a display processing portion for implementing processing for displaying information selectable by the direction instructing operation portion in the case where a switching operation is detected by the switching operation detection portion.

6. The endoscope according to claim 5, wherein processing of displaying the selectable information includes processing for displaying a movable cursor by the direction instructing operation portion.

7. The endoscope according to claim 5, wherein processing of displaying the selectable information includes a function of the other instructing operation different from the curving instructing operation allocated to the direction instructing operation portion.

8. The endoscope according to claim 7, having a switch of implementing a determining operation of determining to allocate an operation by the direction instructing operation portion to the other functions provided in the periphery of the direction instructing operation portion.

9. The endoscope according to claim 1, wherein the instructing operation portion has a rotatably supported ball portion and a switch portion which is utilized for switching, with pushing operations onto the ball portion, functions between the curving instructing operation of the curving portion and the other instructing operations.

10. The endoscope according to claim 9, having two rotation direction detecting portions in order to detect rotation directions of the ball portion.

11. The endoscope according to claim 9, having a control processing portion for implementing control processing for setting selection instructing operation signal for selecting and operating function of the other instructing operation on instructing operation signals generated in the case where the ball portion is operated to rotate by operations of the switch portion.

12. The endoscope according to claim 1, wherein the instructing operation portion is configured by using a track ball having a rotatably supported ball portion.

13. The endoscope according to claim 1, wherein the instructing operation portion is provided on a base end surface of a substantially cylinder portion forming the grip portion.

14. The endoscope according to claim 13, wherein the base end surface is an inclined surface making an obtuse angle from an axis direction of the grip portion.

15. The endoscope according to claim 14, wherein the curve instructing operation portion is provided on the inclined surface to be located near a thumb of a hand gripping the grip portion.

16. The endoscope according to claim 14, wherein the inclined surface falls within the angle range of 120° to 150° on an axis direction of the grip portion.

17. The endoscope according to claim 1, wherein at least one switch is disposed adjacent to the instructing operation portion.

18. The endoscope according to claim 1, having a control processing portion of implementing control processing corresponding with the instructing operation by the instructing operation portion.

19. The endoscope according to claim 1, wherein the instructing operation portion forms a shape substantially axisymmetrical on a reference line extending in the longitudinal direction of the grip portion.

20. The endoscope according to claim 19, wherein a plurality of instructing operation portions are disposed substantially axisymmetrically at the grip portion and in its periphery.

21. The endoscope according to claim 1, having a connecting portion provided in the grip portion or in its periphery and detachably connectable to a tube unit in which at least one conduit is inserted through.

22. The endoscope according to claim 1, having instructing operation detecting portion for detecting an operation of the instructing operation portion.

23. The endoscope according to claim 1, wherein
the curving portion possesses a plurality of curving portion shape-variable mechanisms to change a shape of the curving portion by applying a voltage;
there present at the grip portion and in its periphery is a curving portion shape-variable operation portion of instructing a curving portion shape-variable controlling portion of controlling the curving portion shape-variable mechanisms to change a shape of a curving portion so as to change a shape of the curving portion.

24. The endoscope according to claim 23, wherein there provided at the grip portion and in its periphery is a switch enabling an operator to allocate a function of the curving portion shape-variable operation portion.

25. The endoscope according to claim 23, wherein the curving portion shape-variable mechanisms are made of conductive polymer artificial muscle.

26. An endoscope comprising:
an insertion portion provided with a curvable curving portion on a distal end side;
a grip portion provided in a base end side of the insertion portion and grasped by an operator;
a curve instructing operation portion provided at the grip portion and in its periphery and implementing curve instructing operation on the curving portion;
a switching portion for switching instructing operation signals for the curve instructing operation portion by implementing another instructing operation different from the curve instructing operation for the curve instructing operation portion; and
a curved shape display processing portion for implementing curved shape display processing for displaying three-dimensionally a curved shape near the curving portion in the case of implementing a curve instructing operation on the curving portion by the instructing operation portion on a display, the curved shape display processing portion being provided inside the endoscope,
wherein the curved shape display processing portion comprises:
a displacement detecting portion for detecting displacement in a vertical direction and in a horizontal direction of a curve actuator and for detecting a total displacement in the vertical direction and the horizontal direction in the curve actuator, the curve actuator for curving the curving portion;
a curve radius detecting portion for detecting curve radius when approximating a curved shape of a curving portion to a circular arc based on information from the curving portion;

an angle component detecting portion for detecting angle components corresponding to displacement components in the horizontal direction of the total displacement;

a depiction processing portion for implementing depiction processing of displaying a curve shape of the curving portion corresponding with the total displacement; and a rotational depiction processing portion for implementing depiction processing of causing a depiction model of the curving portion generated by the depiction processing to rotate by the angle component to the display.

27. The endoscope according to claim 26, wherein the curve instructing operation portion is formed of a rotatably supported ball portion.

* * * * *